US012268718B2

(12) United States Patent
McKenna

(10) Patent No.: US 12,268,718 B2
(45) Date of Patent: *Apr. 8, 2025

(54) CONTROL OF CELLULAR REDOX LEVELS

(71) Applicant: Labyrinth Holdings LLC, Sugar Land, TX (US)

(72) Inventor: Elizabeth McKenna, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/348,005

(22) Filed: Nov. 10, 2016

(65) Prior Publication Data
US 2017/0232047 A1    Aug. 17, 2017

Related U.S. Application Data

(63) Continuation-in-part of application No. 14/640,075, filed on Mar. 6, 2015, now Pat. No. 9,931,398, which is a continuation of application No. 14/034,044, filed on Sep. 23, 2013, now abandoned, and a continuation-in-part of application No. 13/743,194, filed on Jan. 16, 2013, now Pat. No. 9,713,630.

(60) Provisional application No. 62/253,542, filed on Nov. 10, 2015, provisional application No. 61/704,090, filed on Sep. 21, 2012, provisional application No. 61/586,975, filed on Jan. 16, 2012.

(51) Int. Cl.
| A61K 35/747 | (2015.01) |
| A61K 35/742 | (2015.01) |
| A61K 35/744 | (2015.01) |
| A61K 38/48  | (2006.01) |
| A61K 45/00  | (2006.01) |
| C12N 1/06   | (2006.01) |
| C12N 1/20   | (2006.01) |
| G01N 33/88  | (2006.01) |
| A61K 9/00   | (2006.01) |
| A61K 9/20   | (2006.01) |
| A61K 9/68   | (2006.01) |

(52) U.S. Cl.
CPC .......... *A61K 35/747* (2013.01); *A61K 35/742* (2013.01); *A61K 35/744* (2013.01); *A61K 38/482* (2013.01); *A61K 45/00* (2013.01); *C12N 1/06* (2013.01); *C12N 1/20* (2013.01); *C12Y 304/21043* (2013.01); *G01N 33/88* (2013.01); *A61K 9/0056* (2013.01); *A61K 9/0058* (2013.01); *A61K 9/2004* (2013.01); *G01N 2800/52* (2013.01); *G01N 2800/7009* (2013.01)

(58) Field of Classification Search
CPC .. A61K 35/747; A61K 35/742; A61K 35/744; C12N 1/06; G01N 2800/7009
See application file for complete search history.

(56) References Cited

U.S. PATENT DOCUMENTS

| 3,806,290 | A | 4/1974 | Graff et al. | |
| 4,322,405 | A * | 3/1982 | Schulthess | A61K 35/74 424/520 |
| 5,716,615 | A | 2/1998 | Vesely et al. | |
| 5,955,321 | A | 9/1999 | Bijl et al. | |
| 6,194,388 | B1 | 2/2001 | Krieg et al. | |
| 6,207,646 | B1 | 3/2001 | Krieg et al. | |
| 6,214,806 | B1 | 4/2001 | Krieg et al. | |
| 6,218,371 | B1 | 4/2001 | Krieg et al. | |
| 6,239,116 | B1 | 5/2001 | Krieg et al. | |
| 6,281,191 | B1 | 8/2001 | Slesarev et al. | |
| 6,339,068 | B1 | 1/2002 | Krieg et al. | |
| 6,767,557 | B2 | 7/2004 | Ulrich et al. | |
| 7,265,152 | B2 | 9/2007 | Saha et al. | |
| 7,959,911 | B2 | 6/2011 | DeSimone | |
| 8,007,783 | B2 | 8/2011 | Miller | |
| 8,278,089 | B2 | 10/2012 | Miller | |
| 8,304,226 | B2 | 11/2012 | Miller | |
| 9,713,630 | B2 * | 7/2017 | McKenna | A61K 38/482 |
| 9,931,398 | B2 | 4/2018 | Mckenna et al. | |
| 2002/0164341 | A1 | 11/2002 | Davis et al. | |
| 2004/0129174 | A1 | 7/2004 | Bunick et al. | |
| 2005/0124053 | A1 * | 6/2005 | Moen | A23K 40/20 435/170 |
| 2006/0286205 | A1 * | 12/2006 | Fichtali | A23L 33/12 435/41 |
| 2007/0179101 | A1 | 8/2007 | Kitagawa et al. | |
| 2008/0045473 | A1 | 2/2008 | Uhlmann et al. | |

(Continued)

FOREIGN PATENT DOCUMENTS

| EP | 1178118 | 2/2002 |
| EP | 1920774 | 5/2008 |

(Continued)

OTHER PUBLICATIONS

Halliwell et al. 2004 (Measuring reactive species and oxidative damage in vivo and in cell culture: how should I do it and what do the results mean? British Journal of Pharmacology 142: 231-255).*

(Continued)

*Primary Examiner* — Mary Maille Lyons
(74) *Attorney, Agent, or Firm* — McDonnell Boehnen Hulbert & Berghoff LLP

(57) ABSTRACT

Disclosed herein are compositions and methods for regulating redox status and/or reducing oxidative stress in a subject, the methods and compositions comprising TLR agonists comprising bacterial lysates and/or lysate fractions. Also disclosed are compositions and methods comprising bacterial lysates and/or lysate fractions formulated or administered in combination with one or more other therapeutic or pharmaceutical agents.

10 Claims, 20 Drawing Sheets

(56) References Cited

U.S. PATENT DOCUMENTS

| | | | |
|---|---|---|---|
| 2008/0050353 | A1 | 2/2008 | Miller et al. |
| 2009/0297561 | A1* | 12/2009 | Pasternack ............. A61K 39/12 424/257.1 |
| 2011/0104134 | A1 | 5/2011 | Ihara et al. |

FOREIGN PATENT DOCUMENTS

| | | |
|---|---|---|
| FR | 2951377 | 4/2011 |
| JP | H04264034 | 9/1992 |
| JP | H0656680 | 3/1994 |
| JP | 09301878 | 11/1997 |
| JP | H09301877 | 11/1997 |
| JP | H1086 | 1/1998 |
| JP | 2000004830 | 1/2000 |
| JP | 2002332242 | 11/2002 |
| JP | 2005237328 | 2/2004 |
| JP | 2005247780 | 9/2005 |
| JP | 2006507362 | 3/2006 |
| JP | 2009280606 | 12/2009 |
| JP | 2010504278 | 2/2010 |
| JP | 201168643 | 4/2011 |
| JP | 2011516521 | 5/2011 |
| JP | 2012502026 | 1/2012 |
| WO | WO 98/40100 | 9/1998 |
| WO | 2003015711 | 2/2003 |
| WO | 2003026688 | 4/2003 |
| WO | WO 2004037182 | 5/2004 |
| WO | 2007013613 | 2/2007 |
| WO | 2008000783 | 1/2008 |
| WO | 2009124954 | 10/2009 |
| WO | 2010001509 | 1/2010 |
| WO | 2010027344 | 3/2010 |
| WO | WO 2010144943 | 8/2011 |
| WO | 2011151431 | 12/2011 |
| WO | 2013109635 | 7/2013 |
| WO | WO2014/047588 | 3/2014 |

OTHER PUBLICATIONS

Tran et al. 2010 (Immune response following vaccination against *Salmonella enteritidis* using 2 commercial bacterins in laying hens; Canadian Journal of Veterinary Research, vol. 74, No. 3, Jul. 2010, pp. 185-192(8)).*

Basu et al. 2001 (Raised levels of F2-isoprostanes and prostaglandin in F2a in different rheumatic diseases; Ann Rheum Dis 60: 627-631).*

Mohammadi et al. 2015 (Effects of Probiotics on Biomarkers of Oxidative Stress and Inflammatory Factors in Petrochemical Workers: A Randomized, Double blind, Placebo-controlled Trial; Int J Prev Med. 6(82) (Year: 2015).*

Blanton et al. 2015 (Probiotics Blunt the Anti-Hypertensive Effect of Blueberry Feeding in Hypertensive Rates without Altering Hippuric Acid Production; PLOS One10(11): 1-14). (Year: 2015).*

Mikelsaar et al. 2009 (Lactobacillus fermentum ME-3—an antimicrobial and antioxidative probiotic; Microbial Ecology in Health and Disease 21: 1-27) (Year: 2009).*

Konishi et al. 2006 (Increased lipid peroxidation in patients with non-alcoholic fatty liver disease and chronic hepatitis C as measured by the plasma level of 8-isoprostane; Journal of Gastroenterology and Hepatology 21: 1821-1825). (Year: 2006).*

Kullisaar et al., 2011 (An antioxidant probiotic reduces postprandial lipemia and oxidative stress; Central European Journal of Biology; Cent. Eur. J. Biol. 6(1): 32-40) (Year: 2011).*

Kullisaar et al., 2009 (Two antioxidative bacilli strains as promising probiotics; International Journal of Food Microbiology 72: 215-224) (Year: 2009).*

Lin et al. 2000 (Antioxidative Effect of Intestinal Bacteria Bifidobacterium longum ATCC 15708 and Lactobacillus acidophilus ATCC 4356; Digestive Diseases and Sciences 45(8): 1617-1622). (Year: 2000).*

Kataria et al. 2009 (Probiotic microbes: do they need to be alive to be beneficial? Nutritional Reviews 67(9): 546-550) (Year: 2009).*

Choi et al. 2005 (Effects of Lactobacillus strains on cancer cell proliferation and oxidative stress in vitro; Letters in Applied Microbiology 42:452-458) (Year: 2005).*

Krieg et al, "CpG motifs in bacterial DNA trigger direct B-cell activation," Nature, vol. 374, pp. 546-549 (1995).

Kumar et al., "Cancer-preventing attributes of probiotics: an update," Int J Food Sci Nutr. 61(5):473-96 (2010).

Laman et al., "Identification of pentadecapeptide mimicking muramyl peptide," Vaccine 25(15):2900-2906 (2006).

Lipford et al., "Bacterial DNA as immune cell activator," Trends Microbiol. 6(12):496-500 (1998).

Maletzki Claudia et al. "Bacterial Immunotherapy—Antitumoral Potential of the Streptococcal Toxin Streptolysin S-," Pancreatic Cancer—Clinical Management, Prof. Sanjay Srivastava, 163-176 (2012).

Messina et al., "Stimulation of in vitro murine lymphocyte proliferation by bacterial DNA," J. Immunol. 147:1759-1764 (1991).

Peng et al., "Protective effects of Lactobacillus plantarum NDC 75017 against lipopolysaccharide-induced liver injury in mice," Inflammation 37(5):1599-607 (2014).

Pineda et al., "A randomized, double-blinded, placebo-controlled pilot study of probiotics in active rheumatoid arthritis," Med Sci Monit. 17(6):CR347-54 (2011).

Pinegin et al., "The occurrence of natural antibodies to minimal component of bacterial cell wall (N-acetylglucosaminyl-N-acetylmuramyl dipeptide) in sera from healthy humans," Immunol Lett. 47(1-2):33-7 (1995).

Pisetsky, "The immunologic properties of DNA," J Immunol. 156(2):421-3 (1996).

Rachmilewitz et al., "Toll-like receptor signaling mediates the anti-inflammatory effects of probiotics in murine experimental colitis," Gastroenterology 126(2):520-8 (2004).

Rau, "Adalimumab (a fully human anti-tumour necrosis factor alpha monoclonal antibody) in the treatment of active rheumatoid arthritis: the initial results of five trials," Ann Rheum Dis. 61 Suppl 2:ii70-3 (2002).

Reis et al. "LPS-induced formation of immunoproteasomes: TNF-α and nitric oxide production are regulated by altered composition of proteasome-active sites," Cell Biochem Biophys 60(1-2):77-88 (2011).

Siebler et al., "Immunization with the immunoregulatory saprophytic bacterium, *Mycobacterium vaccae*, enhances fear extinction in adult rnale Sprague Dawley rats," 24th Annual Meeting Of The InternationalBehavioral Neuroscience Society 24:82 (2015).

Squier et al., "Lipid Content and Water Permeability of Skin and Oral Mucosa," J Invest Dermatol. 96(1):123-6 (1991).

Te et al., "Mechanism of action of ribavirin in the treatment of chronic hepatitis C," Gastroenterol. Hepatol., 3:218-225 (2007).

Tokunaga et al., "Antitumor activity of deoxyribonucleic acid fraction from *Mycobacterium bovis* BCG. I. Isolation, physicochemical characterization, and antitumor activity," J Natl Cancer Inst. 72(4):955-62 (1984).

Vollmer et al., "Immunotherapeutic applications of CpG oligodeoxynucleotide TLR9 agonists," Advanced Drug Delivery Reviews 61(3):195-204 (2009).

Weeratna et al., "Potential use of CpG ODN for cancer immunotherapy. 18-20Update on cancer therapeutic," Update on Cancer Therapeutics 1(1):49-58 (2006).

Yi, et al., "CpG oligodeoxyribonucleotides rescue mature spleen B cells from spontaneous apoptosis and promote cell cycle entry," J Immunol. 160(12):5898-906 (1998).

Zhang et al., "CpG ODN pretreatment attenuates concanavalin A-induced hepatitis in mice," Int Immunopharmacol (1):79-85 (2010).

Zimmerman et al., "Post-traumatic anxiety associates with failure of the innate immune receptor TLR9 to evade the pro-inflammatory NFκB pathway," Transl Psychiatry 2(2): e78 (2012).

Zou et al. "An APAF-1.cytochrome c multimeric complex is a functional apoptosome that activates procaspase-9," J Biol Chem. 274(17):11549-56 (1999).

(56) References Cited

OTHER PUBLICATIONS

Zuezem et al., "Peginterferon alfa-2a in patients with chronic hepatitis," N Engl J Med. 343(23):1666-72 (2000).
International Preliminary Report on Patentability corresponding to Application No. PCT/US2013/021752; mailed May 15, 2013 pp. 1-7.
International Search Report for corresponding International patent application No. PCT/US 2013/061236, mailed Jan. 16, 2014, pp. 1-9.
International Preliminary Report on Patentability corresponding to Application No. PCT/US 2013/061236; mailed Mar. 24, 2015 pp. 1-12.
Written Opinion for corresponding International patent application No. PCT/US 2013/061236; mailed Dec. 12, 2013, pp. 1-11.
International Search Report and Written Opinion for corresponding International patent application No. PCT/US2016/061247, mailed Jan. 26, 2017, pp. 1-16.
International Search Report for corresponding International patent application No. PCT/US2013/021752, mailed May 15, 2013.
Written Opinion for corresponding International patent application No. PCT/US2013/021752, mailed May 15, 2013.
Krieg, "Mechanisms and applications of immune stimulatory CpG oligodeoxynucleotides," Biochim. Biophys. Acta, 1489: 107-116 (1999).
Tokunaga et al., "A synthetic single-stranded DNA, poly(dG,dC), induces interferon-alpha/beta and -gamma, augments natural killer activity, and suppresses tumor growth," Jpn. J. Cancer Res. 79:682-686 (1988).
Hu et al., "WD-40 repeat region regulates Apaf-1 self-association and procaspase-9 activation," J Biol Chem. 273(50):33489-94 (1998).
Iliev et al., "Strong immunostimulation in murine immune cells by Lactobacillus rhamnosus GG DNA containing novel oligodeoxynucleotide pattern" Cell Microbiol. 7(3):403-14 (2005).
Inohara et al., "Nod1, an Apaf-1-like activator of caspase-9 and nuclear factor-kappaB," J Biol Chem. 274(21):14560-7 (1999).
Kim et al., "Probiotic genomic DNA reduces the production of pro-inflammatory cytokine tumor necrosis factor-alpha," FEMS Microbiol Lett.328(1):13-9 (2012).
Kozlov et al., Effect on human complement of blastolysin and the glycopeptide (MDP and GMDP) and carbohydrate fragments of peptidoglycans, Bioorg Khim. 11(11):1510-8 (1985).
Kerkmann et al., "Spontaneous formation of nucleic acid-based nanoparticles is responsible for high interferon-alpha induction by CpG-A in plasmacytoid dendritic cells," J Bioi. Chem. 280(9):8086-93 (2005).
Krieg, "Toll-like receptor 9 (TLR9) agonists in the treatment of cancer," Oncogene 27, 161-167 (2008).
Krieg, "Leukocyte Stimulation by Oligodeoxynucleotides," in Applied Antisense Oligonucleotide Technology, C. A. Stein and A. M. Krieg, (Eds.), John Wiley and Sons, Inc., New York, N.Y., pp. 431-448 (1998).
"Fundamentals of Freeze-Drying," Pharm. Biotechnol., 14:281-360 (2002).
"Nitric oxide synthesis protects against oxidative stress: Bacillus Subtilis Bacterium". Online:http://www.asknature.org/strategy/2a2bf810dc95e1eebc2d1d1055fba0ec#.UxV6XfldVIF.
Becker, "CpG ODNs treatments of HIV-1 infected patients may cause the decline of transmission in high risk populations—a review, hypothesis and implications," Virus Genes 30(2):251-66 (2005).
Beutler et al., "Synergy between TLR2 and TLR4: a safety mechanism," Blood Cells Mol Dis. 27(4):728-30. (2001).
Bressanelli et al., "Structural Analysis of the Hepatitis C Virus RNA Polymerase in Complex with Ribonucleotides," Journal of Virology 76(7):3482-3492 (2002).
Ceprnja et al. "Oxidative Stress Markers in patients with post-traumatic stress disorder."Collegium Antropologicum,"" 35(4):1155-60 (2011).
Forsyth et al., "Lactobacillus GG treatment ameliorates alcohol-induced intestinal oxidative stress, gutleakiness, and liver injury in a rat model of alcoholic steatohepatitis," Alcohol 43(2): 163-172 (2009).
Fukata et al., "Toll-like receptors (TLRs) and Nod-like receptors (NLRs) in inflammatory disorders," Seminars in Immunology 21:242-253 (2009).
Galey et al., "The in vitro permeability of skin and buccal mucosa to selected drugs and tritiated water," J Invest Dermatol. 67(6):713-7 (1976).
Galigniana et al. "Regulation of the glucocorticoid response to stress-relateddisorders by the Hsp90-binding immunophilin FKBP51," Journal of Neurochemistry 122:4-18 (2012).
Golovina et al., "Specific binding of glucosaminylmuramyl peptides to histones," FEBS Lett. 454(1-2):152-6 (1999).
Hacker et al., "CpG-DNA-specific activation of antigen-presenting cells requires stress kinase activity and is preceded by non-specific endocytosis and endosomal maturation," EMBO J. 17(21):6230-40 (1998).
Hartmann et al., "CpG DNA: a potent signal for growth, activation, and maturation of human dendritic cells," Proc Natl Acad Sci USA 96(16):9305-10 (1999).
Ayers et al., "Ability of *Streptococci* to survive pasteurization," Journal of Agricultural Research, vol. 2, No. 4, p. 321-330 (1914).
Basu et al., "Raised levels of F(2)-isoprostanes and prostaglandin F(2alpha) in different rheumatic diseases," Ann Rheum Dis. 60(6):627-31 (2001).
Blanton et al., "Probiotics Blunt the Anti-Hypertensive Effect of Blueberry Feeding in Hypertensive Rats without Altering Hippuric Acid Production," PLoS One 10(11):(1-14) (2015).
Chapot-Chartier et al., "Cell wall structure and function in lactic acid bacteria," Microb Cell Fact. 13 Suppl 1:S9 (2014).
Chassy et al., "Method for the lysis of Gram-positive, asporogenous bacteria with lysozyme," Appl Environ Microbiol. 39(1):153-8 (1980).
Halliwell et al., "Measuring reactive species and oxidative damage in vivo and in cell culture: how should you do it and what do the results mean?" Br J Pharmacol. 142(2):231-55 (2004).
Lecat et al., "The protein Nod2: an innate receptor more complex than previously assumed," Biochem Pharmacol. 80(12):2021-31 (2010).
Mikelsaar et al., "Lactobacillus fermentum ME-3—an antimicrobial and antioxidative probiotic," Microb Ecol Health Dis. 21(1):1-27 (2009).
Mohammadi et al., "Effects of Probiotics on Biomarkers of Oxidative Stress and Inflammatory Factors in Petrochemical Workers: A Randomized, Double-blind, Placebo-controlled Trial," Int J Prev Med. 2015; 6:82 (2015).
Ragland et al., "From bacterial killing to immune modulation: Recent insights into the functions of lysozyme," PLoS Pathog. 13(9) (2017).
Testro et al., "Toll-like receptors and their role in gastrointestinal disease," J Gastroenterol Hepatol. 24(6):943-54 (2009).
Tran et al., "Immune response following vaccination against *Salmonella enteritidis* using 2 commercial bacterins in laying hens," Canadian Journal of Veterinary Research, 74(3):185-192(8) (2010).
Adamberg et al, "The effect of temperature and pH on the growth of lactic acid bacteria: a pH-auxostat study," Int J Food Microbiol. 85(1-2):171-83 (2003).
Coakley et al., "Conjugated linoleic acid biosynthesis by human derived *Bifidobacteriurn* species," Journal of Applied Microbiology 94: 138-145 (2003).
Corzo, "Time, the forgotten dimension of ligand binding teaching," Biochem Mol Biol Educ 34(6):413-6 (2006).
Eckner et al., "Potential for the Low-Temperature Pasteurization of Dairy Fluids Using Membrane Processing," Journal of Food Protection, vol. 54, No. 10, pp. 793-797 (1991).
Kullisaar et al., "Two antioxidative lactobacilli strains as promising probiotics," Int J Food Microbiol. 72(3):215-24 (2002).
Kullisaar et al., "Antioxidative probiotic fermented goats' milk decreases oxidative stress-mediated atherogenicity in human subjects," Br J Nutr.90(2):449-56 (2003).

(56) References Cited

OTHER PUBLICATIONS

Seikagaku, "Structure and function of cytoplasmic pattern recognition receptor NLR," The Journal of Japanese Biochemical Society, vol. 82 (1), pp. 12-20 (2010). (English machine translation).
U.S. Department of Health and Human Services "Grade "A" Pasteurized Milk Ordinance," 2009 Revision (p. 1-382).
Vorobjeva, "Propionibacteria," Springer Science & Business Media, p. 149 (1999).
Wikipedia: "Pasteurization," retrieved from the Internet:URL:https://en.wikipedia.org/wiki/Pasteurization [retrieved on Jul. 26, 2018] (pp. 1-11).
Yamamoto (Ed.), Basic Pharmaceutical Science Textbook Series 10: Immunology, H Kagakudojin Co., Ltd., Apr. 20, 2012, 1st edition, 4th issue, pp. 156-159, pp. 230. (English machine translation).
Zufall et al., "The Biological Impact of Flash Pasteurization Over a Wide Temperature Interval," Journal of The Institute of Brewing 106(3): 163-167 (2000).
International Preliminary Report on Patentability corresponding to Application No. PCT/US2016/061247, mailed May 15, 2018, pp. 1-10.
Heeg, et al., "Bacterial DNA as an Evolutionary Conserved Ligand Signalling Danger of Infection to Immune Cells", Eur J Clin Microbial Infect Dis, vol. 17:464-469 (1998).
Silhavy, et al., "The Bacterial Cell Envelope", Cold Spring Harb Prespect 2010;2a000414.
Bartlett et al., "Understanding the Oral Mucosal Absorption and Resulting Clinical Pharmacokinetics of Asenapine," AAPS PharmSciTech, vol. 13, No. 4 (2012).
Inagawa et al., "Oral administration of lipopolysaccharides for the prevention of various diseases: benefit and usefulness," Anticancer Res., 31(7):2431-6 (2011).
Ivanov et al., "Structure, design, and synthesis of immunoactive peptides," Pure & Appl. Chem., vol. 59, No. 3, pp. 317-324 (1987).
Meshcheryakova et al., "Evidence for correlation between the intensities of adjuvant effects and NOD2 activation by monomeric, dimeric and lipophylic derivatives of N-acetylglucosaminyl-N-acetylmuramyl peptides," Vaccine 25(23):4515-20 (2007).
Namba et al., "Effect of oral administration of lysozyme or digested bacterial cell walls on immunostimulation in guinea pigs," Infect Immun. Feb.;31(2):580-3 (1981).
Narang et al., "Sublingual mucosa as a route for systemic drug delivery," International Journal of Pharmacy and Pharmaceutical Sciences 3:18-22 (2001).
Salazar et al., "Enzymatic lysis of microbial cells," Biotechnol Lett., 29(7):985-94 (2007).
Sasmaz et al., "Rubella seroprevalence in women in the reproductive period, Mersin, Turkey," Vaccine. 25(5):912-7 (2006).
Schroder et al., "Lipoteichoic acid (LTA) of *Streptococcus pneumoniae* and *Staphylococcus aureus* activates immune cells via Toll-like receptor (TLR)-2, lipopolysaccharide-binding protein (LBP), and CD14, whereas TLR-4 and MD-2 are not involved," J Biol Chem. 278(18):15587-94 (2003).
Silhavy et al., "The bacterial cell envelope," Cold Spring Harb Perspect Biol., 2(5):a000414 (2010).
Takahashi et al., "Immune Response of Mice to Orally Administered Lactic Acid Bacteria," Bioscience, Biotechnology, and Biochemistry, 57:9, p. 1557-1560 (1993).
Vauterin et al. 2000 (Synopsis on the Taxonomy of the Genus *Xanthomonas*; The American Phytopathological Society; Pub. No. P-2000-056-010; vol. 90, No. 7, p. 677) (2000).
Yamamoto et al., "Role of Nod2 in the development of Crohn's disease," Microbes and Infection, vol. 11(12):912-918 (2009).
Kumar et al., Critical Reviews in Microbiology, 2013; 39(3): 229-246.
Ramadan & Paczesny, Front Immunol. 2015;6:14.
Dukan S, Nystrom T, Genes Dev. 1998;12(21):3431-3441.
Achuthan et al., "Antioxidative potential of lactobacilli isolated from the gut of Indian people," Mol. Biol. Rep. 39(8):7887-97 (2012).
Andrews et al., "Heat inactivation of catalase from *Staphylococcus aureus* MF-31," Appl. Environ. Microbiol. 37(6):1180-85 (1979).
Averina et al., "Biomarkers and utility of the antioxidant potential of probiotic Lactobacilli and Bifidobacteria as representatives of the human gut microbiota," Biomedicines 9(10): 1340-73 (2021).
Bucker et al., "Superoxide dismutase activity in thermally stressed *Staphylococcus aureus*," Appl. Environ. Microbiol. 41(2): 449-54 (1981).
Grompone et al., "Anti-inflammatory Lactobacillus rhamnosus CNCM I-3690 strain protects against oxidative stress and increases lifespan in Caenorhabditis elegans," PLoS One 7(12): e52493, pp. 1-13 (2012).
Mates et al., "Antioxidant enzymes and human diseases," Clin. Biochem. 32(8): 595-603 (1999).
Tang et al., "PAMPs and DAMPs: signal 0s that spur autophagy and immunity" Immunol. Rev. 249(1): 158-75 (2012).
Elson et al., "Contribution of Toll-like receptors to the innate immune response to Gram-negative and Gram-positive bacteria," Immunobiology, 109(4): 1574-583 (2007).
"Opinion of the Scientific Committee on a request from EFSA on the introduction of a Qualified Presumption of Safety (QPS) approach for assessment of selected microorganisms referred to EFSA," The EFSA Journal, 587, 1-16 (2007).
Bulletin of the International Dairy Federation 455/2012, "Safety Demonstration of Microbial Food Cultures (MFC) in Fermented Food Products," International Dairy Federation, 1-68 (2012).
Herbert et al., "The Continuous Culture of Bacteria; a Theoretical and Experimental Study," J. Gen. Microbiol., 14(3):601-22 (1956).
Hyronimus et al., "Coagulin, a bacteriocin-like inhibitory substance produced by Bacillus coagulans I4," J. Appl. Microbiol., 85(1):42-50 (1998).
Lau et al., "Oral Application of Bacterial Lysate in Infancy Decreases the Risk of Infantile Atopic Eczema in a Subgroup of Children with Paternal Atopy," J. Allergy Clin. Immunol., 127(2):AB34 Abstract 119 (2011).
Mishra et al., "Probiotics as Potential Antioxidants: A Systematic Review," J. Agric. Food Chem., 63(14):3615-26 (2015).

* cited by examiner

CONTROL OF CELLULAR REDOX LEVELS

CROSS-REFERENCE TO RELATED APPLICATIONS

This application claims the benefit of U.S. Provisional Application No. 62/253,542, filed Nov. 10, 2015. This application is also a continuation-in-part of U.S. application Ser. No. 14/640,075, filed Mar. 6, 2015, which is a continuation of U.S. application Ser. No. 14/034,044, filed Sep. 23, 2013, which claims the benefit of U.S. Provisional Application No. 61/704,090, filed Sep. 21, 2012. This application is also a continuation-in-part of U.S. application Ser. No. 13/743,194, filed Jan. 16, 2013, which claims the benefit of U.S. Provisional Application No. 61/586,975, filed Jan. 16, 2012. All of the above-identified applications are hereby incorporated by reference in their entireties.

BACKGROUND

The innate immune response is one of the pathways that regulates inflammation. Inflammation is stimulated by chemical factors released by injured cells and serves to establish a physical barrier against the spread of infection, and to promote healing of any damaged tissue following the clearance of pathogens. The process of acute inflammation is initiated by cells already present in all tissues, mainly resident macrophages, dendritic cells, histiocytes, Kupffer cells, and mastocytes. These cells present receptors, contained on the surface or within the cell, named pattern recognition receptors (PRRs), which recognize molecular patterns that are broadly shared by pathogens but are distinguishable from those of the host. These molecular patterns are collectively referred to as pathogen-associated molecular patterns (PAMPs). Immune cells undergo activation when one of their PRRs recognizes a PAMP and in response release inflammatory mediators.

PAMPs are thus structures associated with groups of pathogens that are recognized by cells of the innate immune system. A vast array of different chemical types can serve as PAMPs, including glycans and glycoconjugates. These structures can also be referred to as small molecular motifs which are conserved within a class of microbes. They are recognized by Toll-like receptors (TLRs) and other PRRs in both plants and animals.

TLRs are conserved receptors that recognize structures from bacteria, fungi, protozoa, and viruses. Although the TLR receptor is located on the surface of the plasma membrane, binding to the receptor is transmitted transmembrane and results in an intercellular signaling response. TLR signaling ultimately leads to the induction or suppression of genes that orchestrate the inflammatory response. Activation of a particular TLR, for example, initiates a series of intracellular events resulting in an immune response characterized by the production of pro-inflammatory cytokines. TLR signaling originates from the cytoplasmic Toll-interleukin 1 (TIR) domain, conserved among all TLRs. The adapter molecule MyD88, containing both a TIR domain and a death domain, associates with the TIR domain of TLRs and IRAK proteins. Phosphorylation of IRAK leads to association with TRAF6 and subsequent activation of NF-κB and secretion of pro-inflammatory cytokines. A52R, an immunoregulatory protein from the vaccinia virus, has previously been shown to be an intracellular inhibitor of TIR-dependent signaling. When expressed in HEK293 cells, A52R was shown to inhibit NF-κB activation in response to stimulation by a variety of TLRs, including TLR4, TLR5, and the combination of TLR2 and 6, and TLR2 and 1. In addition, A52R inhibited NF-κB activation in response to Poly (1:0), a synthetic ligand for TLR3. TLR3 has been implicated in an anti-viral innate immune response.

One of the primary responses of activation is to shift the redox status of a cell. Reactive oxygen species (ROS) can be produced for defensive purposes. The very presence of ROS consumes antioxidants (reductants) and results in a more oxidative redox status. Not only can ROS and oxidative conditions result in cellular damage with concomitant activation of genes, redox status itself controls gene expression. For example, when conditions become more oxidative, easily oxidized chemical groups such as sulfhydryl groups on certain proteins become oxidized. The oxidized state of these proteins is then recognized, leading to activation of specific genes, such as genes controlling redox status and promoting or controlling inflammation, or genes producing aberrant or disease-promoting proteins.

Inflammation is part of the complex biological response of body tissues to harmful stimuli, such as pathogens, damaged cells, or irritants. Inflammation can also result from autoimmune disorders (where body tissues are incorrectly recognized as being foreign). Inflammation initially serves as a protective response that involves immune cells, blood vessels, and molecular mediators. One purpose of inflammation is to eliminate the initial cause of cell injury, clear out necrotic cells and tissues damaged from the original insult and the inflammatory process, and to initiate tissue repair. It is useful to differentiate inflammation from infection conceptually, as there are many pathological situations where inflammation is not driven by microbial invasion or infection, for example, atherosclerosis, type III hypersensitivity, trauma, and ischemia. There are also pathological situations where microbial invasion does not result in classic inflammatory response, for example, as in eosinophilia. Whereas too little inflammation could lead to progressive tissue destruction by the harmful "invaders" (e.g. bacteria, virus and mutated cells) and compromise the survival of the organism, too much inflammation (as in the case of chronic inflammation) may lead to a host of diseases, such as hay fever, periodontitis, atherosclerosis, rheumatoid arthritis, and even cancer (e.g., gallbladder carcinoma).

The initiation of a redox change and the resulting inflammatory response to pathogens is a critical component of the innate immune response designed to control infection. Because the sustained production of inflammatory mediators can lead to chronic inflammation, tissue damage and disease development, inflammation is normally closely regulated. The signaling cascade initiated by PAMP/TLR interactions and culminating in gene activation has been associated with many disease states, including sepsis, autoimmune diseases, asthma, heart disease and cancer. For example, it is hypothesized that sepsis occurs when bacteria and their products activate an uncontrolled network of host-derived mediators, such as pro-inflammatory cytokines which can lead to multi-organ failure, cardiovascular collapse and death. An abnormal TLR signaling response could lead to exaggerated cell-activation responses contributing to sepsis.

Inflammation (whether chronic or acute) results from and leads to the increased production and release of free radicals and other ROS from damaged and/or inflamed tissues and as a result contributes to or causes oxidative stress. At the same time, inflammation can result from oxidative stress when ROS damage tissues. As such, inflammation and the various conditions associated with it can also be regarded as an "oxidative stress-related disease or condition." Other stresses such as psychological stress can also lead to shifts in redox level and resulting oxidative stress and even inflammation. With such a positive feedback loop when the redox status induces a state of oxidative stress, that state may become self-perpetuating. Oxidative redox status and oxidative stress is supposed to occur in a defined locus and for a limited time. When the locus of the oxidative redox status is inappropriate and/or continues for too long, a pathological or disease state exists. A wide range of pathological or disease states are potentiated by inappropriate redox state or oxidative stress brought on by chronic or acute inflammation or vice versa.

Oxidative stress is a pathological form of an oxidative redox state involving the damaging action of abnormally increased amounts of ROS including free radicals. Free radicals are single atoms or molecules having at least one external electron orbital "occupied" by a single electron ("unpaired") instead of two electrons ("paired"). The existence of an unpaired electron makes free radical compounds exceptionally reactive. They may spontaneously react with, and thereby damage, a large variety of key cellular molecules. A certain number of ROS including free radicals are naturally produced by the body due to cell metabolism. For instance, the synthesis of some hormones involves the generation of free radicals while polymorphonuclear leukocytes use the production of free radicals as a form of "chemical warfare" to kill bacteria, thereby guarding the body against infections. Other free radicals, such as Nitric Oxide (NO) are fundamental for the homeostasis of the body, because they act as chemical messengers to modulate important functions, including vascular tone, platelet aggregation, cell adhesion, and so on.

Free radicals are potentially dangerous because they spontaneously tend to fill their unfilled external orbital with a second electron. The presence of two electrons in the same orbital is the condition of maximal stability—minimum energy. Therefore, when a free radical collides with a "target molecule", having one or more "available" electrons, such as the molecule of an unsaturated fatty acid (e.g., arachidonic acid), it immediately "extracts" an electron from the target molecule. Due to this effect—"oxidation"—the original free radical loses its potential dangerousness whilst the newly generated molecule is "oxidized" and, in turn, may become a new free radical, thus perpetuating the reaction, if no antioxidants are available to damp it. The reaction can continue to other molecules, including carbohydrates, lipids, amino acids, peptides, proteins, nucleotides, nucleic acids and so on ("chain reaction effect"). Such action by free radicals can result in varying degrees of tissue damage and can cause (or conversely result from) inflammatory responses. An initial or primary site of ROS release may be an appropriate response to an invading microorganism, but the invader is not destroyed or if redox homeostasis is not restored following destruction of the invader, the redox state may spread and the continuing secondary oxidative redox state may result in a chronic, damaging pathology with collateral tissue damage. An example would be traumatic brain injury (TBI) which leads to localized inflammation and oxidative redox status in the brain. If homeostasis is not reestablished, chronic oxidative redox status may result leading to long term tissue damage and chronic traumatic encephalopathy (CTE).

There thus exists a need in the art for compositions and methods for controlling cellular redox levels.

SUMMARY

The methods and compositions disclosed herein are not limited to specific advantages or functionality.

In one aspect, the disclosure provides toll-like receptor (TLR) agonist compositions for regulating redox status in a subject, the composition comprising: (a) a TLR agonist comprising at least one lysate and/or lysate fraction of a bacterium, wherein the TLR agonist activates at least one or more TLRs or NLRs; (b) an optional promoter for enhancing absorption of the composition; and (c) an optional carrier for increasing a volume of the composition, wherein administration of an effective amount of the composition to the subject measurably reduces oxidative stress levels in the subject.

In another aspect, the disclosure provides methods of regulating redox status in a subject, the method comprising administering a therapeutically effective amount of a lysate composition according to the disclosure to a subject in need thereof. In some embodiments, redox status regulation is assessed by measuring changes in isoprostane concentration in the subject.

In another aspect, the disclosure provides methods of regulating redox status in a subject, the method comprising the steps of: (a) repeatedly administering to a subject in need thereof doses spaced apart in time and consisting of a composition comprising: (i) a toll-like receptor (TLR) agonist comprising at least one lysate and/or lysate fraction of a bacterium, wherein the agonist activates at least one or more different TLRs or NLRs; (ii) an optional promoter for enhancing absorption of the composition; and (iii) an optional carrier for increasing a volume of the composition; and (b) making measurements of a bodily fluid of the subject to detect changes in oxidative stress levels.

In another aspect, the disclosure provides methods of decreasing the amount of isoprostane in the urine or blood of a subject, the method comprising the steps of: (a) determining the level of isoprostane in the urine or blood of the subject; (b) administering to the subject an effective amount of a composition comprising: (i) a toll-like receptor (TLR) agonist comprising at least one bacterial lysate and/or lysate fraction from a bacterium, wherein the TLR agonist activates at least one or more different TLRs or NLRs; and (ii) an optional promoter for enhancing absorption of the composition; and (c) continuing administration of the composition until the level of isoprostane in the urine or blood of the subject is decreased.

In another aspect, the disclosure provides compositions comprising: (a) a bacterial lysate and/or lysate fraction capable of activating at least one or more toll-like receptors (TLRs) or Nod-like receptors (NLRs); (b) an optional promoter for enhancing absorption of the composition; and (c) an optional carrier for increasing a volume of the composition.

In another aspect, the disclosure provides pharmaceutical formulations comprising lysate compositions according to the disclosure, wherein the pharmaceutical formulation is formulated for buccal or sublingual administration. In some embodiments, the pharmaceutical formulations are formulated to dissolve in not less than 1 minute after administration.

In another aspect, the disclosure provides methods of producing a bacterial lysate comprising the steps of: (a) fermenting a bacterium in a growth medium to the stationary growth phase to produce a fermentation broth; (b) harvesting bacteria from the fermentation broth; (c) pasteurizing the harvested bacteria; and (d) lysing the pasteurized bacteria with a lysozyme to produce a bacterial lysate. In some embodiments, the bacteria are harvested in the mid-logarithmic phase, the late-logarithmic phase, the early stationary phase, the mid-stationary phase, or the late stationary phase.

In another aspect, the disclosure provides bacterial lysates produced according to methods comprising the steps of: (a) fermenting a bacterium in a growth medium to the stationary growth phase to produce a fermentation broth; (b) harvesting bacteria from the fermentation broth; (c) pasteurizing the harvested bacteria; and (d) lysing the pasteurized bacteria with a lysozyme to produce a bacterial lysate. In some embodiments, the bacteria are harvested in the mid-logarithmic phase, the late-logarithmic phase, the early stationary phase, the mid-stationary phase, or the late stationary phase.

In another aspect, the disclosure provides methods for alleviating one or more oxidative stress-related side effects associated with administration of a pharmaceutical agent, the method comprising administering in combination with the pharmaceutical agent a therapeutically effective amount of a lysate composition comprising: (a) a lysate and/or lysate fraction of a bacterium; (b) an optional promoter for enhancing absorption of the composition; and (c) an optional carrier for increasing a volume of the composition; wherein the pharmaceutical agent and lysate composition are administered simultaneously or in any order, and through the same or different routes of administration.

In another aspect, the disclosure provides methods for treating oxidative stress-related diseases or conditions in a subject, the method comprising administering to the subject a therapeutically effective amount of a composition comprising: (a) a bacterial lysate and/or lysate fraction capable of activating at least one or more toll-like receptors (TLRs) or Nod-like receptors (NLRs); (b) an optional promoter for enhancing absorption of the composition; and (c) an optional carrier for increasing a volume of the composition.

In another aspect, the disclosure provides methods for reducing oxidative stress in a subject, the method comprising: (a) determining the level of oxidative stress in the subject by measuring the amount of isoprostane in the urine or blood of the subject; (b) administering to the subject an effective amount of a composition comprising: (i) a toll-like receptor (TLR) agonist comprising at least one lysate and/or lysate fraction from a bacterium, wherein the TLR agonist activates at least one or more TLRs or NLRs; and (ii) an optional promoter for enhancing absorption of the composition; and (c) continuing administration of the composition until the level of oxidative stress is reduced, as determined by a decreased amount of isoprostane in the urine of the subject.

In another aspect, the disclosure provides therapeutic combinations comprising: (a) a lysate composition comprising (i) a bacterial lysate and/or lysate fraction capable of activating at least one or more toll-like receptors (TLRs) or Nod-like receptors (NLRs); (ii) an optional promoter for enhancing absorption of the composition; and (iii) an optional carrier for increasing a volume of the composition; and (b) one or more pharmaceutical agents; wherein the lysate composition and the one or more pharmaceutical agents are administered simultaneously or in any order, and wherein the lysate composition and the one or more pharmaceutical agents are administered via the same or different routes of administration.

In another aspect, the disclosure provides pharmaceutical formulations comprising the combination of: (a) a lysate composition comprising (i) a bacterial lysate and/or lysate fraction capable of activating at least one or more toll-like receptors (TLRs) or Nod-like receptors (NLRs); (ii) an optional promoter for enhancing absorption of the composition; and (iii) an optional carrier for increasing a volume of the composition; and (b) one or more pharmaceutical agents. In some embodiments, the one or more pharmaceutical agents are selected from the group consisting of: an antispasmodic, a motility stimulant, an H2-Receptor antagonist, antimuscarinic; a chelate, a prostaglandin analog, an aminosalicylate, a corticosteroid, an drug affecting immune response, a stimulant laxative, a drug affecting biliary composition and flow, a bile acids sequestrant, a dopamine antagonist, a proton pump inhibitor, an opioid, an opioid receptor antagonist, an analgesic, a sleep drug, a cardiac glycoside, a phosphodiesterase inhibitor, a thiazide, a diuretic, a potassium sparing diuretic, an aldosterone antagonist, an osmotic diuretic, a drug for arrhythmia, a beta adrenoreceptor blocking drug, a hypertension drug, a drug affecting the renin-angiotensin system, a nitrate, a calcium blocker, an antianginal drug, a peripheral vasodilator, a sympathomimetic, an anticoagulant, a protamine, an antiplatelet drug, a fibrinolytic drug, an antifibrinolytic drug, a lipid regulating drug, an omega three fatty acid compound, a CNS drug, an anti-infective, or another drug selected from the group consisting of Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, and Interferon Beta.

In another aspect, the disclosure provides formulations comprising (a) a lysate composition comprising (i) a bacterial lysate and/or lysate fraction capable of activating at least one or more toll-like receptors (TLRs) or Nod-like receptors (NLRs); (ii) an optional promoter for enhancing absorption of the composition; and (iii) an optional carrier for increasing a volume of the composition; and (b) an isolated human anti-TNFalpha antibody or antigen-binding fragment thereof or TNF inhibitor. In some embodiments, the human anti-TNFalpha antibody or antigen-binding fragment thereof is adalimumab. In another aspect, the disclosure provides uses of such formulations in the manufacture of a medicament for the treatment of rheumatoid arthritis (RA), late-onset RA, or psoriatic arthritis in a subject. In another aspect, the disclosure provides methods for the treatment of rheumatoid arthritis (RA), late-onset RA, or psoriatic arthritis in a subject, the method comprising administering to the subject a therapeutically effective amount of such formulations.

In some embodiments of any of the methods or compositions disclosed herein, the bacterium is a Gram-positive or Gram-negative bacterium. In some embodiments of any of the methods or compositions disclosed herein, the Gram-positive bacterium is selected from the group consisting of a bacterium of Lactobacillaceae family, a bacterium of Streptococcaceae family, a bacterium of Bifidobacteriaceae family, and a bacterium of Bacillaceae family. In some embodiments, the Gram-positive bacterium is selected from the group consisting of *Bacillus coagulans, Lactobacillus sporogenes, Streptococcus thermophilus, Bifidobacterium animalis, Bifidobacterium. animalis*, subspecies *animalis*,

*Bifidobacterium infantis, Bifidobacterium longum, Bifidobacterium breve, Lactobacillus acidophilus, Lactobacillus plantarum, Lactobacillus casei, Lactobacillus delbrueckii, Lactobacillus delbrueckii* subspecies *bulgaricus, Lactococcus lactis, Lactococcus lactis* subspecies *lactis, Streptococcus lactis, Streptococcus thermophilus, Bifidobacterium lactis, Bifidobacterium breve, Pediococcus acidilactici*, and *Lactobacillus helveticus.*

In some embodiments of any of the methods or compositions disclosed herein, the Gram-negative bacterium is selected from the group consisting of a bacterium of *Pseudomonas* genus, *Klebsiella* genus, *Xanthomonas* genus, *Shigella* genus, and *Enterobacter* genus. In some embodiments, the Gram-negative bacterium is selected from the group consisting of *Klebsiella oxytocia, Shigella flexneri, Xanthomonas campestris*, and *Pseudomonas flourescens.*

In some embodiments of any of the methods or compositions disclosed herein, the TLR agonist, lysate, lysate fraction, or cell wall fraction activates at least one or more of TLR 2, TLR 3, TLR 4, TLR 5, TLR 7, TLR 8, TLR 9, NOD1, and NOD2. In some embodiments, the TLR agonist, lysate, lysate fraction, or cell wall fraction activates two or more of TLR 2, TLR 3, TLR 4, TLR 5, TLR 7, TLR 8, TLR 9, NOD1, and NOD2. In some embodiments, the TLR agonist, lysate, lysate fraction, or cell wall fraction activates TLR 2 and TLR 4. In some embodiments, the TLR agonist, lysate, lysate fraction, or cell wall fraction activates three or more of TLR 2, TLR 3, TLR 4, TLR 5, TLR 7, TLR 8, TLR 9, NOD1, and NOD2.

In some embodiments of any of the methods or compositions disclosed herein, the promoter is selected from the group consisting of amino acids, amino sugars, and sugars. In some embodiments, the carrier is selected from the group consisting of a binder, a gum base, and combinations thereof. In some embodiments, the gum base comprises at least one hydrophobic polymer and at least one hydrophilic polymer. In some embodiments, the binder is selected from the group consisting of a sugar, a sugar alcohol, and combinations thereof. In some embodiments, the sugar alcohol is selected from the group consisting of mannitol, sorbitol, xylitol, and combinations thereof.

In some embodiments, the compositions are manufactured as a dosage form selected from the group consisting of a lozenge, a chewing gum, a chewable tablet, a candy, and a dissolving tablet. In some embodiments, the dosage form delivers the TLR agonist to an oral mucosa. In some embodiments, the oral mucosa is selected from the group consisting of the sublingual mucosa, buccal mucosa, and a combination thereof.

In some embodiments of any of the methods and compositions disclosed herein, the compositions are formulated for oral mucosal delivery; in some embodiments, the compositions are formulated for sublingual or buccal delivery. In some embodiments, the compositions are formulated to dissolve in not less than 1 minute after administration.

These as well as other aspects, advantages, and alternatives, will become apparent to those of ordinary skill in the art by reading the following detailed description, with reference where appropriate to the accompanying drawings, and taken together with the accompanying claims.

DETAILED DESCRIPTION

Figure 1:
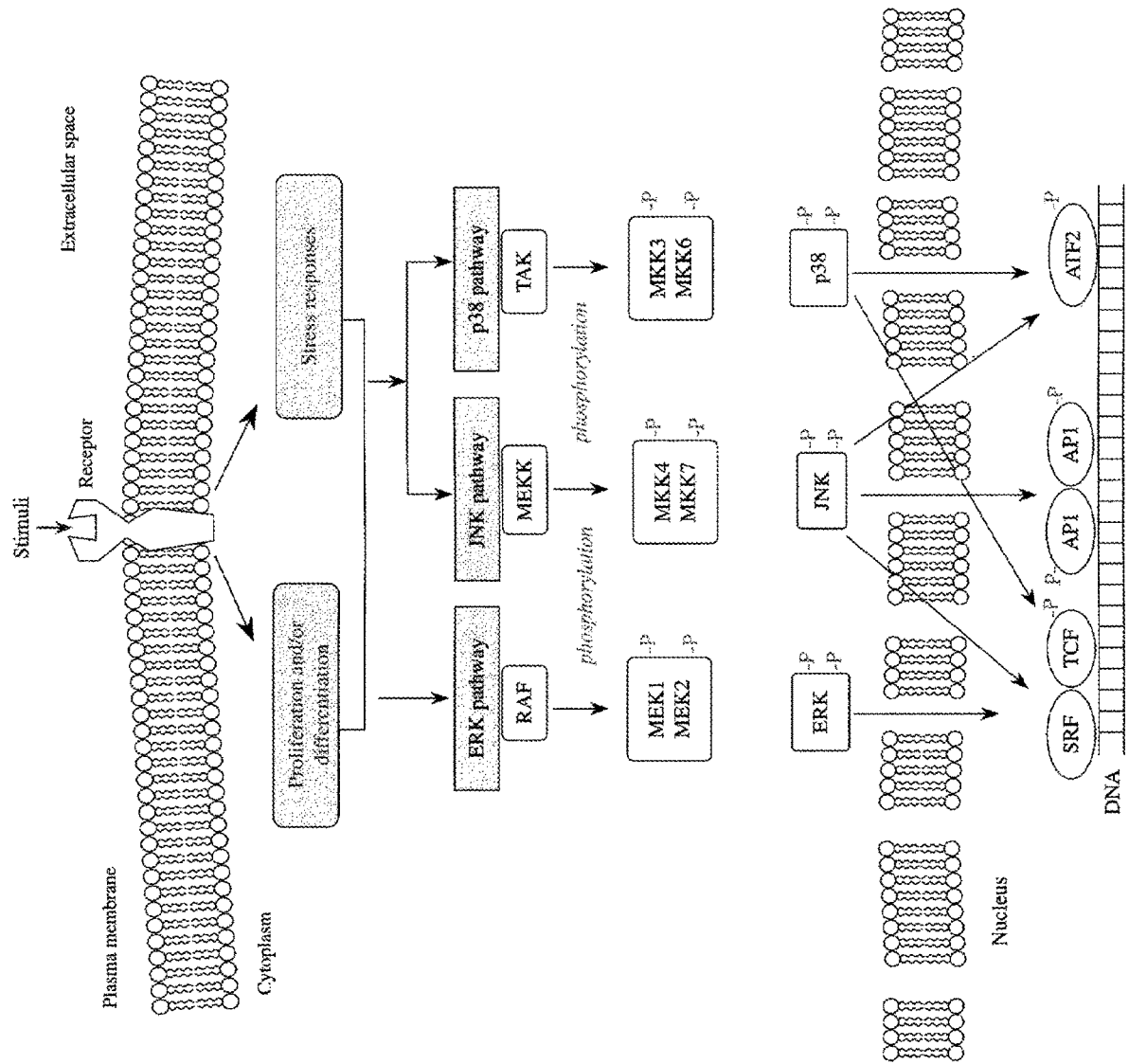
FIG. 1 shows a diagrammatic representation of a toll-like receptor (TLR) showing various response pathways.

All publications, patents and patent applications cited herein are hereby expressly incorporated by reference for all purposes.

Cellular redox (oxidation-reduction) state varies widely. Oxidation and reduction reactions are key to cellular bioenergetics. Normally when oxidation of food molecules results in electron transport and ultimate capture of energy as energy rich molecules such as NADP (nicotinamide adenine dinucleotide phosphate) and ATP (adenosine triphosphate), TLRs are activated in such a manner such that downstream oxidation/reduction reactions are balanced. As used herein, the term "balance" refers to a homeostatic balance; that is, not necessarily a situation in which the amount of oxidation equals the amount of reduction in a given system, but rather where oxidation and reduction are in immunologic and thus metabolic homeostasis for the host. However, there are a number of cellular situations where the redox state changes. Usually, the cell is armed with antioxidant molecules, but where such molecules become depleted, the redox status of the cell changes. One likely cause for this is the purposeful production of reactive oxygen species (ROS) such as $O2^-$ (superoxide radical), OH (hydroxyl radical) and $H_2O_2$ (hydrogen peroxide) for defensive or similar purposes. When the redox balance is shifted, oxidative stress may ensue. Oxidative stress is a pathological condition triggered by the damaging action—on the cells and tissues of the body—of abnormally increased levels of ROS. Oxidative stress is the direct consequence of an increased, immunologically uncontrolled generation of ROS and/or a reduced physiological activity of antioxidant defenses against excess ROS. Inflammation (whether chronic or acute) as well as other stresses and infection can lead to the increased production and release of ROS from damaged and/or inflamed tissues thereby shifting the redox balance of the cell and as a result contribute to oxidative stress. At the same time, inflammation can result from oxidative stress as ROS damage tissues. A wide range of diseases and disease states are associated with changes in redox state and oxidative stress brought on by chronic or acute inflammation or vice versa. Current therapies for treating chronic or acute inflammation do not come without harmful side effects. Described herein are compositions and methods for altering redox levels in the treatment of oxidative stress and related conditions.

Before describing the disclosed methods and compositions in detail, a number of terms will be defined. As used herein, the singular forms "a", "an" and "the" include plural referents unless the context clearly dictates otherwise. For example, reference to "nucleic acid" means one or more nucleic acids.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As described above, pathogen-associated molecular patterns (PAMPs) can activate innate immune responses by stimulating TLRs, which generally are activated by conserved non-self biochemical structures, thus protecting a host from infection. Bacterial lipopolysaccharide (LPS) is found on the bacterial cell membrane of some bacteria, and is considered to be the prototypical PAMP. LPS is specifically recognized by TLR4, a recognition receptor of the innate immune system. Other PAMPs include bacterial flagellin (recognized by TLR5), lipoteichoic acid, peptidoglycan, and nucleic acid variants normally associated with viruses, such as double-stranded RNA (dsRNA), recognized by TLR3 or unmethylated CpG motifs, recognized by TLR9.

In some cases, however, PAMPs reduce inflammation. EPS (exo-polysaccharide), a material that typically stimulates an immune response, has been shown to stimulate negative regulators of TLRs, thus leading to a reduced inflammatory response. More specifically, EPS has been shown to stimulate expression of immunoglobin IL-1 related receptor, toll interacting protein, B-cell lymphoma 3-encoded protein, A20, mitogen-activated protein kinase phosphate-1, and interleukin associate kinase M, and has been shown to lead to the negative regulation of TLRs and inflammation.

These seemingly contradictory effects of PAMPs are at least partly explained by the innate immune system's interaction with the microbiome. The immune system does not exist in a vacuum. Even when an organism has no active inflammatory responses taking place, immune cells are responding to an onslaught of PAMPs from the environment—particularly from the microbiome. Given the various TLR receptors that are activated are producing a downstream redox state that is in immunologic and metabolic homeostasis, the system issues an "All Clear" signal to avoid inadvertent responses which might damage the essential microbiome constituents. Hence, presenting the right combination of PAMPs to the cells of the innate immune system can control the entire redox system, down-regulating or up-regulating it to achieve, or in some cases restore, immunologic and metabolic homeostasis.

FIG. 1 shows a diagrammatic representation of a transmembrane a TLR. Although the ligand accepting (stimuli) portion of the molecule is located on the surface of the plasma membrane, the transmembrane domain of the protein is able to conduct signal to the cytoplasmic surface of the membrane through conformational changes that occur when a ligand is bound. At the cytoplasmic surface this signal (arrows) is coupled to a number of different signaling pathways. Proliferation/differentiation and stress-response pathways are shown. Note that one TLR type does not simultaneously control both pathways as in this generalized diagram. Rather some TLRs control one pathway or set or pathways and other TLRs control a different pathway or set of pathways. In addition, it is likely that one type of TLR controls different pathways depending on which cell type it is located in; thus, delivering the correct balance of TLR agonists is important for maintaining homeostasis.

The downstream signaling mechanisms may be shared to a greater or lesser extent. In FIG. 1, the proliferation response largely uses the ERK pathway whereas the stress response uses the MEKK and TAK pathways. In each pathway, signal molecules are phosphorylated and there can be a phosphorylation cascade to amplify the signal. Ultimately the phosphorylated protein enters the nucleus (through the nuclear pores) where the phosphorylate intermediates alter both transcription and translation. In this way, TLRs are able to control entire suites of genes. In all, thousands of genes are activated by TLR signaling, and collectively, the TLRs constitute one of the most pleiotropic yet tightly regulated gateways for gene modulation.

One of the primary responses of TLR activation is to shift the downstream redox status of the cell when warranted. The initiation of a redox change and the resulting inflammatory response to pathogens is a critical component of the innate immune response designed to control infection. Inflammation (whether chronic or acute) results from and leads to the increased production and release of free radicals and other ROS from damaged and/or inflamed tissues and as a result contributes to or causes oxidative stress. At the same time, inflammation can result from oxidative stress when ROS damage tissues. As such, inflammation and the various conditions associated with it can also be regarded as an "oxidative stress-related disease or condition."

Oxidative stress, being a biochemical condition, generally does not exhibit any specific clinical symptoms or clinical signs apart from the specific pathological conditions it induces. It may generally remain undiscovered, with concomitant damage to the patient, until a clinician suspects its existence and decides to assay for oxidative stress.

Various common diseases and/or conditions are frequently associated with oxidative stress. One example is Alzheimer's disease. Studies have shown that chronic oxidative stress increases the levels of tau phosphorylation, a known biomarker of Alzheimer's disease. Studies have also shown that oxidative stress results in tau-induced neurodegeneration in models of Alzheimer's disease.

Other known "oxidative stress-related diseases or conditions" include, but are not limited to: aceruloplasminemia, acute and chronic alcoholic liver diseases, acute autoimmune myocarditis, acute chest syndrome of sickle cell disease, acute pancreatitis, acute respiratory distress syndrome, alcoholic liver disease, Amyotrophic Lateral Sclerosis, arterial/systemic hypertension, asbestosis, asthma, ataxia telangiectasia, atherosclerosis, atopic dermatitis, brain ischemia, bronchopulmonary dysplasia, burns, some cancers, cardiopulmonary bypass, cardiovascular diseases, cataract, cellulitis, chemotherapeutic side-effect, chronic fatigue syndrome, chronic Hepatitis C, chronic kidney disease, chronic obstructive pulmonary disease, chronic renal failure, colitis, coronary artery disease, Creutzfeldt-Jakob disease, Crohn's disease, cutaneous leishmaniasis, cystic fibrosis, diabetes mellitus type 1, diabetes mellitus type 2, dyslipidemia, Down's syndrome, eclampsia, end-stage renal disease, erectile dysfunction, Friedreich ataxia, headache, heart failure, *Helicobacter pylori* infection/inflammation, hemodialysis side effects, hepatic cirrhosis, Human Immunodeficiency Virus infection, Huntington disease, hyperbaric diseases, hypercholesterolemia, hyperhomocysteinemia, hyperlipidemia, idiopathic pulmonary fibrosis, interstitial lung disease, ischemia/reperfusion injury, juvenile chronic arthritis, kidney transplantation failure, leukemia, lung cancer, lung injury, macular degeneration, male infertility, Ménière's syndrome, meningitis, mild cognitive impairment, Multiple Sclerosis, myelodisplastic syndromes, myocardial infarction, myocarditis, neonatal bronchopulmonary dysplasia, obesity, osteoarthritis, osteoporosis, pancreatitis, Parkinson's disease, periodontal disease, peritoneal dialysis side effects, photoageing, post-traumatic stress disorder, preeclampsia, primary biliary cirrhosis, broncopulmonary diseases, progeria, psoriasis, psoriatic arthritis, pulmonary hypertension, radio-therapy side effects, reactive arthritis, renal cell carcinoma, respiratory distress syndrome, retinopathy of prematurity, retrolenticolar fibroplasy, rheumatic disease, rheumatoid arthritis, sarcoidosis, sepsis, sickle cell disease, sleep apnea, spherocytosis, spinal cord injury, stroke, synucleinopathies, systemic amyloidosis, systemic lupus erythematosus, systemic sclerosis (scleroderma), thrombophily, tauopathies, traumatic stress tubercolosis, unstable angina, uremia, venous insufficiency, Werner syndrome, and Zellweger syndrome.

Oxidative stress mediates the pathological symptoms of a great many disorders and control of redox levels, and control of redox levels, and hence oxidative stress, will prevent much tissue damage thereby allowing more ready control of the underlying disease where reducing oxidative stress is not sufficient to achieve control of the disease. For example, myocardial infarction is death or damage to heart muscle caused by a vascular blockage. Leaving aside the possible role for oxidative stress in causing vascular blockages, once a blockage has occurred, the affected muscles cells become anoxic and ultimately die. However, if the blockage is rapidly reversed (e.g., by "clot busting" drugs), circulation is restored and, in theory, the affected muscle cells will be saved. However, in many cases, the initial injury provokes an inflammatory response resulting in oxidative stress and muscles cell damage in spite of the prompt restoration of circulation. Controlling this oxidative stress can virtually eliminate damage to the heart muscle cells. In all of these diseases and disorders, regulation of oxidative stress might alleviate or treat the symptoms and/or causes of the disease or disorder.

Changes in redox status can result in oxidation of sulfhydryl groups on key proteins, but these proteins, themselves, are often difficult to measure. However, increased oxidative stress or redox change, either chronic or acute, can and will alter a number of other cellular constituents either by the previously mentioned oxidation of sulfhydryl groups or by other chemical oxidative mechanisms, such as peroxidation, that result in the transfer of electrons.

Isoprostanes are prostaglandin-like compounds formed in vivo from the free radical-catalyzed peroxidation of essential fatty acids (primarily arachidonic acid) without the direct action of cyclooxygenase (COX) enzymes, which are the normal mechanism of prostaglandin formation. These compounds possess potent biological activity as inflammatory mediators that augment the perception of pain. These molecules are controlled by at least two different pathways. One pathway is mediated by COX enzymes that transform lipids into isoprostanes in response to gene activation and signal molecules. In the alternate pathway, lipids are directly oxidized into isoprostanes in response to a high oxidative redox status. Because isoprostanes are mediators of inflammation they form part of the positive feedback loop that can maintain damaging oxidative redox status.

Isoprostanes, such as F2-isoprostanes, are thus accurate markers of oxidative redox status in both animal and human models of oxidative stress, and measurement of isoprostanes has emerged as one of the most reliable approaches to assess oxidative stress in vivo due to their inherit stability and their ease of measurement in bodily fluids such as urine and blood. This ease and stability has made measurement of isoprostanes an important and reliable tool to explore the role of oxidative stress in the pathogenesis of human disease. Isoprostane levels are directly correlated with oxidative redox status and resulting oxidative stress. Even if the site of oxidative redox status is limited in extent, isoprostanes generated there can be measured in bodily fluids, e.g., urine, remote from the site of oxidative stress and resultant inflammation.

Other biological compounds that could be oxidized include, but are not limited to, proteins, metalloproteins, enzymes, lipids, fatty acids, carbohydrates, neurotransmitters, DNA, vitamins, polyphenols, antioxidants, and coenzymes. Thus, constituents such as, but not limited to, superoxide dismutase (SOD), peroxidases, glutathione, as well oxidized forms of cellular constituents due to exposure to reactive species such as, but not limited to, advanced oxidized proteins, malondiadehyde, 8-hydroxydeoyguanosine, are other potential biomarkers for oxidative stress.

Given the importance of inflammation in the immune response and the harmful consequences it can cause via oxidative stress, oxidative stress-related diseases or conditions and/or other processes, it is important that an organism maintain close control of redox status. Also, given the intertwined relationship between oxidative stress and inflammation, biomarkers that measure inflammation have been proposed as indirect biomarkers of oxidative stress. These biomarkers, such as but not limited to C-reactive protein, serum amyloid A, and cytokines, are limited in their ability to pick up low grade changes in inflammation and consequently limited in their ability to pick up low grade redox changes. An alternative is to focus on biomarkers, such as isoprostanes, to measure redox status, and mechanisms to alter redox status.

Redox can be changed either by increasing reducing species (antioxidants) or by decreasing oxidants. There has been little success in controlling harmful redox levels through added antioxidants or antioxidant therapy (see Ho et al, Biological markers of oxidative stress: Applications to cardiovascular research and practice. 2013 Redox Biology). There is evidence for the long term use of dietary antioxidants—perhaps as preventative agents. However, when the immune system is not able to achieve or maintain homeostatic redox levels, added antioxidants are generally ineffective at correcting the balance.

An alternative route to affecting redox status is to aim at downstream targets; such strategies include the use of aspirin and glucocorticoids to block NF-κB activation and the targeting of specific inflammatory mediators such as TNF-α. Given their role in mediating the innate immune response and inflammation, TLRs present another target for controlling the innate and inflammatory responses.

As discussed above, TLRs help mediate the innate immune response by inducing or suppressing genes that orchestrate the inflammatory reaction. TLRs recognize and respond to a variety of signals. These signals bind to specific TLRs to promote or block signal pathways that can induce or suppress genes mediating inflammation. By targeting specific TLRs with specific agents, immune responses and inflammatory possesses can be mediated.

Inhibition of multiple TLR-dependent responses or activation of specific ones by targeting a common signaling component, may prove to be an effective approach to controlling an inflammatory response. Accordingly, compositions disclosed herein may be used to treat an oxidative stress disorder associated with a TLR-signaling pathway (e.g., TLR-induced inflammation), the method comprising the administration of a therapeutically effective amount of a composition as described herein, wherein the TLR affected is one or more of TLR2, TLR4, TLR5, TLR7 and TLR9.

As used herein, the term "therapeutically effective amount" refers to an amount administered to a subject that is sufficient to cause a desired effect in the subject.

As used herein, the terms "pharmaceutical formulation" and "pharmaceutical composition" refer to a preparation which is in such form as to permit a biological activity of an active ingredient to be effective, and which contains no additional components which are unacceptably toxic to a subject to which the formulation would be administered. The terms "the product," "the supplement," and "the composition" are used herein interchangeably in reference to pharmaceutical compositions comprising bacterial lysates, lysate fractions, and/or cell wall fractions of the disclosure.

Compositions described herein can be modified to target individual TLRs or groups of TLRs. By targeting individual TLRs or groups of TLRs, compositions described herein can be used to mediate instances of acute or chronic inflammation. In addition, compositions described herein can be used to curb instances of aberrant inflammation and restore healthy levels of inflammation.

Thus, described herein are compositions and methods for regulating oxidative stress. The compositions are able to activate various TLRs as assessed by measuring NF-κB expression in a variety of cell lines. The compositions described herein can also reduce or downregulate the activity of TLRs thus leading to reduced or regulated levels of inflammation. When the proper balance of TLR activation is achieved, cellular redox status is optimized and oxidative stress is reduced. This can be achieved by providing compositions containing PAMPs that simultaneously bind to two or more different types of TLRs.

In some cases a lysate of a single type of microorganism can act as an agonist to two or more TLRs. As disclosed herein, the precise manner of processing a microorganism lysate can affect which TLRs are stimulated by the lysate. In some embodiments, activation of a panel of TLRs may be accomplished by combining different lysates or fractions from a single type of microorganism or lysates or fractions from more than type of microorganism.

There are many different but similar PAMPs that bind to a given TLR type, albeit with different affinities. There are also PAMP molecules that stimulate an entirely different TLR type. How the lysate or fraction is processed can affect the PAMP assemblage present in the final product. Thus, different types of microorganisms present different palettes of PAMPs with which to work. As is disclosed herein, providing a composition that simultaneously stimulates (acts as an agonist for) particular TLR types results in dramatic downregulation of oxidative stress.

Unexpectedly, stimulating TLRs does not necessarily lead to an increase in oxidative stress. Rather, constant stimulation of TLRs by the microbiome is the normal situation and does not result in improper redox status and oxidative stress. Part of the explanation may be related to the location of a given TLR receptor as well as the type of the TLR receptor. Activation of TLR receptors located on mucosa gives a different result than activation of the same types of TLR receptors located in interior tissues of the body. Without being bound to a particular explanation or mechanism, the disclosure provides methods of applying or augmenting the normal microbiome signal, which reasserts homeostasis and "resets" the overall system by interrupting the positive feedback loop that powers abnormal redox status and oxidative stress.

The therapeutically active compositions of the present disclosure include a non-synthetic biologically active agent, preferably one or more cell wall fractions of one or more microorganisms including Gram-positive bacteria, Gram-negative bacteria, or combinations thereof, such as in the form of a lysate, along with a promoter, and optionally, one or more other additives, including control-release ingredients, so as to allow the composition to be absorbed into, or interact with, a mucosal wall of a subject in need of therapy.

As used herein, the terms "dose" and "dosage" shall encompass bolus or loading dose, and also encompass chronic or maintenance dosing. According to the present invention, the active therapeutic agent is a lysate, lysate fraction, or cell wall fraction of a bacterium, such as a Gram-positive bacterium or a Gram-negative bacterium in an amount ranging from about 0.01 mg therapeutic agent per kilogram of body weight to about 100 mg per kilogram body weight, as required to act as agonists for two of more TLRs depending upon the specific therapeutic application. In some embodiments, the active therapeutic agents of the disclosure are administered in a dosage of from about 0.01 mg therapeutic agent per kg body weight to about 10 gm therapeutic agent per kg body weight. In some embodiments, the active therapeutic agents of the disclosure are administered in a dosage of from about 0.01 mg therapeutic agent per kg body weight to about 1 gm therapeutic agent per kg body weight. In some embodiments, the active therapeutic agents of the disclosure are administered in a dosage of from about 0.01 mg therapeutic agent per kg body weight to about 50 mg therapeutic agent per kg body weight. In some embodiments, the active therapeutic agents of the disclosure are administered in a dosage of from about 0.05 mg therapeutic agent per kg body weight to about 30 mg therapeutic agent per kg body weight. In some embodiments, the active therapeutic agents of the disclosure are administered in a dosage of from about 0.05 mg therapeutic agent per kg body weight to about 5 mg therapeutic agent per kg body weight. In some embodiments, the active therapeutic agents disclosed herein are administered in a dosage of about 0.1 mg therapeutic agent per kg body weight, or of about 0.2 mg therapeutic agent per kg body weight, or of about 0.3 mg therapeutic agent per kg body weight, or of about 0.4 mg therapeutic agent per kg body weight, or of about 0.5 mg therapeutic agent per kg body weight, or of about 0.6 mg therapeutic agent per kg body weight, or of about 0.7 mg therapeutic agent per kg body weight, or of about 0.8 mg therapeutic agent per kg body weight, or of about 0.9 mg therapeutic agent per kg body weight, or of about 1 mg therapeutic agent per kg body weight, or of about 2 mg therapeutic agent per kg body weight, or of about 3 mg therapeutic agent per kg body weight, or of about 4 mg therapeutic agent per kg body weight, or of about 5 mg therapeutic agent per kg body weight, or of about 6 mg therapeutic agent per kg body weight, or of about 7 mg therapeutic agent per kg body weight, or of about 8 mg therapeutic agent per kg body weight, or of about 9 mg therapeutic agent per kg body weight, or of about 10 mg therapeutic agent per kg body weight. In some embodiments, the above dosages describe the total amount of active ingredient administered per day to a subject, wherein the total amount may be divided among two or more administrations per day, or may be the amount administered in a single daily dosage.

As used herein, the terms "therapeutic agent" and "active ingredient" refer to a lysate, lysate fraction, and/or cell wall fraction of the disclosure, or a combination thereof, as opposed to the non-active ingredients in in a composition or formulation.

In some embodiments, the pharmaceutical compositions disclosed herein are administered in formulations, such as in oral formulations, including tablet formulations, comprising from about 0.01 mg to about 10 gm active ingredient per dose, or of from about 0.5 mg to about 50 mg active ingredient per dose, or of from about 3 mg to about 30 mg active ingredient per dose, or of from about 10 to about 30 mg active ingredient per dose. In some embodiments, the pharmaceutical formulations are formulated and/or administered with about 0.5 mg, or about 1 mg, or about 5 mg, or about 10 mg, or about 15 mg, or about 20 mg, or about 25 mg, or about 30 mg active ingredient per dose. In some embodiments, the pharmaceutical compositions of the disclosure are formulated as tablets, with each tablet comprising about 0.5 mg to about 30 mg active ingredient per tablet. In some embodiments, the tablets each comprise about 0.5 mg active ingredient. In some embodiments, the tablets each comprise about 1 mg active ingredient. In some embodiments, the tablets each comprise about 5 mg active ingredient. In some embodiments, the tablets each comprise about 10 mg active ingredient. In some embodiments, the tablets each comprise about 15 mg active ingredient. In some embodiments, the tablets each comprise about 25 mg active ingredient. In some embodiments, the tablets each comprise about 40 mg active ingredient. In some embodiments, the tablets each comprise about 50 mg active ingredient. In some embodiments, the tablets each comprise about 1 gm active ingredient. In some embodiments the tablets each comprise about 10 gm active ingredient.

In some embodiments the pharmaceutical formulations of the disclosure are administered from one time per day to three times per day. In some embodiments, the pharmaceutical formulations of the disclosure are administered once per day. In some embodiments, the pharmaceutical formulations of the disclosure are administered two times per day. In some embodiments, the pharmaceutical formulations of the disclosure are administered three times per day.

In some embodiments, the pharmaceutical formulations are administered at a dosage level and frequency such that the subject receives a total of from about 0.01 mg to about 10 gm of active therapeutic agent per day, or a total of from about 1 mg to about 1 gm of active therapeutic agent per day, or a total of from about 5 mg to about 1 gm of active therapeutic agent per day, or a total of from about 5 mg to about 500 mg active therapeutic per day, or a total of from about 12 to about 375 mg per day. In some embodiments, the pharmaceutical formulations of the disclosure are administered at a dosage level and frequency such that the subject receives a total of about 1 mg, or about 2 mg, or about 3 mg, or about 4 mg, or about 5 mg, or about 6 mg, or about 7 mg, or about 8 mg, or about 9 mg, or about 10 mg, or about 11 mg, or about 12 mg, or about 13 mg, or about 14 mg, or about 15 mg active ingredient (i.e., lysate, lysate fraction, and/or cell wall fraction, or combination thereof) per day, or more as needed. In some embodiments, the pharmaceutical formulations of the disclosure are administered at a dosage level and frequency such that the subject receives a total of about 12 mg, or about 24 mg, or about 36 mg, or about 48 mg, or about 60 mg, or about 72 mg, or about 84 mg, or about 96 mg, or about 108 mg, or about 120 mg, or about 132 mg, or about 144 mg, or about 156 mg, or about 168 mg, or about 180 mg active ingredient (i.e., lysate, lysate fraction, and/or cell wall fraction, or combination thereof) per day, or more as needed. In some embodiments, the pharmaceutical formulations of the disclosure are administered at a dosage level and frequency such that the subject receives a total of about 15 mg, or about 30 mg, or about 45 mg, or about 60 mg, or about 75 mg, or about 90 mg, or about 105 mg, or about 120 mg, or about 135 mg, or about 150 mg, or about 165 mg, or about 180 mg, or about 195 mg, or about 210 mg, or about 225 mg active ingredient (i.e., lysate, lysate fraction, and/or cell wall fraction, or combination thereof) per day, or more as needed. In some embodiments, the pharmaceutical formulations of the disclosure are administered at a dosage level and frequency such that the subject receives a total of about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg active ingredient (i.e., lysate, lysate fraction, and/or cell wall fraction, or combination thereof) per day or more as needed.

Any and all of the above dosage amounts and administration amounts are applicable to both monotherapeutic administration of active ingredients of the disclosure, as well as to embodiments in which active ingredients of the disclosure are administered in combination with one or more other therapeutic or pharmaceutical agents.

Active Ingredients

Active ingredients to be used in the compositions and methods of the disclosure comprise a bacterial lysate, lysate fraction, or cell wall fraction. Active ingredients may be manufactured, produced, or derived from any Gram-positive or Gram-negative bacterial organism.

The term "lysate" as used herein refers to a composition prepared from a lysed cell, such as a bacterial cell. A lysate contains the entire cellular contents as well as, in some embodiments, associated surface components such as exo-polysaccharide, depending on the precise process conditions used to produce the lysate.

A non-limiting example process for producing an active ingredient according to the disclosure is set forth in Example 1, and in general involves the steps of (1) fermenting a bacterium in growth media; (2) centrifuging the bacterial suspension to harvest the bacteria therefrom; (3) washing and pasteurizing the harvested bacteria; (4) disrupting the cell walls of the bacteria to lyse the bacteria; and (4) lyophilizing the resulting mixture to obtain an active ingredient, such as a bacterial lysate, lysate fraction, or cell wall fraction.

The structures present in lysates, lysate fractions, and/or cell wall fractions of the disclosure that are responsible for TLR activation and oxidative stress reduction are structures common to and conserved among all bacterial microorganisms. Thus, in principle, any bacterial organism can be used to produce an active ingredient of the disclosure (i.e., lysate, lysate fraction, and/or cell wall fraction).

In some embodiments, the bacterial organism used to produce active ingredients of the disclosure is a Gram-positive bacterium. In some embodiments, the Gram-positive bacterium is selected from: *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus delbrueckii* subsp. *bulgaricus, Lactobacillus delbrueckii* subsp. *lactis, Lactobacillus helveticus, Lactobacillus jensenii, Lactobacillus leichmannii, Lactobacillus minutus, Lactobacillus paracasei, Lactobacillus plantarum, Lactobacillus rhamnosus, Lactobacillus rogosae, Lactobacillus salivarius, Lactobacillus sporogenes* (also known as *Bacillus coagulans*), *Lactobacillus brevis, Lactobacillus gasseri, Lactobacillus fermentum, Bifidobacterium adolescentis, Bifidobacterium animalis* (especially *B. animalis*, subspecies *animalis*), *Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium lactis (Bifidobacterium animalis* subsp. *lactis*), *Bifidobacterium longum, Bifidobacterium plantarum, Bifidobacterium pseudo-catenulatum, Bifidobacterium pseudo-longum, Leptococcus lactis, Streptococcus lactis* (also referred to as *Lactococcus lactis* subsp. *lactis*), *Streptococcus raffinolactis, Acidaminococcus fermenta, Cytophaga fermentans, Rhodoferax fermentans, Cellulomonas fermentans, Zymomonas mobilis, Pediococcus acidilactici,* or *Streptococcus thermophilus*, as well as functionally equivalent variants thereof.

In some embodiments, the bacterial organism used to produce active ingredients of the disclosure is a Gram-negative bacterium. In some embodiments, the Gram-negative bacterium is selected from: *Acinetobacter baumannii, Actinobacilllus, Acetobacter xylinus, Bacteroides thetaiotaomicron, Bacteroides fragalis, Bordetella pertussis, Brucella abortus, Campylobacter jejuni, Citobacter freundii, Enterobacter cloacae, Enterobacter sakasakii, Cyanobacteria, Erwinia amylovora, Escherichia coli, Franciscella tularensis, Helicobacter pylori, Haemophilus influenza, Legionella pneumophila, Moraxella catarrhalis, Neisseria gonorrhoeae, Proteus mirabilis, Pseudomonas aeruginosa, Pseudomonas flourescens, Salmonella enteritidis, Salmonella typhi, Serratia mareescens, Shigella flexneri, Vibrio cholera, Vibrio algenily, Ralstonia solanaceaerum, Mycobacterium tuberculosis, Mycobacterium kanassi, Klebsiella oxytocia,* and *Klebsiella pneumonia,* and *Xanthomonas campestris*. In some embodiments, the Gram-negative bacterium is selected from: the genera of *Pseudomonas, Klebsiella, Xanthomonas, Shigella* and *Enterobacter*. In some embodiments, the Gram-negative bacterium is one or more of *Escherichia coli, Klebsiella oxytocia, Shigella flexneri, Pseudomonas flourescens,* and *Xanthomonas campestris*, as well as functionally equivalent variants thereof.

All of the bacteria described above are believed to produce immune-stimulating cell components, such as but not limited to, EPS (exo-polysaccharide), which is distinct from the LPS (lipopolysaccharide) found in many bacteria. Other species of bacteria can also be used in the compositions and methods of the disclosure, for example, those disclosed in the state of the art and generally available in culture collections, such as the ECACC (European Collection of Cell Cultures), ASTM (American Society for Testing and Materials), ATCC (American Type Culture Collection), and DSM (German Collection of Microorganisms and Cell Cultures).

With regard to the fermentation step for producing lysates, lysate fractions, or cell wall fractions according to the disclosure, acceptable growth media to be used for fermentation will depend on the particular bacterium being grown. Typical growth media include those which comprise: a nitrogen source (1-4%), which may include one or more of the following yeast extract, milk protein and casein hydrolyzates, soy and soy hydrolyzates, meat extracts, peptones or ammonia salts; a simple sugar or ingredient that contains simple sugars or hydrolyzed carbohydrates that will yield simple sugars, such as but not limited to glucose or lactose (0.5-3%); and minerals (0.05-0.3%), which may include salts of sodium, manganese, magnesium, calcium and potassium. Surfactant, cysteine HCL, and ribonucleotides (0.001-0.75%) may be added to support cell growth. Growth media are adjusted to a pH between 6 and 8. In some embodiments, depending on the particular bacterium being grown, the pH of the growth media ranges from about 6.0 to 6.5. In some embodiments, the pH of the growth media ranges from about 6.5 to 7.0. In some embodiments, the pH of the growth media ranges from about 7.0 to 7.5.

In some embodiments, inoculated media is incubated during fermentation at between 30-50° C. In some embodiments, inoculated media is incubated during fermentation at between 30-40° C. In some embodiments, inoculated media is incubated at around 30° C., or around 31° C., or around 32° C., or around 33° C., or around 34° C., or around 35° C., or around 36° C., or around 37° C., or around 38° C., or around 39° C., or around 40° C., or around 45° C. In some embodiments, inoculated media is incubated at around 30° C. In some embodiments, inoculated media is incubated at around 33° C. In some embodiments, inoculated media is incubated at around 35° C. In some embodiments, inoculated media is incubated at around 37° C. In some embodiments, inoculated media is incubated at around 40° C. In some embodiments, inoculated media is incubated at around 45° C.

In some embodiments, fermentation is continued from about 6 hours to about 120 hours prior to harvesting the bacteria. In some embodiments, fermentation is continued from about 12 hours to about 48 hours prior to harvesting the bacteria. In some embodiments, fermentation is continued from about 12 hours to about 24 hours prior to harvesting the bacteria. In some embodiments, fermentation is continued for about 14 hours, or about 15 hours, or about 16 hours, or about 17 hours, or about 18 hours, or about 19 hours, or about 20 hours, or about 22 hours, or about 24 hours, or about 48 hours. In some embodiments, fermentation is continued until bacterial growth reaches the mid-logarithmic phase, the late-logarithmic phase, the early stationary phase, the mid-stationary phase, or the late stationary phase. In some embodiments, fermentation is continued until the bacteria reach the stationary growth phase. In some embodiments, the fermentation may be held prior to downstream processing using techniques known to those skilled in the art, such as but not limited to, chilling and pH control, for up to 14 days or longer as warranted.

After fermentation, the broth is typically chilled and the bacteria harvested by centrifugation. In some embodiments, the broth is chilled post-fermentation to from about 1° C. to about 25° C. In some embodiments, the broth is chilled to about 1° C., or to about 2° C., or to about 3° C., or to about 4° C., or to about 5° C., or to about 6° C., or to about 7° C., or to about 8° C., or to about 10° C. In some embodiments, the broth is chilled from to about 4° C. to about 7° C.

After chilling, centrifugation is performed to separate the cells from the surrounding growth media. Cells are then washed in fresh media, deionized water, water, or other solution via repeated centrifugations and resuspensions, and then re-suspended in fresh media or other solution in preparation for the pasteurization step.

In some embodiments, the washed bacteria are pasteurized. In some embodiments, the bacteria are pasteurized at from about 75° C. to about 85° C. for 30 minutes to 60 minutes. In some embodiments, the harvested bacteria are pasteurized at about 80° C. In some embodiments, pasteurization proceeds for about 30 minutes, or about 45 minutes, or about 60 minutes.

Following pasteurization, the cell concentrate is treated to disrupt cell walls and thereby expose TLR agonists. Disruption of the cell walls may be accomplished by using chelating agents, detergents, surfactants, and hydrolytic enzymes. Examples of hydrolytic enzymes that may be used include, but are not limited to, lysozyme, such as chicken (hen) egg white lysozyme (for example, INOVPUR®, LYSOLAC®, DELVOZYME®, LYSOVIN®, or LYSOBAC®), lysins, endolysins, and hydrolases. In some embodiments, lysozyme is added to the pasteurized bacterial cell suspension to a final concentration of 0.01-4% by volume. In some embodiments, lysozyme is added to the pasteurized bacterial cell suspension to a final concentration of about 0.5%, or about 1%, or about 2%, or about 3%, or about 4% by volume. In some embodiments, treatment of the pasteurized bacterial suspension with lysing enzymes continues from about 1 to about 10 hours, or from about 6 to about 8 hours, or for about 5 hours, or for about 6 hours, or for about 7 hours, or for about 8 hours, or for about 9 hours, or for about 10 hours. In some embodiments, treatment of the pasteurized bacterial suspension with lysing enzymes is performed at a temperature of from about 25° C. to about 50° C., or from about 30° C. to about 45° C., or at about 35° C., or at about 37° C., or at about 40° C., or at about 42° C., or at about 45° C. After lysis, the lysate is typically frozen and lyophilized.

In some embodiments, and as is described in more detail below, the lyophilized material is then blended with a promoter, such as N-acetyl D glucosamine HCl (NAG). Optionally, other formulation excipients may be added to generate a solid form pill or powder, as appropriate.

In some embodiments, the particular TLR or TLRs that are activated or stimulated by a particular lysate can be altered by changing raw materials, process materials, or process conditions. As used herein, the term "TLR specificity" refers to the particular TLR or TLRs that are activated by a given composition of the disclosure comprising a bacterial lysate, lysate fraction, and/or cell wall fraction. In some embodiments, TLR specificity is altered depending on the density to which bacterial cells are grown during fermentation. In some embodiments, the particular bacterial species or subspecies from which the active ingredient is produced also results in differences in TLR specificity. In some embodiments, the particular enzyme used to lyse the bacterial cells following pasteurization results in differences in TLR specificity.

As used herein, the terms "activation," "stimulation," "targeting," and "agonism," when used in relation to a receptor or other biomolecular target, are interchangeable and refer to the binding to and activation of a receptor, such as a toll-like receptor, such that the signaling cascade downstream of the receptor is altered, modulated, or otherwise affected.

It will be understood that the cells can be fractionated prior to lysis or that the lysate as produced above can be fractionated by well-known biochemical procedures, including, for example, differential centrifugation or column chromatography, such as gel-permeation chromatography, ion exchange chromatography, chromatography over hydrophobic media, or precipitation, and the like. In some embodiments, lysate fractionation produces fractions with differing TLR specificities; for example, fractions may be produced that are targeted to a smaller number of TLRs than a complete lysate.

In some embodiments, ingredients comprising exo-polysaccharides may be combined with the lysates, lysate fractions, and/or cell wall fractions of the disclosure. Exo-polysaccharides are able to activate TLRs. Thus, for example, xanthan gum, which is derived from *Xanthomonas campestris*, may be used in combination with the lysates, lysate fractions, and/or cell wall fractions of the disclosure to increase TLR activation and/or alter the TLR specificity of a composition. In some embodiments, xanthan gum is itself a lysate fraction, for example, in embodiments where xanthan gum is derived from a lysate produced from fermentation of *Xanthomonas campestris*, such as by fractionation of a *Xanthomonas campestris* lysate.

Other Ingredients and Delivery Forms

The therapeutic compositions of the present disclosure may further and optionally comprise one or more promoters, to assist in the therapeutic delivery of the active agent across a biological membrane. The promoter useful in accordance with the present disclosure can be amino acid, N-alkylated peptide, sugar, amino sugar or amino sugar chelate. An amino sugar chelate comprising one or more amino sugar ligands, one or more saturated hydroxylated carboxylic acid ligands, and a nutritionally acceptable metal, wherein at least one of the one or more amino sugar ligands is glucosamine, and wherein the metal is selected from the group consisting of manganese, magnesium, sodium, potassium, and zinc, and wherein the one or more saturated hydroxylated carboxylic acid ligands is gluconic acid, and wherein the glucosamine ligand to nutritionally acceptable metal ratio is 2:1, wherein the nutritionally metal is nonferrous.

In accordance with one aspect of the present disclosure, the therapeutic formulations may include one or more acetylated or deacetylated amino sugars selected from the group consisting of NAG, galactosamine, N-acetylgalactosamine, mannosamine, and N-acetylmannosamine in the form of monomers, oligomers, and/or polymers thereof including chitin, and human glucosaminoglycans, as well as derivatives thereof. The term "derivatives thereof" used herein with reference to amino sugars means derivatives of the amino sugars having the same or essentially the same ability to form cytotoxic degradation products during sterilization. In accordance with select further aspects of the present disclosure, the promoter is a member selected from the group consisting of poly-L-lysine, glucosamine, poly-L arginine, galactosamine, N-acetylmannosamine (NAM; N-Ac-Man), N-15 acetylglucosamine (NAG; N-Ac-Glc), N,N'-diacetylglucosamine (NAG-NAG; N,N'-diacetylchitobiose), N,N', N'', N'''-tetraacetylglucosamine (NAG-NAG-NAG-NAG; N,N',N'',N'''-tetraacetylchitotetraose), and mixtures thereof.

Optionally, and equally acceptable, the promoter may be an acylated glycosyloxy sugar or an optionally acylated oligoglycosyloxy sugar moiety of 2 to 12, a-1, 2 and/or a-1, 6 linked sugars, wherein the sugar(s) are selected from the group consisting of D-mannose, D-galactose, D-glucose, D-glucosamine, N-acetylglucosamine, and 6-deoxy-L-mannose, wherein an oligoglycosyloxy sugar moiety may comprise the same or different sugars.

In another embodiment, the compositions of the present invention are in a dosage form selected from the group consisting of a lozenge, a chewing gum, a chewable tablet, and a dissolving tablet such as a slow-dissolving tablet, a quick-dissolving tablet, or a controlled-release tablet or other suitable controlled-release formulation.

In an embodiment, the active agent of the present disclosure is delivered across an oral mucosa of a subject, the oral mucosa being selected from the group consisting of the sublingual mucosa, the buccal mucosa, and a combination thereof. The composition can be administered sublingually so that the active ingredient is delivered across the sublingual mucosa.

In another embodiment, the carrier is typically a solid, semi-solid, or liquid such as a binder, a gum base, or combinations thereof. Suitable binders for use in the compositions of the present invention include, without limitation, sugar alcohols such as mannitol, sorbitol, and xylitol; sugars such as lactose, dextrose, sucrose, glucose, and powdered sugar; other substances such as inositol, molasses, maltodextrin, starch, cellulose, microcrystalline cellulose, polyvinylpyrrolidone, acacia gum, guar gum, tragacanth gum, alginate, extract of Irish moss, panwar gum, ghatti gum, mucilage of isabgol (psyllium) husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol; and combinations thereof. Suitable gum bases for use in the compositions of the present invention include, for example, materials selected from among the many water-insoluble and saliva insoluble gum base materials known in the art. In certain instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000).

In yet another embodiment, the compositions of the present invention can further comprise a sweetening agent, a flavoring agent, a protecting agent, a plasticizer, a wax, an elastomeric solvent, a filler material, a preservative, or combinations thereof. In still yet another embodiment, the compositions of the present invention can further comprise a lubricating agent, a wetting agent, an emulsifying agent, a solubilizing agent, a suspending agent, a coloring agent, a disintegrating agent, or combinations thereof. In an embodiment, the average particle size of the drug in the compositions described herein is about 20 micrometers, as compared to a typical average drug particle size of from about 75 to about 100 micrometers. In another embodiment, the average particle size of the drug in the compositions described herein is less than or equal to the average particle size of the carrier ingredients (e.g., gum base, binders, etc.).

In one aspect of the present disclosure, the therapeutic composition may optionally include a buffer system to raise the pH of saliva to a pH of from about 8.0 to about 11, irrespective of the starting pH of saliva in the oral cavity of the subject to be treated. Suitable therapeutic agents for use in the present invention are described above. Suitable carbonate salts and bicarbonate salts for use in the buffer systems of the present invention are also described above. In certain instances, composition further comprises a non-biologic therapeutic agent, such as an NSAID.

Suitable citrate, phosphate, and borate salts include, without limitation, any salt of citric acid, phosphoric acid, or boric acid known in the art. For example, in some embodiments, the citrate salt is selected from the group consisting of sodium citrate, potassium citrate, calcium citrate, magnesium citrate, and ammonium citrate.

In other embodiments, the phosphate salt is selected from the group consisting of monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate. In yet other embodiments, the borate salt is selected from the group consisting of sodium borate, potassium borate, calcium borate, magnesium borate, and ammonium borate. In certain instances, the buffer system comprises a carbonate salt, a bicarbonate salt, and/or a citrate salt. In certain other instances, the buffer system comprises a carbonate salt, a bicarbonate salt, and/or a phosphate salt. In further instances, the buffer system comprises a carbonate salt, a bicarbonate salt, and/or a borate salt.

In addition to a buffer system comprising a carbonate salt, a bicarbonate salt, and/or a metal oxide, other buffer systems are suitable for use in the compositions of the present invention. For example, in an alternative embodiment, the ternary buffer system comprises a carbonate salt, a bicarbonate salt, and a citrate, phosphate, or borate salt. In another alternative embodiment, the buffer system comprises a carbonate salt or a bicarbonate salt and two or more buffering agents selected from the group consisting of a metal oxide, a citrate salt, a phosphate salt, and a borate salt.

In yet another alternative embodiment, the buffer system is a binary buffer system comprising a carbonate salt or a bicarbonate salt and a metal oxide. In still yet another alternative embodiment, the buffer system is a binary buffer system comprising, a carbonate salt or a bicarbonate salt and a citrate, phosphate, or borate salt. In a further alternative embodiment, the buffer system is a binary buffer system comprising a metal oxide and a citrate, phosphate, or borate salt. In still yet another alternative embodiment, the buffer system is a binary buffer system comprising a carbonate salt and a bicarbonate salt.

Delivery Forms

The therapeutic compositions of the present invention may take the form of solid, semi-solid, lyophilized powder, or liquid dosage forms, such as, for example, tablets (e.g., chewable, slow-dissolving, quick-dissolving), pills, capsules, lozenges, candies, gums, powders, solutions, suspensions, emulsions, aerosols, or the like. The dosage form can be a chewing gum, quick-dissolving tablet, candy, or lozenge.

As used herein, the term "dosage form" refers to physically discrete units suitable as unitary dosages for human subjects, mammals, and other non-mammalian animals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. For example, in some embodiments, a chewing gum dosage form of the present invention can be prepared according to procedures standard in the industry. In other embodiments, a tablet, lozenge, or candy dosage form (e.g., a sucker or lollipop) of the present invention can be prepared according to the procedures set forth in, for example, Remington's "The Science and Practice of Pharmacy, 20th Ed.," [Lippincott, Williams & Wilkins (2003); and, "Pharmaceutical Dosage Forms, Volume 1: Tablets," 2nd Ed., Marcel Dekker, Inc., New York, N.Y. (1989)]. The dosage form to be administered will, in any event, contain a quantity of the active therapeutic agent in a therapeutically effective amount for relief of the condition being treated when administered in accordance with the teachings of this invention.

As used herein, the term "carrier" refers to a typically inert substance used as a diluent or vehicle for a drug such as a therapeutic agent. The term also encompasses a typically inert substance that imparts cohesive qualities to the composition. Suitable carriers for use in the compositions of the present invention include, without limitation, a solid, semi-solid, or liquid such as a binder or a gum base. Examples of binders are known by one of ordinary skill in the art. Binders can be pre-processed to improve their flowability and taste by methods known in the art such as freeze drying [see, e.g., "Fundamentals of Freeze-Drying," Pharm. Biotechnol., Vol. 14, pp. 281-360 (2002); "Lyophilization of Unit Dose Pharmaceutical Dosage Forms," Drug. Dev. Ind. Pharm., Vol. 29, pp. 595-602 (2003)]; solid-solution preparation; and lubricant dusting and wet-granulation preparation with a suitable lubricating agent (see, e.g., Remington: The Science and Practice of Pharmacy, supra). When a binder is included in the formulation, the compositions of the present invention can comprise from about 15% to about 90% by weight of the binder, and from about 35% to about 80%. However, one skilled in the art will appreciate that the compositions of the present invention can be made without any binders, e.g., to produce a highly friable dosage form.

Tablets

When the dosage form is a tablet such as a dissolving tablet (i.e., disintegrating tablet) or chewable tablet, the compositions of the present invention comprise a therapeutic agent as described herein derived from one or more bacteria, or a pharmaceutically acceptable salt thereof, a promoter, a carrier such as a binder, and a buffer system, including binary or ternary buffer systems. The tablet composition may further comprise lubricating agents, wetting agents, emulsifying agents, suspending agents, preserving agents, sweetening agents, flavoring agents, coloring agents, and disintegrating agents. Typically, the tablet compositions of the present invention comprise from about 0.001% to about 10.0% by weight of the active therapeutic agent (in whatever chosen form, measured as per its free base form), and more typically from about 1.0% to about 5.0%. One skilled in the art understands that the foregoing percentages will vary depending upon the particular source of active therapeutic agent utilized, the amount of the active therapeutic agent desired in the final formulation, as well as on the particular release rate of the active therapeutic agent desired. The buffer system of the tablet composition provides for a final salivary pH in excess of at least about 8.0, at least about 9.5, and/or in the range of from about pH 9.9 to about pH 11.

In certain embodiments, the tablet is a dissolving tablet such as a slow-dissolving or quick-dissolving tablet that is dissolved by a subject's saliva, without the need for chewing. For example, a dissolving tablet placed on the subject's tongue can be used for buccal delivery of the therapeutic agent. Alternatively, a dissolving tablet placed underneath the subject's tongue can be used for sublingual delivery of the therapeutic agent. This type of dosage form may be particularly desirable for pediatric and geriatric patients, since small children and aged individuals often have difficulty chewing certain items. Typically, the dissolving tablet is formulated to dissolve within about 1 to about 15 minutes, within about 2 to about 10 minutes, e.g., within about 2, 3, 4, 5, 6, 7, 8, 9, or 10 minutes, following administration. One skilled in the art will understand that quick-dissolving tablets dissolve faster than slow-dissolving tablets, which are typically dissolved gradually rather than rapidly by a subject's saliva. In an embodiment, the slow-dissolving or quick-dissolving tablet delivers the therapeutic agent across the sublingual mucosa over a period of time greater than about 1 minute.

In certain other embodiments, the tablet is a chewable tablet that is chewed by a subject and formulated to dissolve either rapidly or gradually. For example, a chewable tablet placed on the subject's tongue can be used for buccal delivery of the therapeutic agent. During chewing, the chewable tablet can be moved around within the mouth and can sometimes be parked between the gums and the cheeks or underneath the tongue. As a result, at least a portion of the therapeutic agent contained within a chewable tablet may also be delivered sublingually (i.e., across the sublingual mucosa). Typically, the chewable tablet is formulated to dissolve within about 1 to about 15 minutes, within about 2 to about 10 minutes and not less than 1 minute, e.g., within about 2, 3, 4, 5, 6, 7, 8, 9, or 10 minutes, following administration.

As described above, the dissolving and chewable tablets of the present invention are typically formulated to dissolve within about 1 to 15 minutes following administration, and not less than about 1 minute after administration. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the tablet size (e.g., from about 700-800 mg to about 200-300 mg) without reducing the concentration or amount per unit dose of the buffer system or the therapeutic agent. In addition, subtle changes to the tablet formulation such as, for example, replacing one flavoring agent for another (e.g., chocolate for spearmint) or replacing one binder or sweetening agent for another (e.g., lactose for mannitol or sorbitol) may be used to reduce salivation.

Combinations with Other Pharmaceutical Agents

Many pharmaceutically active agents generate detrimental side effects, which are driven by ROS that are produced as the active agent proceeds through biochemical and other metabolic reactions. Thus, the compositions described herein are attractive candidates for the treatment of oxidative stress and oxidative stress-related diseases and conditions and can be combined with one or more pharmaceutical agents known in the art, such as any pharmaceutical agent listed in the Physician's Desk Reference (available at http://www.pdr.net).

In some embodiments, the active ingredients of the disclosure are combined with known pharmaceutical agents that target oxidative stress, inflammation, the immune response and/or oxidative stress-related diseases or conditions, or they can be combined with pharmaceutical agents that produce oxidative stress as a side effect. Where the pharmaceutical agent targets some other disease state but produces oxidative stress as a side effect, combination with the inventive compositions reduces damage caused by oxidative stress and also enhances the effectiveness of the pharmaceutical agent by allowing higher doses without prohibitive damage caused by oxidative stress. It will be appreciated that optimum results with a particular combination may require adjustment of the lysates to optimally target the correct TLRs in the presence of the added pharmaceutical agent.

Thus, in one aspect, the disclosure provides methods for reducing or alleviating one or more oxidative stress-related side effects associated with administration of a pharmaceutical agent, the methods comprising administering a lysate, lysate fraction, and/or cell wall fraction of the disclosure in combination with the pharmaceutical agent. In some embodiments, the pharmaceutical agent and lysate composition are administered simultaneously or in any order, and through the same or different routes of administration. In some embodiments, the pharmaceutical agent is any pharmaceutical agent with one or more oxidative stress-related side effects, such as any pharmaceutical agent listed in the Physician's Desk Reference (available at http://www.pdr.net) with one or more oxidative stress-related side effects. In some embodiments, the pharmaceutical agent is selected from the group consisting of anti-rheumatic drugs, anti-inflammatory agents, chemotherapeutic agents, radiotherapeutics, immunosuppressive agent, interferons, interferon-based chemotherapeutics, and cytotoxic drugs. In some embodiments, the oxidative stress-related side effects are selected from aceruloplasminemia, arterial/systemic hypertension, arthritis, asthma, atherosclerosis, atopic dermatitis, cancer, bladder cancer, leukemia, uterine cancer, cervical cancer, dizziness, nausea, vomiting, constipation, diarrhea, insomnia, drowsiness, lightheadedness, reduced libido, blackouts, shakes, jaundice, arrhythmia, increased heart rate, decreased heart rate, hives, depression, clinical depression, brain ischemia, bronchopulmonary dysplasia, cardiovascular diseases, cataract, cellulitis, chemotherapeutic side-effect, chronic fatigue syndrome, colitis, coronary artery disease, dyslipidemia, eclampsia, erectile dysfunction, ataxia, headache, heart failure, hemodialysis side effects, hepatic cirrhosis, hypercholesterolemia, hyperhomocysteinemia, hyperlipidemia, interstitial lung disease, lung injury, macular degeneration, male infertility, mild cognitive impairment, myocardial infarction, myocarditis, myopathy, neuropathy, obesity, osteoarthritis, osteoporosis, pancreatitis, periodontal disease, peritoneal dialysis side effects, posttraumatic stress disorder, preeclampsia, psoriasis, psoriatic arthritis, pulmonary hypertension, radio-therapy side effects, reactive arthritis, respiratory distress syndrome, rhabdomyolysis, rheumatic disease, sepsis, sleep apnea, stroke, suicidal thoughts, amyloidosis, thrombophily, tauopathies, unstable angina, uremia, or venous insufficiency.

In some embodiments, the pharmaceutical agent having one or more oxidative stress-related side effects is selected from the group consisting of: Antispasmodics selected from the group consisting of atropine sulphate, dicycloverine hydrochloride, hyoscine butylbromine, propantheline bromide, alverine citrate, and mebeverine hydrochloride; Motility stimulants selected from the group consisting of metoclorpramide and domperidone; H2-Receptor antagonists selected from the group consisting of Cimetidine, famotidinenizatidine, and ranitidine; Antimuscarinics; Chelates selected from the group consisting of Tripotassium dicitratbismuthate and sucralfate; Prostaglandin analogues; Aminosalicylates selected from the group consisting of balsazide sodium, mesalazine, olsalazine, and sulphasalazine; Corticosteroids selected from the group consisting of beclometasone dipropionate, budenoside, hydrocortisone, and prednisolone; Affecting immune response selected from the group consisting of ciclosporin, mercaptopurine, methotrexate, adalimumab, and infliximab; Stimulant Laxatives selected from the group consisting of bisacodyl, dantron, docusate, and sodium picosulfate; Drugs affecting biliary composition and flow; Bile acids sequestrants selected from the group consisting of colestyramine, Oxyphencyclimine, Camylofin, Mebeverine, Trimebutine, Rociverine, Dicycloverine, Dihexyverine, Difemerine, Piperidolate, Benzilone, Mepenzolate, Pipenzolate, Glycopyrronium, Oxyphenonium, Penthienate, Methantheline, Propantheline, Otilonium bromide, Tridihexethyl, Isopropamide, Hexocyclium, Poldine, Bevonium, Diphemanil, Tiemonium iodide, Prifinium bromide, Timepidium bromide, Fenpiverinium, Papaverine, Drotaverine, Moxaverine, 5-HT3 antagonists, 5-HT4 agonists, Fenpiprane, Diisopromine, Chlorbenzoxamine, Pinaverium, Fenoverine, Idanpramine, Proxazole, Alverine, Trepibutone, Isometheptene, Caroverine, Phloroglucinol, Silicones, Trimethyldiphenylpropylamine, Atropine, Hyoscyamine, Scopolamine, Butyl scopolamine, Methyl scopolamine, Methylatropine, Fentonium, Cimetropium bromide, and primarily dopamine antagonists; Proton pump inhibitors selected from the group consisting of Omeprazole, lansoprazole, pantoprazole, esomeprazole, and rabeprazole sodium; Opioids and opioid receptor antagonists; Analgesics selected from the group consisting of Acetaminophen, Diclofenac, Diflunisal, Etodolac, Fenoprofen, Flurbiprofen, Ibuprofen, Indomethacin, Ketoprofen, Ketorolac, Meclofenamate, Mefenamic Acid, Meloxicam, Nabumetone, Naproxen, Oxaprozin, Phenylbutazone, Piroxicam, Sulindac, Tolmetin, Celecoxib, Buprenorphine, Butorphanol, Codeine, Hydrocodone, Hydromorphone, Levorphanol, Meperidine, Methadone, Morphine, Nalbuphine, Oxycodone, Oxymorphone, Pentazocine, Propoxyphene, and Tramadol; Sleep drugs selected from the group consisting of Nitrazepam, Flurazepam, Loprazolam, Lormetazepam, Temazepam, Zaleplon, Zolpidem, Zopiclone, Chloral Hydrate, Triclofos, Clomethiazole, Quazepam, triazolam, Estazolam, Clonazepam, Alprazolam, Eszopiclone, Rozerem, Trazodone, Amitriptyline, Doxepin, Benzodiazepine drugs, melatonin, diphenhydramine, and herbal remedies; Cardiac glycosides selected from the group consisting of Digoxin and digitoxin; Phosphodiesterase inhibitors selected from the group consisting of enoximone and milrinone; Thiazides and related diuretics selected from the group consisting of bendroflumethiazide, chlortalidone, cyclopenthiazide, inapamide, metolazone, and xipamide; Diuretics selected from the group consisting of furosemide, bumetanide, and torasemide; Potassium sparing diuretics and aldosterone antagonists selected from the group consisting of amiloride hydrochloride, triamterene, weplerenone, and spironolactone; Osmotic diuretics; Drugs for arrhythmias selected from the group consisting of adenosine, amiodarone hydrochloride, disopyramide, flecainide acetate, propafenone hydrochloride, and lidocaine hydrochloride; Beta adrenoreceptor blocking drugs selected from the group consisting of propanalol, atenolol, acebutolol, bisprolol fumarate, carvedilol, celiprolol, esmolol, lebatolol, metoprolol tartrate, nadolol, nebivolol, oxprenolol, pindolol, solatol, and timolol; Hypertension drugs selected from the group consisting of ambrisentan, bosentan, diazoxide, hydralazine, iloprost, minoxidil, sildenafil, sitaxentan, sodium nitroprusside, clonidine, methyldopa, moxonidine, guanethidine monosulphate, doxazosin, indoramin, prazosin, terazosin, phenoxybenzamine, and phentolamine mesilate; Drugs affecting the renin-angiotensin system selected from the group consisting of Captropril, Cilazapril, Enalapril Maleate, Fosinopril, Imidapril, Lisinopril, Moexipril, Perindopril Erbumine, Quinapril, Ramipril, Trandolapril, Candesartan Cilexetil, Eprosartan, Irbesartan, Losartan, Olmesartan Medoxomil, Telmisartan, Valsartan, and Aliskiren; Nitrates, calcium channel Blockers, and antianginal drugs selected from the group consisting of Glyceryl trinitrate, Isosorbide Dinitrate, Isosorbide Mononitrate, Amlodipine, Diltiazem, Felodipine, Isradipine, Lacidipine, Lercanidipine, Nicardipine, Nifedipine, Nimodipine, Verapamil, Ivabradine, Nicorandil, and Ranolazine; Peripheral Vasodilators and related drugs selected from the group consisting of Cilostazol, Inositol Nicotinate, Moxisylyte, Naftidrofuryl Oxalate, and Pentoxifylline; Sympathomimetics selected from the group consisting of Dopamine, Dopexamine, Ephedrine, Metaraminol, Noradrenaline Acid Tartrate, Norephidrine Bitartrate, and Phenylephidrine; Anticoagulants and Protamine selected from the group consisting of Heparin, Bemiparin, Dalteparin, Enoxaparin, Tinzaparin, Danaparoid, Bivalirudin, Lepirudin, Epoprostenol, Fondaprinux, Warfarin, Acenocoumarol, Phenindione, Dabigatran Etexilate, Rivaroxaban, and Protamine Sulphate; Antiplatelet Drugs selected from the group consisting of Abciximab, Aspirin, Clopidogrel, Dipyridamole, Eptifibatide, Prasugrel, and Tirofiban; Fibrinolytic and antifibrinolytic drugs selected from the group consisting of Alteplase, Reteplase, Streptokinase, Tenecteplase, Urokinase, Etamsylate, and Tranexamic Acid; Lipid Regulating Drugs selected from the group consisting of Atorvastatin, Fluvastatin, Pravastatin, Rosuvastatin, Simvastatin, Colesevam, Colestyramine, Colestipol, Ezetimibe, Bezafibrate, Ciprofibrate, Fenofibrate, Gemfibrozyl, Acipmox, Nictotinic Acid, Omega three fatty acid compounds, Ethanolamine Oleate, and Sodium Tetradecyl Suphate; CNS Drugs selected from the group consisting of Benperidol, Chlorpromazine, Flupentixol, Haloperidol, Levomepromazine, Pericyazine, Perphenazine, Pimozide, Prochlorperazine, Promazine, Sulpiride, Trifluoperazine, Zuclopenthixol, Amisulpride, Aripiprazole, Clozapine, Olanzapine, Paliperidone, Quetiapine, Riperidone, Sertindole, Zotepine, Flupentixol, Fluphenazine, Olanzapine Embonate, Pipotiazine Palmitate, Risperidone, Zuclopenthixol Decanoate, Carbamazepine, Valproate, Valproic acid, Lithium Carbonate, Lithium Citrate, Amitriptyline, Clomipramine, Dosulepin, Imipramine, Lofepramine, Nortriptyline, Trimipramine, mianserin, Trazodone, Phenelzine, Isocarboxazid, Tranylcypromine, Moclobemide, Citalopram, Escitalopram, Fluoxetine, Fluvoxamine, Paroxetine, Sertraline, Agomelatine, Duloxetine, Flupentixol, Mirtazapine, Reboxetine, Trytophan, Venflaxine, Atomoxetine, Dexametamine, Methylphenidate, Modafinil, Eslicarbazepine, Ocarbazepene, Ethosuximide, Gabapentin, Pregabalin, Lacosamide, Lamotrigine, Levetiracetam, Phenobarbital, Primidone, Phenytoin, Rufinamide, Tiagabine, Topiramate, Vigabatrin, Zonisamide, ropinirole, Rotigotine, Co-Beneldopa, Levodopa, Co-Careldopa, Rasagiline, Selegiline, Entacapone, Tolcapone, Amantidine, Orphenadrine, Procyclidine, Trihexyphenidyl, Haloperidol, Piracetam, Riluzole, Tetrabenazine, Acamprosate, Disulfiram, Bupropion, Vareniciline, Buprenorphine, Lofexidine, Donepezil, Galantamine, Memantine, and Rivastigimine; Anti-Infectives selected from the group consisting of Benzylpenicillin, Phenoxymethylpenicillin, Flucloxacillin, Temocillin, Amoxicillin, Ampicillin, Co-Amoxiclav, Co-Fluampicil, Piperacillin, Ticarcillin, Pivmecillinam, Cephalosporins, Cefaclor, Cefadroxil, Cefalexin, Cefixime, Cefotaxime, Cefradine, Ceftazidime, Cefuroxime, Ertapenem, Imipenem, Meropenem, Aztreonam, Tetracycline, Demeclocycline, Doxocycline, Lymecycline, Minocycline, Oxytetracycline, Tigecycline, Gentamicin, Amikacin, Neomycin, Tobramycin, Erythromycin, Azithromycin, Clarithromycin, Telithromycin, Clindamycin, Chloramphenicol, Fusidic Acid, Vancomycin, Teicoplanin, Daptomycin, Linezolid, Quinupristin, Colistin, Co-Trimoxazole, Sulpadiazine, Trimethoprim, Capreomycin, Cycloserine, Ethambutol, Isoniazid, Pyrazinamide, Rifabutin, Rifampicin, Streptomycin, Dapsone, Clofazimine, Metronidazole, Tinidazole, Ciproflaxacin, Levoflaxacin, Moxifloxacin, Nalidixic Acid, Norflaxine, Orflaxacin, Nitrofurantoin, Methenamine Hippurate, Amphotericin, Anidulafungin, Caspofungin, Fluconazole, Flucytosine, Griseofluvin, Itraconzole, Ketoconazole, Micafungin, Nystatin, Posaconazole, Terbinafine, Voriconazole, Abacavir, Didanosine, Emtricitabine, Lamivudine, Stavudine, Tenofovir Disoproxil, Zidovudine, Atazanavir, Darunavir, Fosamprenavir, Indinavir, Lopinair, Nelfinavir, Ritonavir, Saquinavir, Tipranavir, Efavirenz, Etravirine, Nevarapine, Enfuvirtide, Maraviroc, Raltegravir, Aciclovir, Famciclovir, Inosine Pranobex, Valaciclovir, Cidofovir, Gangciclovir, Foscarnet, Valgangciclovir, Adefovir Dipivoxil, Entecavir, Telbivudine, Amantadine, Oseltamivir, Zanamivir, Palivizumab, Ribavirin, Artemether, Chloroquine, Mefloquine, Primaquine, Proguanil, Pyrimethamine, Quinine, Doxycyclin, Diloxanide Furoate, Metronidaziole, Tinidazole, Mepacrine, Sodium Stibogluconate, Atovaquone, Pentamidine Isetionate, Mebendazole, and Piperazine; Other drugs selected from the group consisting of Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, and Interferon Beta.

Thus, the therapeutic formulations of the disclosure may further comprise one or more additional therapeutic agents, such as any of the therapeutic agents described below. In some embodiments, the compositions are supplied as part of a sterile, pharmaceutical composition that includes a pharmaceutically acceptable carrier. Such compositions comprising additional therapeutic agents can be in any suitable form (depending upon the desired method of administering it to a patient). In some embodiments, the active ingredients of the disclosure are co-administered with one or more additional therapeutic agents, though are not necessarily combined into a single formulation with the one or more additional therapeutic agents. In some embodiments, the active ingredient(s) of the disclosure are administered via one route of administration, whereas the co-administered additional therapeutic agent(s) are administered via a second route of administration. For example, the active ingredients of the disclosure might be administered orally, mucosally, sublingually, buccally, etc., whereas the co-administered one or more additional therapeutic agents are administered parenterally, intravenously, etc.

Examples of compounds that can be combined with the inventive compositions include anti-rheumatic drugs, anti-inflammatory agents, chemotherapeutic agents, radiotherapeutics, immunosuppressive agent, interferons, interferon-based chemotherapeutics, or cytotoxic drugs.

Anti-rheumatic drugs include, but are not limited to, auranofin, azathioprine, chloroquine, D-penicillamine, gold sodium thiomalate hydroxychloroquine, Myocrisin and sulfasalazine methotrexate.

Anti-inflammatory agents include, but are not limited to, dexamethasone, pentasa, mesalazine, asacol, codeine phosphate, benorylate, fenbufen, naprosyn, diclofenac, etodolac and indomethacin, aspirin and ibuprofen, as well as other non-steroidal and anti-inflammatory agents (NSAIDS).

Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-.alpha., *Erwinia* L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon .alpha.-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptopurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan with carmustine implant, porfimer sodium, procaine, procarbazine HCL, propranolol, rituximab, sargramostim, streptozotocin, tamoxifen, taxol, teniposide, tenoposide, testolactone, tetracaine, thioepa, chlorambucil, thioguanine, thiotepa, topotecan HCL, toremifene citrate, trastuzumab, tretinoin, valrubicin, vinblastine sulfate, vincristine sulfate, and vinorelbine tartrate.

In yet other aspects of the disclosure, active ingredients of the disclosure are administered in combination with a TNF-α antagonist or an anti-TNF-α antibody. Examples of such TNF-α antagonists include, but are not limited to, soluble TNF-α receptors; etanercept (ENBREL®; Immunex) or a fragment, derivative or analog thereof; infliximab (REMICADE®; Centacor) or a derivative, analog or antigen-binding fragment thereof; Adalimumab (Humira and Exemptia), IL-10, which is known to block TNF-a production via interferon-y-activated macrophages, TNFR-IgG; the murine product TBP-1; the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (Athero-Genics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach.

In further aspects of the present disclosure, active ingredients of the disclosure are administered in combination with rapamycin, or similar macrocyclic antibiotics. As used herein, rapamycin includes rapamycin and all analogs, derivatives and congeners thereof, and other immunophilins that possesses the same pharmacologic properties as rapamycin is including inhibition of TOR or mTOR (mammalian target of rapamycin) (e.g., acting as a TOR kinase inhibitor). Other immunosuppressives that can be used as the one or more pharmaceutical or therapeutic agents include, but are not limited to, cyclosporine, tacrolimus (FK-506), azathloprine, and mycophenolate mofetil.

Further therapeutic agents that may be combined with the active ingredients of the disclosure include angiogenic agents such as vascular endothelial growth factor (VEGF) and fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retinoids; cyclin1 CDK inhibitors; HMG coenzyme reductase inhibitors (e.g., statins); and protease inhibitors.

TNF Inhibitors

A tumor necrosis factor (TNF) inhibitor, specifically a TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with oxidative stress diseases and disorders, such as [see definition], and related complications and symptoms.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (for example, from R & D Systems, Minneapolis, Minn.). TNFα is also referred to herein equivalently as TNF.

The term "TNFα inhibitor" refers to an agent which interferes with TNFα activity. The term also includes each of the anti-TNFα human antibodies and antibody portions described herein as well as those described in U.S. Pat. Nos. 6,090,382; 6,258,562; 6,509,015, and in U.S. Pat. No. 7,223,394). In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as "D2E7"). Additional TNF antibodies which can be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of Crohn's disease, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in, and, which are each incorporated by reference herein. The methods of the invention may also be performed using chimeric and humanized murine anti-hTNFa antibodies which have undergone clinical testing for treatment of rheumatoid arthritis (see e.g., Elliott, M. J., et al. (1994) *Lancet* 344: 1125-1127; Elliot, M. J., et al. (1994) Lancet 344:1105-1110; Rankin, E. C., et al. (1995) *Br. J. Rheumatol.* 34:334-342).

Thus, in one aspect, the disclosure provides toll-like receptor (TLR) agonist compositions for regulating redox status in a subject, the compositions comprising: (a) a TLR agonist comprising at least one or more lysate and/or lysate fraction of a bacterium, wherein the TLR agonist activates at least one or more TLRs or NLRs; (b) an optional promoter for enhancing absorption of the composition; and (c) an optional carrier for increasing a volume of the composition; wherein administration of an effective amount of the composition to the subject measurably reduces oxidative stress levels in the subject. In some embodiments, the agonist activates at least two different TLRs and/or NLRs. In some embodiments, the bacterium is a Gram-positive bacterium or a Gram-negative bacterium.

In some embodiments, the compositions are administered in combination with a pharmaceutical agent so as to enhance activity of the pharmaceutical agent. In some embodiments, the compositions are administered in combination with a pharmaceutical agent so as to reduce a side effect of the pharmaceutical agent. In some embodiments, the side effect of the pharmaceutical agent is oxidative stress.

In another aspect, the disclosure provides methods of regulating redox status in a subject, the methods comprising administering a therapeutically effective amount of any of the lysate or lysate fraction compositions disclosed herein to a subject in need thereof. In some embodiments, redox status regulation is assessed ideally by measuring changes in isoprostane concentration or by other methods including but not limited to gene expression in the subject. In some embodiments, the subject is a mammal. In some embodiments, the mammal is a human. In some embodiments, the subject is an animal which is not a mammal, such as, but not limited to, fish, fowl, crustaceans, and insects, such as *Drosophila*. In some embodiments, the redox status is oxidative and results in oxidative stress. In some embodiments, the oxidative stress in the human is related to post-traumatic stress disorder.

In another aspect, the disclosure provides methods of regulating redox status in a subject, the method comprising the steps of: (a) repeatedly administering to a subject in need thereof doses spaced apart in time and consisting of a composition comprising: (i) a toll-like receptor (TLR) agonist comprising at least one lysate and/or lysate fraction, wherein the agonist activates at least one or more different TLRs; (ii) an optional promoter for enhancing absorption of the composition; and (iii) an optional carrier for increasing a volume of the composition; and (b) making measurements of a bodily fluid of the subject to detect changes in oxidative stress levels. In some embodiments, the TLR agonist activates at least three different TLRs. In some embodiments, the TLR agonist comprises lysate(s) and/or lysate fraction(s) and/or cell wall fraction(s) from a single species of bacteria. In some embodiments, the TLR agonist comprises lysate(s) and/or lysate fraction(s) from at least two species or strains of bacteria.

In some embodiments, making measurements of a bodily fluid assesses changes in isoprostane concentration in the subject. In some embodiments, changes in isoprostane concentration are measured indirectly by methods including but not limited to gene expression in the subject. In some embodiments, the subject is a mammal. In some embodiments, the mammal is a human. In some embodiments, the subject is an animal other than a mammal, such as, but not limited to, fish, fowl, crustaceans, and insects, such as *Drosophila*. In some embodiments, the oxidative stress in the human is related to post-traumatic stress disorder.

In another aspect, the disclosure provides methods of decreasing the amount of isoprostane in the urine or blood of a subject, the method comprising the steps of: (a) determining the level of isoprostane in the urine or blood of the subject; (b) administering to the subject an effective amount of a composition comprising: (i) a toll-like receptor (TLR) agonist comprising at least one bacterial lysate and/or lysate fraction from a bacterium, wherein the TLR agonist activates at least one or more TLRs or NLRs; and (ii) an optional promoter for enhancing absorption of the composition; and (c) continuing administration of the composition until the level of isoprostane in the urine or blood of the subject is decreased.

In another aspect, the disclosure provides compositions comprising: (a) a bacterial lysate and/or lysate fraction capable of activating at least one or more toll-like receptors (TLRs) or Nod-like receptor (NLR); (b) an optional promoter for enhancing absorption of the composition; and (c) an optional carrier for increasing a volume of the composition.

In another aspect, the disclosure provides pharmaceutical formulations comprising any of the compositions disclosed herein. In some embodiments, the pharmaceutical formulations are formulated for buccal or sublingual administration. In some embodiments, the pharmaceutical formulations are formulated to dissolve in not less than 1 minute after administration.

In another aspect, the disclosure provides methods of producing a bacterial lysate, the method comprising the steps of: (a) fermenting a Gram-positive or Gram-negative bacterium in a growth medium to the stationary growth phase to produce a fermentation broth; (b) harvesting bacteria from the fermentation broth; (c) pasteurizing the harvested bacteria; and (d) lysing the pasteurized bacteria with a lysozyme to produce a bacterial lysate. In some embodiments, the lysate is harvested at different times of the growth cycle after beginning any particular fermentation. In some embodiments, the bacteria are fermented in a characteristically defined media.

In another aspect, the disclosure provides bacterial lysates produced according to a process, the process comprising the steps of: (a) fermenting a Gram-positive or Gram-negative bacterium in a growth medium to the stationary growth phase to produce a fermentation broth; (b) harvesting bacteria from the fermentation broth; (c) pasteurizing the harvested bacteria; and (d) lysing the pasteurized bacteria with a lysozyme to produce a bacterial lysate. In some embodiments, the lysate is harvested at different times of the growth cycle after beginning any particular fermentation. In some embodiments, the bacteria are fermented in a characteristically defined media.

In another aspect, the disclosure provides methods for alleviating one or more oxidative stress-related side effects associated with administration of a pharmaceutical agent, the method comprising administering in combination with the pharmaceutical agent a therapeutically effective amount of a composition comprising: (a) a lysate and/or lysate fraction of a bacterium; (b) an optional promoter for enhancing absorption of the composition; and (c) an optional carrier for increasing a volume of the composition; wherein the pharmaceutical agent and lysate composition are administered simultaneously or in any order, and through the same or different routes of administration. In some embodiments, the lysate and/or lysate fraction activates at least one or more TLRs or NLRs. In some embodiments, the lysate and/or lysate fraction activates at least two TLRs and/or NLRs. In some embodiments, the lysate and/or lysate fraction activates at least three TLRs and/or NLRs.

In some embodiments, the one or more oxidative stress-related side effects are selected from the group consisting of: aceruloplasminemia, arterial/systemic hypertension, arthritis, asthma, atherosclerosis, atopic dermatitis, cancer, bladder cancer, leukemia, uterine cancer, cervical cancer, dizziness, nausea, vomiting, constipation, diarrhea, insomnia, drowsiness, lightheadedness, reduced libido, blackouts, shakes, jaundice, arrhythmia, increased heart rate, decreased heart rate, hives, depression, clinical depression, brain ischemia, bronchopulmonary dysplasia, cardiovascular diseases, cataract, cellulitis, chemotherapeutic side-effect, chronic fatigue syndrome, colitis, coronary artery disease, dyslipidemia, eclampsia, erectile dysfunction, ataxia, headache, heart failure, hemodialysis side effects, hepatic cirrhosis, hypercholesterolemia, hyperhomocysteinemia, hyperlipidemia, interstitial lung disease, lung injury, macular degeneration, male infertility, mild cognitive impairment, myocardial infarction, myocarditis, myopathy, neuropathy, obesity, osteoarthritis, osteoporosis, pancreatitis, periodontal disease, peritoneal dialysis side effects, post-traumatic stress disorder, preeclampsia, psoriasis, psoriatic arthritis, pulmonary hypertension, radio-therapy side effects, reactive arthritis, respiratory distress syndrome, rhabdomyolysis, rheumatic disease, sepsis, sleep apnea, stroke, suicidal thoughts, amyloidosis, thrombophily, tauopathies, unstable angina, uremia, and venous insufficiency.

In another aspect, the disclosure provides methods for treating oxidative stress-related diseases or conditions in a subject, the methods comprising administering to the subject a therapeutically effective amount of a composition comprising: (a) a bacterial lysate and/or lysate fraction capable of activating at least one or more toll-like receptors (TLRs) or Nod-like receptors (NLRs); (b) an optional promoter for enhancing absorption of the composition; and (c) an optional carrier for increasing a volume of the composition.

In some embodiments, the oxidative stress-related condition is aceruloplasminemia, acute and chronic alcoholic liver diseases, acute autoimmune myocarditis, acute chest syndrome of sickle cell disease, acute pancreatitis, acute respiratory distress syndrome, alcoholic liver disease, Amyotrophic Lateral Sclerosis, arterial/systemic hypertension, asbestosis, asthma, ataxia telangiectasia, atherosclerosis, atopic dermatitis, brain ischemia, bronchopulmonary dysplasia, burns, some cancers, cardiopulmonary bypass, cardiovascular diseases, cataract, cellulitis, chemotherapeutic side-effect, chronic fatigue syndrome, chronic Hepatitis C, chronic kidney disease, chronic obstructive pulmonary disease, chronic renal failure, colitis, coronary artery disease, Creutzfeldt-Jakob disease, Crohn's disease, cutaneous leishmaniasis, cystic fibrosis, diabetes mellitus type 1, diabetes mellitus type 2, dyslipidemia, Down's syndrome, eclampsia, end-stage renal disease, erectile dysfunction, Friedreich ataxia, headache, heart failure, *Helicobacter pylori* infection/inflammation, hemodialysis side effects, hepatic cirrhosis, Human Immunodeficiency Virus infection, Huntington disease, hyperbaric diseases, hypercholesterolemia, hyperhomocysteinemia, hyperlipidemia, idiopathic pulmonary fibrosis, interstitial lung disease, ischemia/reperfusion injury, juvenile chronic arthritis, kidney transplantation failure, leukemia, lung cancer, lung injury, macular degeneration, male infertility, Ménière's syndrome, meningitis, mild cognitive impairment, Multiple Sclerosis, myelodisplastic syndromes, myocardial infarction, myocarditis, neonatal bronchopulmonary dysplasia, obesity, osteoarthritis, osteoporosis, pancreatitis, Parkinson's disease, periodontal disease, peritoneal dialysis side effects, photoageing, post-traumatic stress disorder, preeclampsia, primary biliary cirrhosis, broncopulmonary diseases, progeria, psoriasis, psoriatic arthritis, pulmonary hypertension, radio-therapy side effects, reactive arthritis, renal cell carcinoma, respiratory distress syndrome, retinopathy of prematurity, retrolenticolar fibroplasy, rheumatic disease, rheumatoid arthritis, sarcoidosis, sepsis, sickle cell disease, sleep apnea, spherocytosis, spinal cord injury, stroke, synucleinopathies, systemic amyloidosis, systemic lupus erythematosus, systemic sclerosis (scleroderma), thrombophily, tauopathies, traumatic stress tubercolosis, unstable angina, uremia, venous insufficiency, Werner syndrome, or Zellweger syndrome.

In another aspect, the disclosure provides methods for reducing oxidative stress in a subject, the methods comprising: (a) determining the level of oxidative stress in the subject by measuring the amount of isoprostane in the urine or blood of the subject; (b) administering to the subject an effective amount of a composition comprising: (i) a toll-like receptor (TLR) agonist comprising at least one lysate and/or lysate fraction from a Gram-negative or Gram-positive bacterium, wherein the TLR agonist activates at least one or more different TLRs or NLRs; and (ii) an optional promoter for enhancing absorption of the composition; and (c) continuing administration of the composition until the level of oxidative stress is reduced, as determined by a decreased amount of isoprostane in the urine of the subject.

In some embodiments, of any of the above aspects, administration of the bacterial lysate is continued until the amount of isoprostane in the urine of the subject is less than about 3 ng per mg creatinine, less than about 2 ng per mg creatinine, less than about 1 ng per mg creatinine, or less than about 0.5 ng per mg of creatinine.

In another aspect, the disclosure provides pharmaceutical formulations comprising the combination of: (a) a lysate composition comprising (i) a bacterial lysate and/or lysate fraction capable of activating at least one or more toll-like receptors (TLR) or Nod-like receptors (NLR); (ii) an optional promoter for enhancing absorption of the composition; and (iii) an optional carrier for increasing a volume of the composition; and (b) one or more pharmaceutical agents. In some embodiments, the one or more pharmaceutical agents are selected from the group consisting of: an antispasmodic, a motility stimulant, an H2-Receptor antagonist, antimuscarinic; a chelate, a prostaglandin analog, an aminosalicylate, a corticosteroid, an drug affecting immune response, a stimulant laxative, a drug affecting biliary composition and flow, a bile acids sequestrant, a dopamine antagonist, a proton pump inhibitor, an opioid, an opioid receptor antagonist, an analgesic, a sleep drug, a cardiac glycoside, a phosphodiesterase inhibitor, a thiazide, a diuretic, a potassium sparing diuretic, an aldosterone antagonist, an osmotic diuretic, a drug for arrhythmia, a bbeta adrenoreceptor blocking drug, a hypertension drug, a drug affecting the renin-angiotensin system, a nitrate, a calcium blocker, an antianginal drug, a peripheral vasodilator, a sympathomimetic, an anticoagulant, a protamine, an antiplatelet drug, a fibrinolytic drug, an antifibrinolytic drug, a lipid regulating drug, an omega three fatty acid compound, a CNS drug, an anti-infective, or another drug selected from the group consisting of Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, and Interferon Beta.

In another aspect, the disclosure provides formulations, such as pharmaceutical formulations, comprising: (a) a lysate composition comprising (i) a bacterial lysate and/or lysate fraction capable of activating at least one or more toll-like receptors (TLRs) or Nod-like receptors (NLRs); (ii) an optional promoter for enhancing absorption of the composition; and (iii) an optional carrier for increasing a volume of the composition; and (b) an isolated human anti-TNFalpha antibody or antigen-binding fragment thereof or TNF inhibitor. In some embodiments, the human anti-TNFalpha antibody or antigen-binding fragment thereof is adalimumab. In some embodiments, the disclosure provides uses of the combination formulations of this aspect in the manufacture of a medicament for the treatment of rheumatoid arthritis (RA) or late-onset RA in a subject. In some embodiments, the disclosure provides methods for the treatment of rheumatoid arthritis (RA) or late-onset RA in a subject, the method comprising administering to the subject a therapeutically effective amount of the combination formulation of this aspect, and as disclosed herein. In some embodiments, the subject is over 50 years old. In some embodiments, the human anti-TNFalpha antibody or antigen-binding fragment thereof is administered to the subject in a biweekly dosing regimen. In some embodiments, the human anti-TNFalpha antibody or antigen-binding fragment thereof is administered to the subject in a dose of 30 mg or greater. In some embodiments, the TNFalpha inhibitor a TNFalpha fusion protein. In some embodiments, the TNFalpha fusion protein is etanercept. In some embodiments, the anti-TNFalpha antibody or antigen-binding fragment thereof is infliximab or golimumab. In some embodiments, the anti-TNFalpha antibody or antigen-binding fragment thereof is adalimumab.

In another aspect, the disclosure provides methods for inhibiting oxidative stress-related disease or disorder progression in a human subject having an oxidative stress-related disease or disorder associated with a disorder in which TNFα activity is detrimental, the method comprising: administering to the subject having an oxidative disease or disorder a lysate, lysate fraction, and/or cell wall fraction of the disclosure, and an isolated human anti-TNFα antibody, or antigen-binding portion thereof, such that oxidative stress disease progression is inhibited in the subject, wherein the human anti-TNFα antibody, or an antigen-binding portion thereof, neutralizes human TNFα cytotoxicity in a standard in vitro L929 assay with an $IC_{50}$ of $1\times10^{-7}$M or less. In some embodiments, the lysate of the disclosure and the human anti-TNFα, or antigen-binding portion thereof, are administered at different times under different dosing regimens. In some embodiments, the human anti-TNFα antibody is golimumab, or an antigen-binding portion thereof. In some embodiments, the human anti-TNFα antibody is adalimumab, or an antigen-binding portion thereof. In some embodiments, the human anti-TNFα antibody, or antigen-binding portion thereof, is administered to the subject on a biweekly dosing regimen. In some embodiments, the methods further comprise administering an additional therapeutic agent to the subject. In some embodiments, the lysate of the disclosure is administered for a period of at least 24 weeks. In some embodiments, the anti-TNFα antibody, or antigen-binding portion thereof, is administered for a period of at least 24 weeks. In some embodiments, the lysate of the disclosure, the anti-TNFα antibody, or antigen-binding portion thereof, or both, repairs or prevents oxidative damage to the subject by a combination of one or more different mechanisms.

In some embodiments of any of the methods or compositions disclosed herein, the bacterium is a Gram-positive or Gram-negative bacterium. In some embodiments of any of the methods or compositions disclosed herein, the Gram-positive bacterium is selected from the group consisting of a bacterium of Lactobacillaceae family, a bacterium of Streptococcaceae family, a bacterium of Bifidobacteriaceae family, and a bacterium of Bacillaceae family. In some embodiments, the Gram-positive bacterium is selected from the group consisting of *Bacillus coagulans, Lactobacillus sporogenes, Streptococcus thermophilus, Bifidobacterium animalis, Bifidobacterium. animalis*, subspecies *animalis, Bifidobacterium infantis, Bifidobacterium longum, Bifidobacterium breve, Lactobacillus acidophilus, Lactobacillus plantarum, Lactobacillus casei, Lactobacillus delbrueckii, Lactobacillus delbrueckii* subspecies *bulgaricus, Lactococcus lactis, Lactococcus lactis* subspecies *lactis, Streptococcus lactis, Streptococcus thermophilus, Bifidobacterium lactis, Bifidobacterium breve, Pediococcus acidilactici*, and *Lactobacillus helveticus*.

In some embodiments of any of the methods or compositions (including formulations) disclosed herein, the Gram-negative bacterium is selected from the group consisting of a bacterium of *Pseudomonas* genus, *Klebsiella* genus, *Xanthomonas* genus, *Shigella* genus, and *Enterobacter* genus. In some embodiments, the Gram-negative bacterium is selected from the group consisting of *Klebsiella oxytocia, Shigella flexneri, Xanthomonas campestris*, and *Pseudomonas flourescens*.

In some embodiments of any of the methods or compositions (including formulations) disclosed herein, the TLR agonist, lysate, lysate fraction, or cell wall fraction activates at least one or more of TLR 2, TLR 3, TLR 4, TLR 5, TLR 7, TLR 8, TLR 9, NOD1, and NOD2. In some embodiments, the TLR agonist, lysate, lysate fraction, or cell wall fraction activates two or more of TLR 2, TLR 3, TLR 4, TLR 5, TLR 7, TLR 8, TLR 9, NOD1, and NOD2. In some embodiments, the TLR agonist, lysate, lysate fraction, or cell wall fraction activates TLR 2 and TLR 4. In some embodiments, the TLR agonist, lysate, lysate fraction, or cell wall fraction activates three or more of TLR 2, TLR 3, TLR 4, TLR 5, TLR 7, TLR 8, TLR 9, NOD1, and NOD2.

In some embodiments of any of the methods or compositions (including formulations) disclosed herein, the promoter is selected from the group consisting of amino acids, amino sugars, and sugars. In some embodiments, the carrier is selected from the group consisting of a binder, a gum base, and combinations thereof. In some embodiments, the gum base comprises at least one hydrophobic polymer and at least one hydrophilic polymer. In some embodiments, the binder is selected from the group consisting of a sugar, a sugar alcohol, and combinations thereof. In some embodiments, the sugar alcohol is selected from the group consisting of mannitol, sorbitol, xylitol, and combinations thereof.

In some embodiments, the compositions are manufactured as a dosage form selected from the group consisting of a lozenge, a chewing gum, a chewable tablet, a candy, and a dissolving tablet. In some embodiments, the dosage form delivers the TLR agonist to an oral mucosa. In some embodiments, the oral mucosa is selected from the group consisting of the sublingual mucosa, buccal mucosa, and a combination thereof.

In some embodiments of any of the methods or compositions (including formulations) disclosed herein, the compositions are formulated for oral mucosal delivery; in some embodiments, the compositions are formulated for sublingual or buccal delivery. In some embodiments, the compositions are formulated to dissolve in not less than 1 minute after administration.

EXAMPLES

The Examples that follow are illustrative of specific embodiments of the invention, and various uses thereof. They are set forth for explanatory purposes only, and are not to be taken as limiting the invention.

Example 1: Preparation of Active Ingredient for TLR Agonist Compositions

An example of how to formulate the composition includes the following process.

Active Ingredient. The active ingredient was derived from a bacterial fermentation and cell isolation process as described below. *Lactobacillus delbrueckii*, ssp. *bulgaricus* (referred to herein as *L. bulgaricus*) was the organism used in this example, but the bacterial organism may be any Gram-positive or Gram-negative bacterium, or both.

*Lactobacillus delbrueckii* ssp *bulgaricus* was fermented in growth media comprising 1.5% casein hydrolysate, 1% yeast extract, 3% lactose, 0.2% sodium acetate, 0.02% sodium formate, 0.01% disodium 5-inosinate, 0.01% manganese sulfate, 0.05% magnesium sulfate, and 0.05% polysorbate 80, pH 6.4. Inoculated media was incubated at 37° C. until the fermentation reached stationary growth, as determined by cessation of metabolism. Fermentation broth was chilled to 4° C. and harvested by centrifugation at about 4000-4500×g.

The concentrated cells were washed two sequential times using chilled water and by running the cells through the centrifuge again. Washed cell concentrate was pasteurized at 80° C. for 45 minutes.

Following pasteurization, the cell concentrate was treated to disrupt cell walls and thereby lyse the bacteria and expose TLR agonists. Disruption of bacterial cell walls was accomplished using chicken egg white lysozyme at a concentration of 3% by wt. for 7 hours at 40° C. The resulting lysate was frozen and lyophilized.

The lyophilized material was blended with a promoter, such as N-acetyl D glucosamine HCl (NAG), to form a mixture of lysed *Lactobacillus delbrueckii* subsp. *Bulgaricus* and NAG. Optionally, other formulation excipients to generate a solid form pill or powder were added, as appropriate. This product was then used in the following screening tests.

Example 2: TLR Screening Assay

Toll-like receptor (TLR) stimulation was tested by assessing NF-KB activation in HEK293 cells expressing a given TLR or Nod-like receptor (NLR). The activities of the samples were tested on seven different human TLRs: TLR2, 3, 4, 5, 7, 8 and 9 (Invivogen, San Diego, CA), and on two different human NLRs, nucleotide-binding oligomerization domain-containing proteins 1 and 2 (NOD1 and NOD2). Each ligand was tested at a final concentration of 1/100 of the stock solution on the TLR or NLR cells, and compared to control ligands, as described below. This step was performed in triplicate.

The control ligands, control cell lines, and sample product used in the examples were as shown in Table 1.

TABLE 1

Control ligands and control cell line information used in ligand screening tests.

| | |
|---|---|
| Control Ligands | TLR2: HKLM (heat-killed *Listeria monocytogenes*) at $10^8$ cells/mL <br> TLR3: Poly(I:C) at 1 µg/mL <br> TLR4: *E. coli* K12 LPS at 100 ng/mL <br> TLR5: *S. typhimurium* flagellin at 100 ng/ml <br> TLR7: CL097 at 1 µg/mL <br> TLR8: CL075 at 1 µg/mL <br> TLR9: CpG ODN 2006 at 100 ng/mL <br> NOD1: C12iEDAP at 10 µg/mL <br> NOD2: L18-MDP at 100 ng/mL |
| Control Cell Lines | HEK293/Null1: TNF-alpha at 1 µg/mL (control for human TLR 2, 3, 5, 8, 9 and NOD 1) <br> HEK293/Null1-k: TNF-alpha at 1 µg/mL (control for human TLR7) <br> HEK293/Null2: TNF-alpha at 1 µg/mL (control for human TLR4 and NOD2) |
| Sample | Lysate of *Lactobacillus delbrueckii* subsp. *bulgaricus* (1/10 dilution prepared in sterile, endotoxin-free water) |

General Procedure. TLR stimulation in the screening is tested by assessing NF-KB activation in the HEK293 cells expressing a given TLR. The secreted alkaline phosphatase reporter is under the control of a promoter inducible by the transcription factor NF-KB. TLR stimulation in the screening was tested by assessing NF-KB activation in the HEK293 cells expressing a given TLR or NLR. This reporter gene allows the monitoring of signaling through the TLR/NLR, based on the activation of NF-KB. In a 96-well plate (200 µL total volume) containing the appropriate cells (50,000-75,000 cells/well), 20 µL of the Sample (lysate product) or the positive control ligands to the wells. The media added to the wells is designed for the detection of NFKB induced SEAP (secreted alkaline phosphatase) expression. After a 16-20 hr incubation, the OD (optical density) at 650 nm was read on a Molecular Devices Spectra Max 340PC absorbance detector and recorded.

Figure 2:
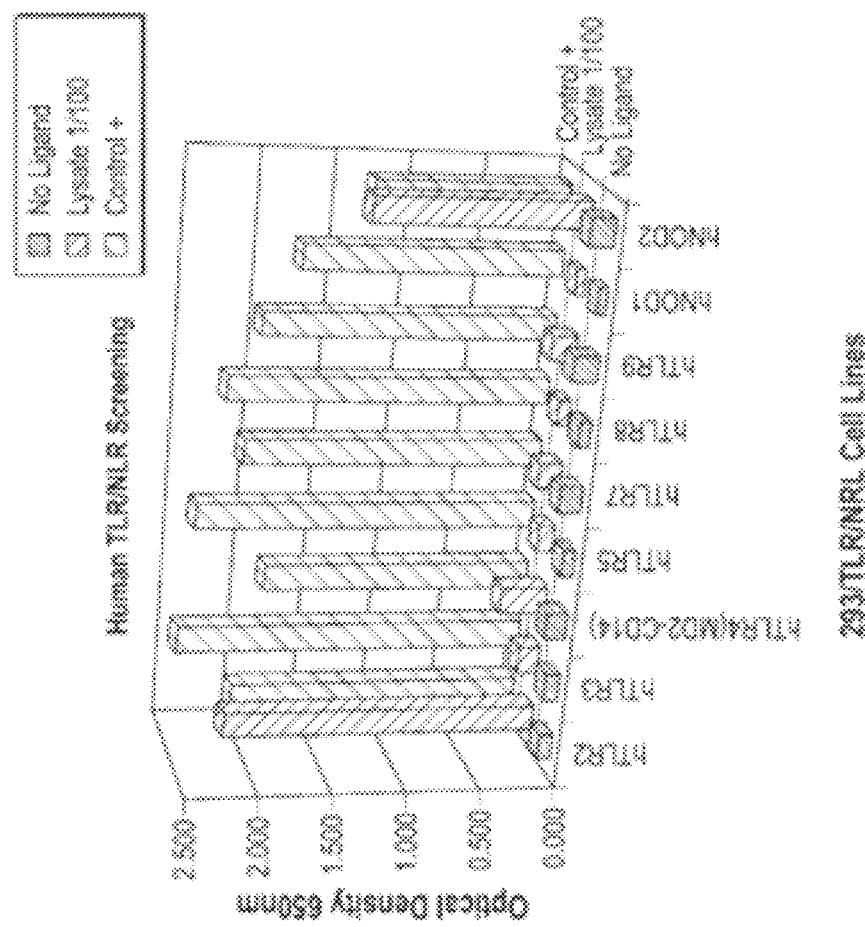
FIG. 2 shows the exemplary stimulatory effects of a composition of the present invention on select TLR/NLR cell lines; the values in the graph correspond to an average of three screening experiments.

The screening results of these experiments are shown graphically in FIG. 2. These results show that a typical lysate produced as described above is a strong agonist for at least TLR2 (and TLR4 to a lesser extent) and NOD2.

Example 3: Effects of Changes in Process Variables on TLR Signaling

Through observations of the effects of certain process changes on TLR signaling, it was noted that TLR signal pattern could be altered.

Figure 3:
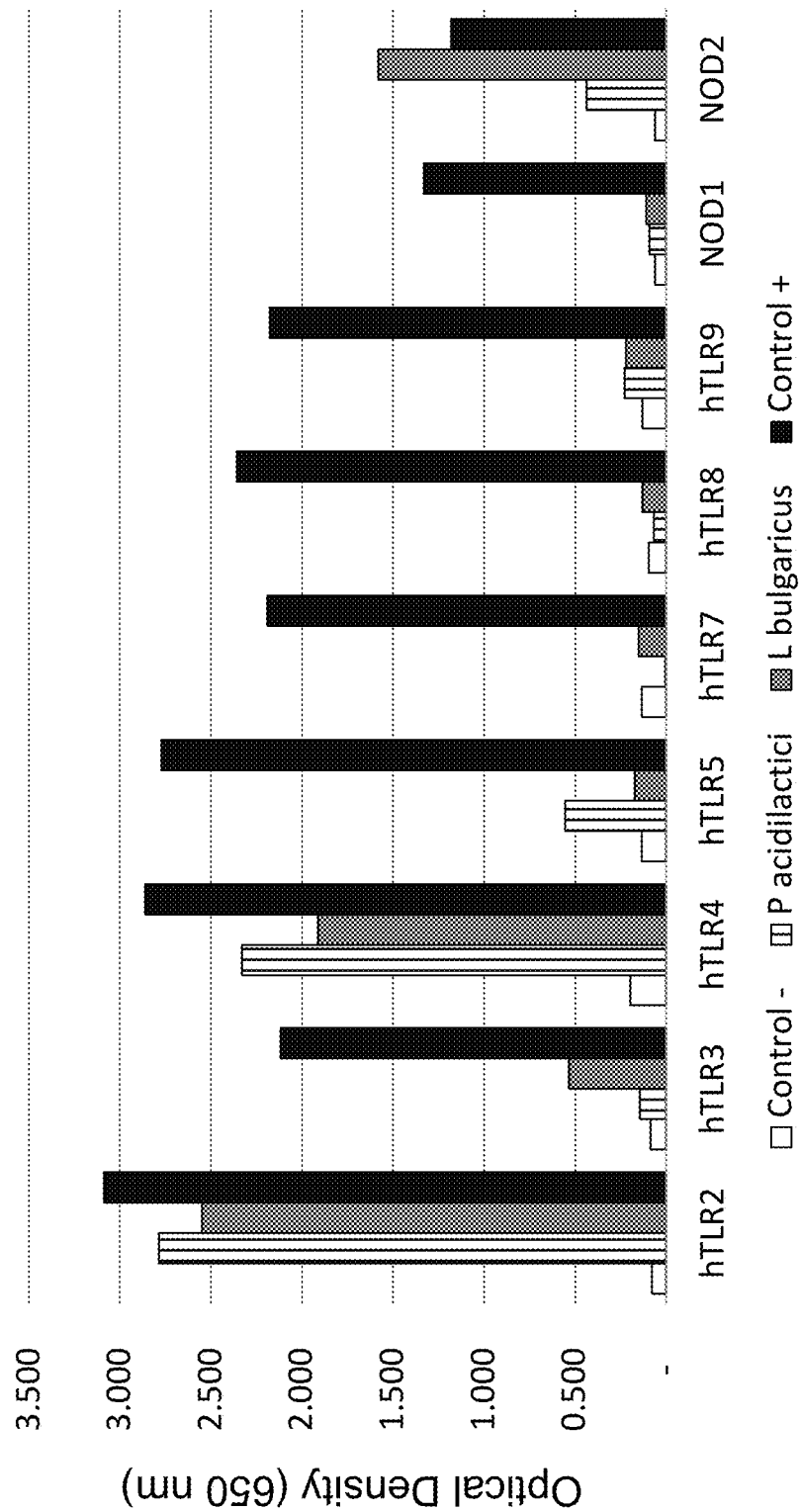
FIG. 3 shows results of TLR stimulation for a *Pediococcus acidilactici* lysate as compared to a *Lactobacillus bulgaricus* lysate.

FIG. 3 shows the difference of the cell morphology has on the TLR signal for a Gram-positive organism. Lysate from *Pediococcus acidilactici*, a cocci organism, produced higher TLR4 and lower NOD2 signals compared to *L. bulgaricus*, a rod organism, while the TLR 2 signal produced by *P. acidilactici* was only slightly higher than that produced by *L.*

*bulgaricus*. NOD2 activation was significantly lower in *P. acidilactici* which is reflective of the lower muramyl peptides found in cocci.

Figure 4:
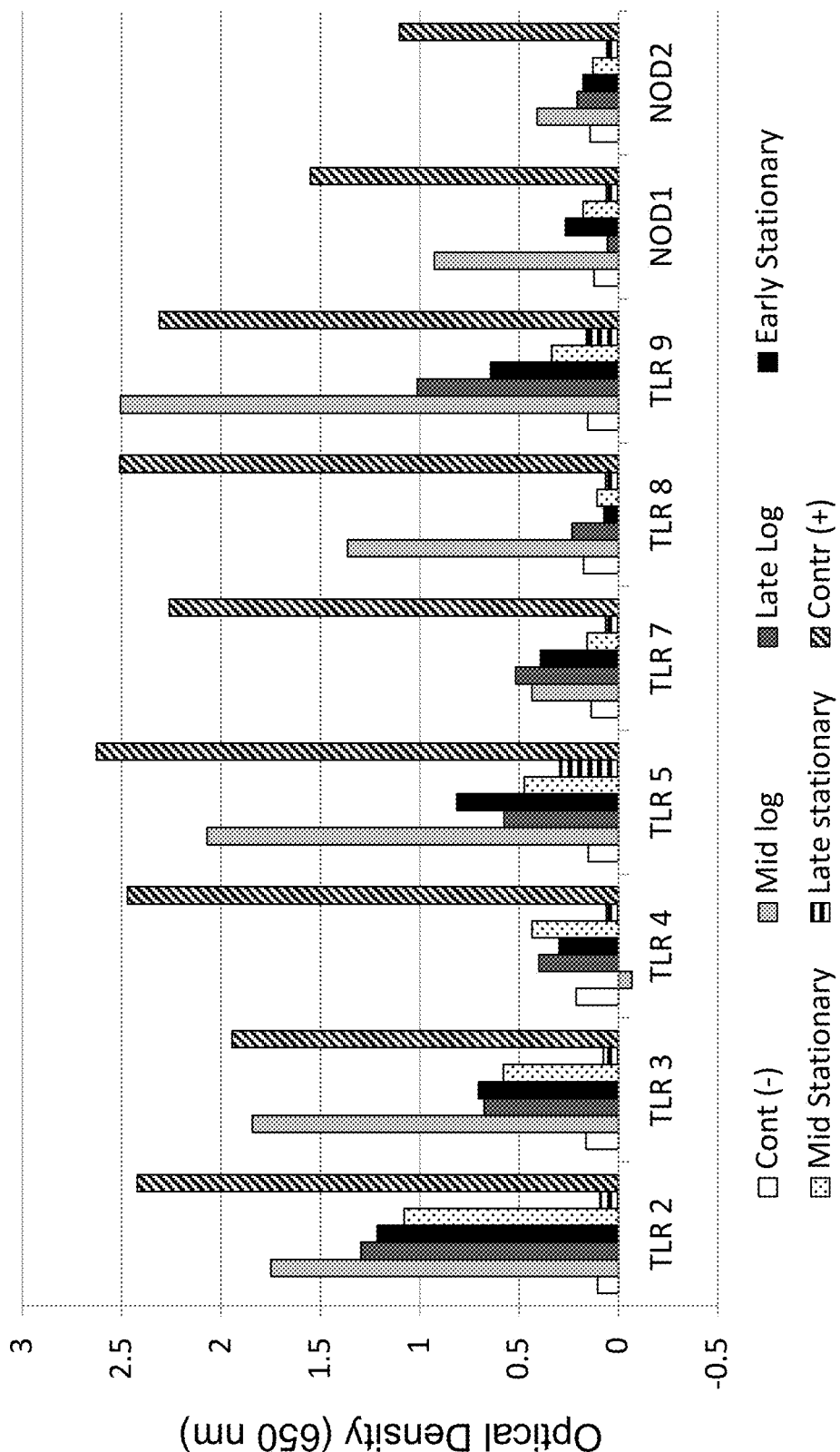
FIG. 4 shows results of TLR stimulation for *Bacillus coagulans* lysates with differing times of harvest.

TLR signal patterns were also impacted by the time of culture harvest for a *Bacillus coagulans* lysate, as depicted in FIG. 4. *Bacillus coagulans* was grown using a standard yeast extract/glucose media with a pH of 6.5 in shake flasks incubated at 45° C. and 250 rpm. Harvest of the cultures followed the lysate production process of Example 1 but by varying the time of harvest of bacteria after fermentation according to growth phase: mid-logarithmic phase, late-logarithmic phase, early stationary phase, mid-stationary phase, and late stationary phase as determined by OD, substrate depletion, metabolite production and EPS. In general, these data demonstrate that TLR activation specificity can be altered by changing the time of bacterial harvest after fermentation. For example, lysate produced from cultures harvested at the mid-log phase activated all targets tested except for TLR 4 and had the highest signal for TLRs 2, 3, 5, 8, 9 and NOD1. TLR signal strength decreased as the culture left log phase and went into stationary phase, with a complete cessation of TLR signal during late stationary. Cell culture was plated at all stages of harvest and cell count was noted to be greater than $5 \times 10^8$ CFU/ml at all time points. No endospores were noted upon visual inspection of the culture. The TLR effects noted from the lysates were from vegetative cells. A large amount of EPS was noted on the sidewalls of the late stationary culture.

Figure 5:
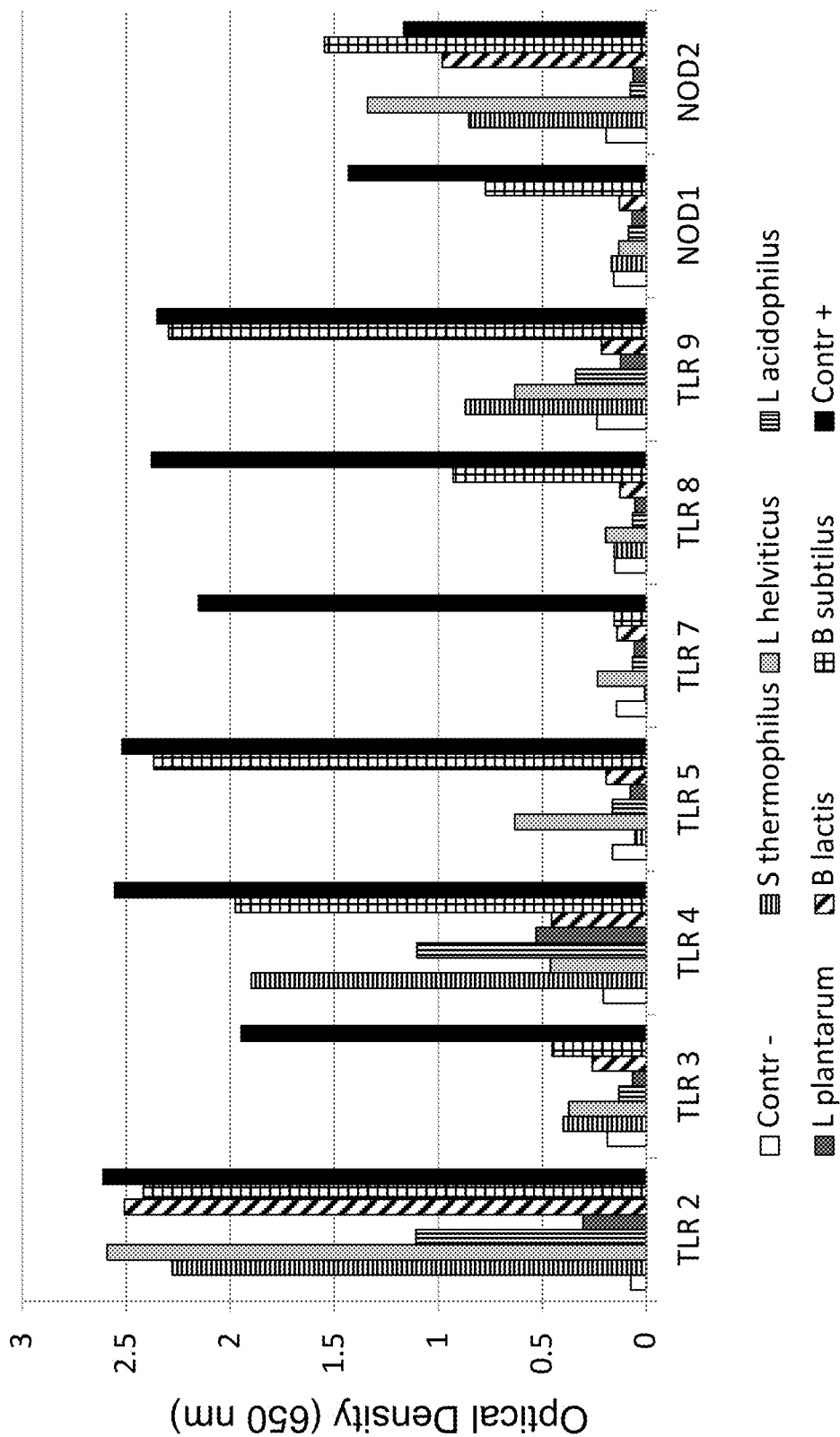
FIG. 5 shows results of TLR stimulation for Gram-positive bacterial lysates from *Lactobacillus acidophilus, Lactobacillus helviticus, Lactobacillus plantarum*, and *Streptococcus thermophilus.*

FIG. 5 shows TLR signal patterns obtained from lysates of selected Gram-positive organisms. *Streptococcus thermophilus, Lactobacillus helveticus, Lactobacillus acidophilus, Lactobacillus plantarum, Bifidobacterium animalis* subsp *lactis*, and *Bacillus subtilis* were grown on a standard yeast extract/lactose/casein hydrolyzate media at pH 6.5 in shake flasks incubated at 37° C. and 110 rpm. *Lactobacillus plantarum, Bifidobacterium animalis* subsp. *lactis* (*B. lactis*), and *Bacillus subtilis* were grown on yeast extract media/glucose media at pH 6.5 in shake flasks incubated at 37° C. and 110 rpm, whereas *B. subtilis* was incubated at 37° C. and 250 rpm. *B. lactis* also had 0.05% cysteine HCL added to the media. Harvest of the cultures followed the lysate production process of Example 1. *S thermophilus*, a cocci organism, gave a TLR signal pattern (high TLR 2 and TLR 4, and low NOD2) that was similar to the other cocci culture *P. acidilactici*, as noted in Example 4. However, *B. lactis*, although a different morphology than *L. bulgaricus* gave a similar TLR pattern. There was little similarity in the TLR pattern across the Gram-positive rod cultures of *L. helviticus, L. acidophilus, L. plantarum*, and *B. subtilis*. *L. heliviticus* produced a TLR pattern similar to the TLR pattern of *L. bulgaricus*. *L. acidophilus*, although lower in signal strength, produced results similar to the patterns produced by the cocci. *L. acidophilus* did not produce any noticeable EPS when the culture was harvested and concentrated, whereas *L. bulgaricus, L. helviticus*, and *B. lactis* all produced noticeable EPS, and all produced similar TLR signal patterns. *L. plantarum* lysate had a very different TLR signal pattern than the other Gram-positive organisms, in which all TLR signals were muted. This muting of the signal pattern was not obvious from the characteristics of the fermentation, but *L. plantarum* is known to produce numerous metabolites that may account for the reduction in TLR signals. *B. subtilis* had a similar TLR pattern to the log-phase-harvested culture of *B. coagulans*, except it produced higher TLR 4 activation. Overall, TLR signal patterns across Gram-positive organisms varied according to the morphology, EPS production, and metabolites of the organisms.

Figure 6:
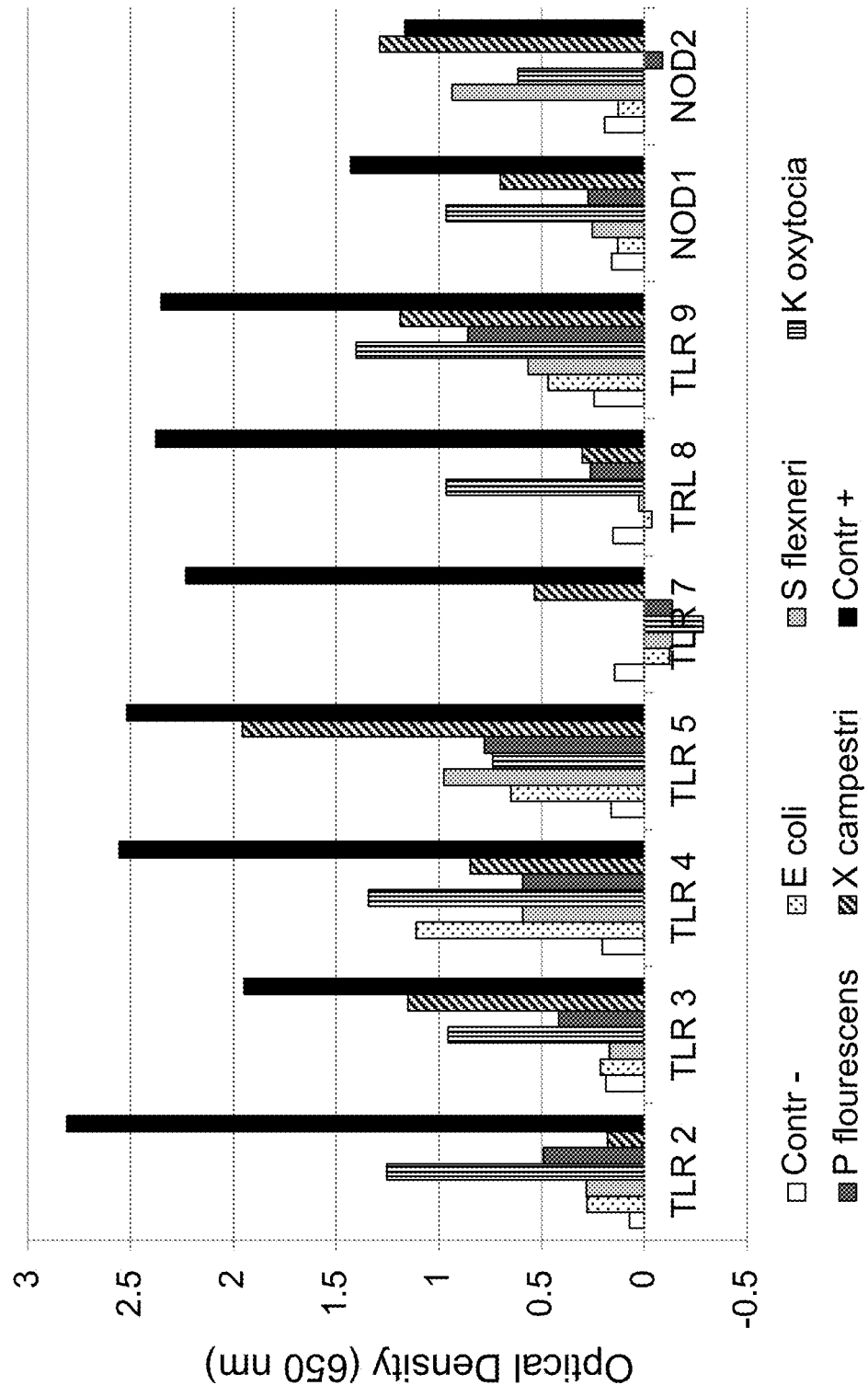
FIG. 6 shows results of TLR stimulation for Gram-negative bacterial lysates from *Escherichia coli, Klebsiella oxytocia, Shigella flexneri, Xanthomonas campestris*, and *Pseudomonas flourescens.*

FIG. 6 shows TLR signal patterns obtained from lysates of selected Gram-negative organisms. *Escherichia coli, Klebsiella oxytocia, Shigella flexneri, Pseudomonas flourescens*, and *Xanthomonas campestris* were grown using Tryptic Soy Broth in shake flasks. *K. oxytocia, E. coli*, and *S. flexneri* were incubated at 37° C. and 250 rpm while *P. flourescens* and *Xanthomonas campestris* were incubated at 30° C. and 250 rpm. *Xanthomonas campestris* was grown using a yeast extract/glucose media supplemented with calcium carbonate at 1%. Prior to harvesting, the $CaCO_3$ was removed by centrifugation at 500×g for 3 minutes. Harvest of the cultures from the fermentation broth followed the lysate production process of Example 1. Surprisingly and unexpectedly, the TLR signal pattern of the lysate from Gram-negative organisms, including *E. coli*, when tested at similar concentrations, were much lower in signal strength than the lysates of Gram-positive organisms, except for TLR 5 and 9. In general, the Gram-negative bacteria membrane/cell wall is easier to break than that of Gram-positive bacteria, which may explain the higher TLR 9 signal. *K. oxytocia* and *X. campestris* was observed to produce EPS during fermentation and also produced relatively high activation of TLR 3, 4 and 9. *K. oxytocia* produced the highest TLR2 and NOD1 activation of the strains tested. EPS appears to alter the TLR signal pattern as compared to non-EPS producing strains (*S. flexneri*). Interestingly, all Gram-negative bacteria had significant activation of the NF-kappaB of the Null cells in the TLR assay. This NF-kappaB activity was subtracted from the TLR signal and explains the slightly negative activities for TLR 7 and NOD2 for *P. flourescens*.

Figure 7:
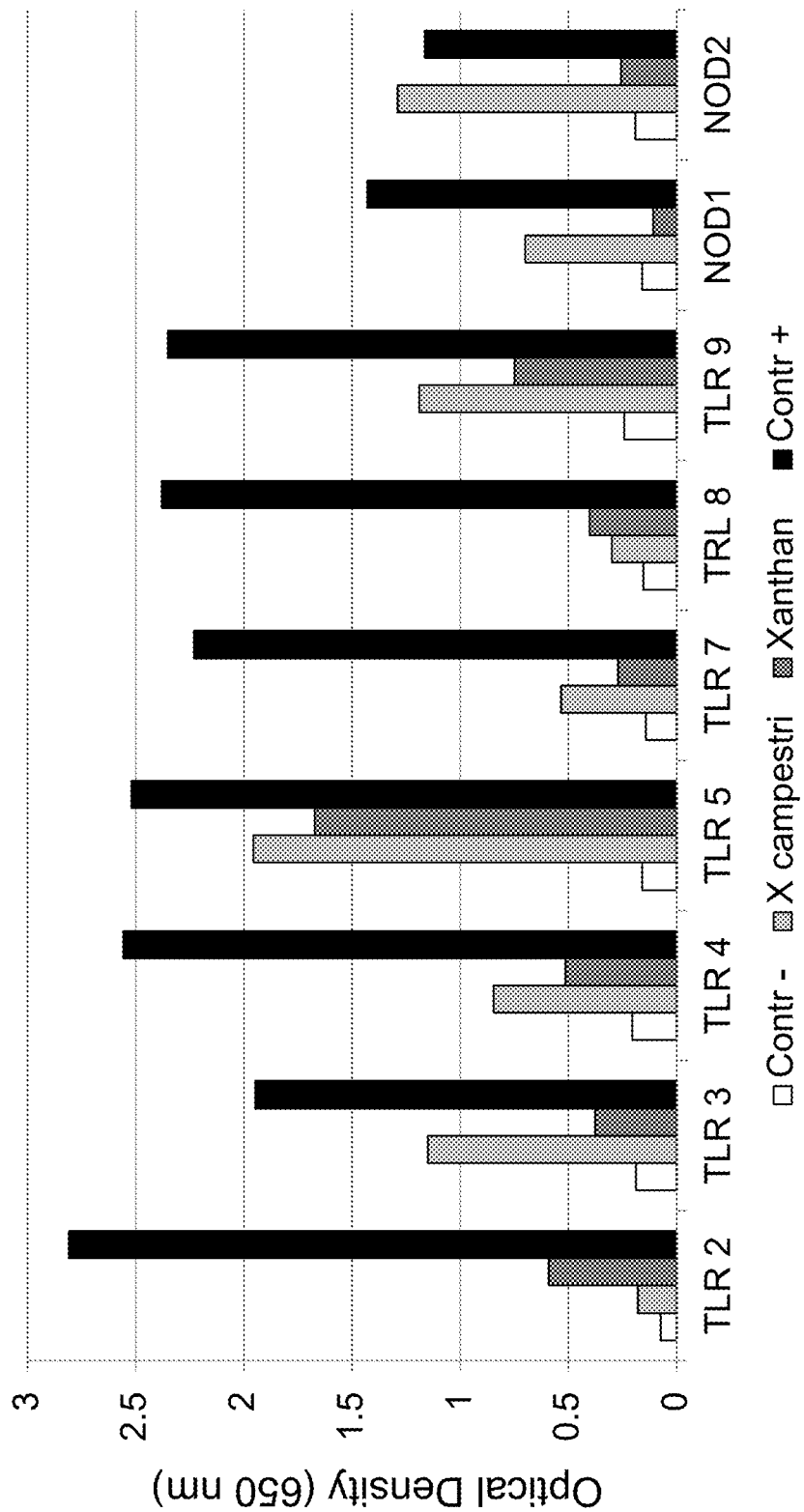
FIG. 7 shows the results of TLR stimulation for a *Xanthomonas campestris* lysate as compared to xanthan gum.

Lastly, FIG. 7 shows TLR signaling for a lysate composition comprising xanthan gum. These data demonstrate that the lysate produced from the strain *Xanthomonas campestris*, as well as xanthan gum itself, the EPS produced by the strain *Xanthomonas campestris*, both produce TLR activation. There is strong stimulation by both the strain and the EPS xanthan gum at TLR5 and moderate activity at TLRs 4 and 9. These data suggest that the lysate from a given bacterial strain, as well as the corresponding EPS from that strain (e.g., xanthan gum in this example) can both be used in or blended into a formulation for a targeted TLR activity.

Surprisingly and unexpectedly, these data demonstrate that the TLR signal pattern resulting from a given lysate, as well as the strength of the TLR signal, is dependent on the manufacturing process as well as choice of raw materials, including, but not limited to, media and microorganisms. These data demonstrate that TLR activation specificity can be altered and tailored by changing process, bacterial organism, raw material, and reagent parameters.

Example 4: Oxidative Stress, Cognitive and Quality of Life Indicators in Post-Traumatic Stress Disorder (PTSD)-Diagnosed Combat Veterans PTSD is an oxidative stress-related disease or condition. The purposes of the study were four-fold: (1) to evaluate the effectiveness of the inventive composition in quantitatively reducing levels of the oxidative stress marker isoprostane in PTSD-diagnosed combat veterans; (2) to evaluate the effectiveness of the inventive composition in qualitatively reducing levels of nitric oxide in PTSD-diagnosed combat veterans; (3) to evaluate the effectiveness of the inventive composition in improving word finding and word recall in PTSD-diagnosed combat veterans; and (4) to evaluate the effectiveness of the inventive composition in improving quality of life parameters in PTSD-diagnosed combat veterans.

Emerging evidence-based literature supports the link between oxidative stress and post-traumatic stress disorder (PTSD). Oxidative stress occurs in the body and on the cellular level as a result of an imbalance between circulating oxidants and anti-oxidants. Many studies have shown that this cellular oxidative stress results from the effect of free radicals on the body's neurophysiology. Nitric oxide has been implicated as playing an important role in protecting against oxidative stress.

Word-finding is often affected in individuals who suffer from Traumatic Brain Injury as well as in combat veterans. Closed Head Injury/Traumatic Brain Injury (CHI/TBI) and PTSD are frequently co-morbid conditions.

Criteria for Subject Selection.

The anticipated number of participants in the study was a minimum of 10 and maximum of 15.

The anticipated gender distribution was as close to 50% male and 50% female as possible. Due to the larger numbers of male veterans diagnosed with PTSD, it was possible that there could be a slightly larger male percentage in the participant pool.

Pregnant women were not allowed to participate in the study.

The only age restriction was due to the military recruitment minimum age, 18 years old, so the anticipated age range for the study was from 18 to approximately 80, with the upper limit dictated by level of health.

There were no racial or ethnic origin restrictions. The intended percentages based on race mirrored those of the greater Houston area, from which the participants were recruited. These percentages are roughly: 44% Hispanic, 26% white, 23% African America, 6% Asian, 1% other.

Inclusion and Exclusion criteria are outlined in Table 2 below.

TABLE 2

Inclusion and exclusion criteria for Example 3.

| Inclusion Criteria | Exclusion Criteria |
|---|---|
| combat or military veteran | pregnant females |
| resides in the greater Houston area | any psychiatric hospitalization within the past 10 months |
| PTSD diagnosis from the Veteran Health Administration of the U.S. Department of Veterans Affairs | current probiotic use |
| | life-threatening medical condition |
| | unstable physical health |
| | children or participants under the age of 18 |
| | classification as "other traditionally defined vulnerable subjects such as prisoners" |
| | lack of adequate capacity to render informed consent |

Methods and Procedures.

Under informed consent, participants were evaluated to assess levels of cellular oxidative stress, nitric oxide levels, language/word-finding ability, levels of anxiety and depression, and current quality of life parameters.

Participants were provided with 15 days of the composition, which is hypothesized to reduce oxidative stress, as indicated specifically by a reduction in urinary Isoprostane levels. Two (2) 12-mg product tablets were taken sublingually two (2) times per day, for a total of 48 mg daily.

To minimize measurement fluctuation no placebos were used, and subjects served as their own measurement controls. All subjects were assigned to the same study group and received the same procedure.

Oxidative stress was measured via urinalysis of isoprostane using a commercially available assay (Oxford Biomedical Research). Samples collected were normalized creatine using a creatinine assay kit (Oxford Biomedical Research) to control for differences in the level of concentration of the urine.

Each participant had his/her urine tested for isoprostane levels, at a minimum, on days 1 and 15. A consistent subset of individuals were asked to submit urine samples each of the 15 days of the study to establish data points as a means of examining possible isoprostane changes over time. A third party (naïve to the study goals) was retained to conduct the isoprostane assays.

All participants had three (3) language tests administered in private rooms on days 1 and 15. The language tests used were the Receptive One-Word Picture Vocabulary Test, 4th edition (ROWPVT-4), the Expressive One-Word Picture Vocabulary Test, 4th edition (EOWPVT-4), and the Test of Non-Verbal Intelligence, 4th edition (TONI-4).

Additionally each participant was asked to complete a Zung Self-Rating Scale for Anxiety and Depression, a Satisfaction with Life Scale (SWLS), and the Eppworth Sleepiness Scale on days 1 and 15. These forms were filled out in private rooms and were coded using standard methods to mask identifying information of participants.

Each participant filled out a daily Quality of Life (QOL) Survey which was emailed to him/her every morning at 4:00 am. In order to familiarize each participant with the QOL Survey format and to establish a stronger baseline of data, each individual began recording his/her scores on the QOL Survey a minimum of four (4) days prior to beginning his/her use of product.

Data Analysis and Data Monitoring.

After the aforementioned parameters were gathered over 15 days, the study data were analyzed for trends in identifying oxidative stress and nitric oxide levels, word-find ability, the presence of anxiety/depression, and overall quality of life ratings. The statistical analysis methods used were straightforward as only one quantitative parameter, isoprostane, was assessed. Appropriate multivariate statistical tests were used to analyze the data.

Risk/Benefit Assessment.

Risk category: The risk category for this trial was "Minimal." As such, consent for injury language in the consent form was not necessary, and a clinical trial agreement (CTA) was therefore not necessary. The minimal risk category was due to the fact that the product being tested is recognized as a food-grade GRAS compound found in yogurt. Furthermore, there were no invasive procedures being performed as urine and saliva were the only body fluids being collected.

At the time of data collection, there were approximately 35 individuals taking the product, both male and female. At the time of the study, the longest using individual started the product 17 months prior and reported no negative side effects from use of the product. Of approximately 35 total individuals who were administered the product, no negative side effects were reported.

Method of Subject Identification and Recruitment

The study used a convenience sample, the method of recruiting participants being based largely on personal and professional contacts of the investigators.

Subject Capacity

If the individual was deemed to lack adequate capacity to consent, they were not allowed to participate in the study. There were no minors involved in this study, and no one who required an assent form or legal representative present.

Subject Comprehension

To assess that adequate comprehension has taken place, the participant was required to explain the study back to the individual doing the consent process before they were allowed to enroll in the study. The subject confirmed that all their questions were answered adequately.

Results

In the study, effects of the supplement were assessed by measuring/analyzing: 1) isoprostane levels; 2) quality of life survey results; 3) Zung/psychological survey results; and 4) speech language results.

Figure 8:
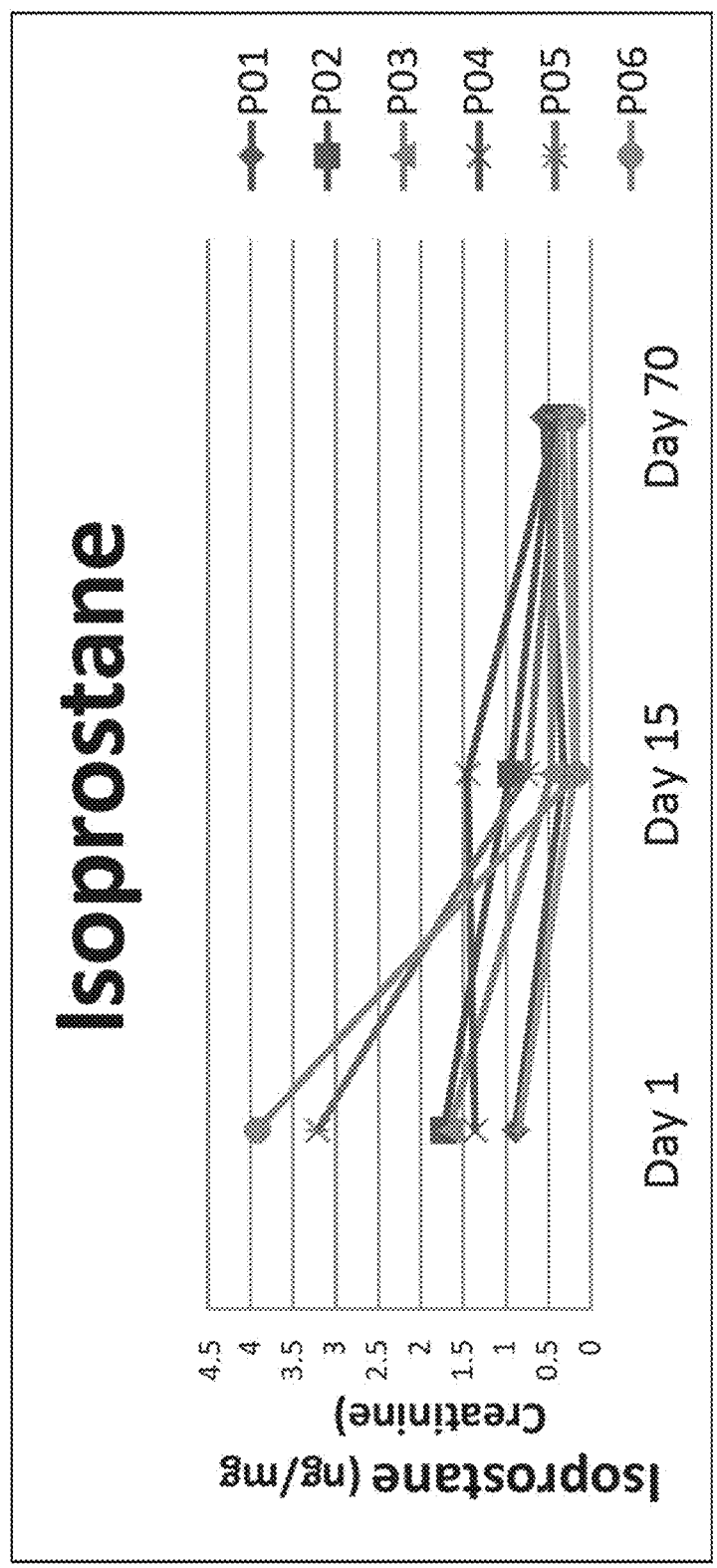
FIG. 8 shows a decrease in the levels of urinary isoprostane in the urine of PTSD-diagnosed combat veterans following administration of a composition of the disclosure.

As shown in FIG. 8, treatment with the supplement caused a decrease in the levels of urinary isoprostane. Isoprostanes are prostaglandin-like compounds formed in vivo from the free radical-catalyzed peroxidation of essential fatty acids (primarily arachidonic acid) without the direct action of cyclooxygenase (COX) enzymes usually involved in prostaglandin production. These compounds are accurate markers of lipid peroxidation in both animal and human models of oxidative stress. At day 15, most subjects displayed decreased isoprostane levels. By day 70, all subjects displayed isoprostane levels lower than at day 1.

As seen in Table 3A and Table 3B, treatment with the composition resulted in marked decreases in the amount of isoprostane after just 15 days of treatment. Table 2A displays the raw data from the study, while table 3B displays the results following calculation of percentage reduction and percentage improvement of oxidative stress marker. In Tables 3A and 3B, "PTSD+" is a participant who was diagnosed with PTSD. "PTSD−" is a participant not diagnosed with PTSD. "TX+" is a participant who used the composition prior to the study. "TX−" is participant who was naïve to the composition.

As seen in Table 3B, subjects displayed over a 60% reduction in isoprostane levels after 15 days of treatment followed by an additional 3.18% of reduction in isoprostane levels after 70 days of treatment. In addition, subjects displayed over a 469% improvement in levels of oxidative stress biomarker after 15 days of treatment followed by an additional 53.19% improvement in levels of oxidative stress biomarker (isoprostane) after 70 days of treatment.

TABLE 3A

PTSD Oxidative Stress Study Raw Data

|  | Day 1 Isoprostane (ng/mg creatinine) | Day 15 Isoprostane (ng/mg creatinine) | Day 70 Isoprostane (ng/mg creatinine) |
|---|---|---|---|
| PTSD+/TX− P001a | 0.897 | 0.320 | 0.564 |
| PTSD+/TX− P002a | 1.736 | 0.956 | 0.4294 |
| PTSD+/TX− P004a | 1.667 | 0.470 | 0.4068 |
| PTSD+/TX− P005a | 1.365 | 1.456 | 0.3997 |
| PTSD+/TX− P006a | 3.2154 | 0.759 | 0.3514 |
| PTSD+/TX− P007a | 3.923 | 0.177 | 0.2156 |
| PTSD+/TX− P008a | 0.851 | 0.195 | 0.3407 |
| PTSD+/TX+ P009a | 0.566 | 0.834 | 0.483 |
| PTSD−/TX+ P010a | 1.471 | 0.401 | 0.499 |
| PTSD−/TX− P011a | 2.542 | 0.507 | 0.441 |
| PTSD−/TX− P012a | 1.002 | 1.348 | 0.360 |

TABLE 3B

PTSD Oxidative Stress Study Data

|  | Day 1 to Day 15 | | | Day 15 to 70 | | |
|---|---|---|---|---|---|---|
|  | Difference | % Reduction | % Improvement | Difference | % Reduction | % Improvement |
| PTSD+/TX− P001a | −0.577 | −64.30 | −180.12 | 0.243 | 75.96 | 43.17 |
| PTSD+/TX− P002a | −0.78 | −44.94 | −81.62 | −0.53 | −55.07 | −122.57 |
| PTSD+/TX− P004a | −1.198 | −71.85 | −255.20 | −0.06 | −13.33 | −15.38 |
| PTSD+/TX− P005a | 0.0909 | 6.66 | 6.24 | −1.06 | −72.55 | −264.24 |
| PTSD+/TX− P006a | −2.455 | −76.39 | −323.55 | −0.41 | −53.69 | −115.95 |
| PTSD+/TX− P007a | −3.746 | −95.49 | −2116.18 | 0.039 | 21.81 | 17.30 |
| PTSD+/TX− P008a | −0.656 | −77.08 | −336.25 | 0.146 | 74.62 | 45.73 |
| Average change (PTSD+/−) | −1.332 | −60.48 | −469.52 | −0.23 | −3.18 | −59.19 |
| PTSD+/TX+ P009a | 0.269 | 47.47 | 32.19 | −0.35 | −42.06 | −72.60 |
| PTSD+/TX+ P010a | −1.07 | −72.23 | −266.70 | 0.097 | 24.48 | 19.54 |
| PTSD+/TX− P011a | −2.035 | −80.06 | −401.50 | −0.07 | −13.06 | −15.02 |

TABLE 3B-continued

PTSD Oxidative Stress Study Data

| | Day 1 to Day 15 | | | Day 15 to 70 | | |
|---|---|---|---|---|---|---|
| | Difference | % Reduction | % Improvement | Difference | % Reduction | % Improvement |
| PTSD+/TX–P012a | 0.346 | 34.54 | 25.67 | −0.99 | −73.31 | −274.66 |
| % Reduction Oxidative Stress Biomarker (PTSD+/Tx–) | | 60.48% | | | 3.18% | |
| % Improvement Oxidative Stress Biomarker (PTSD+/Tx–) | | 469.52% | | | 59.19% | |

Figure 9:
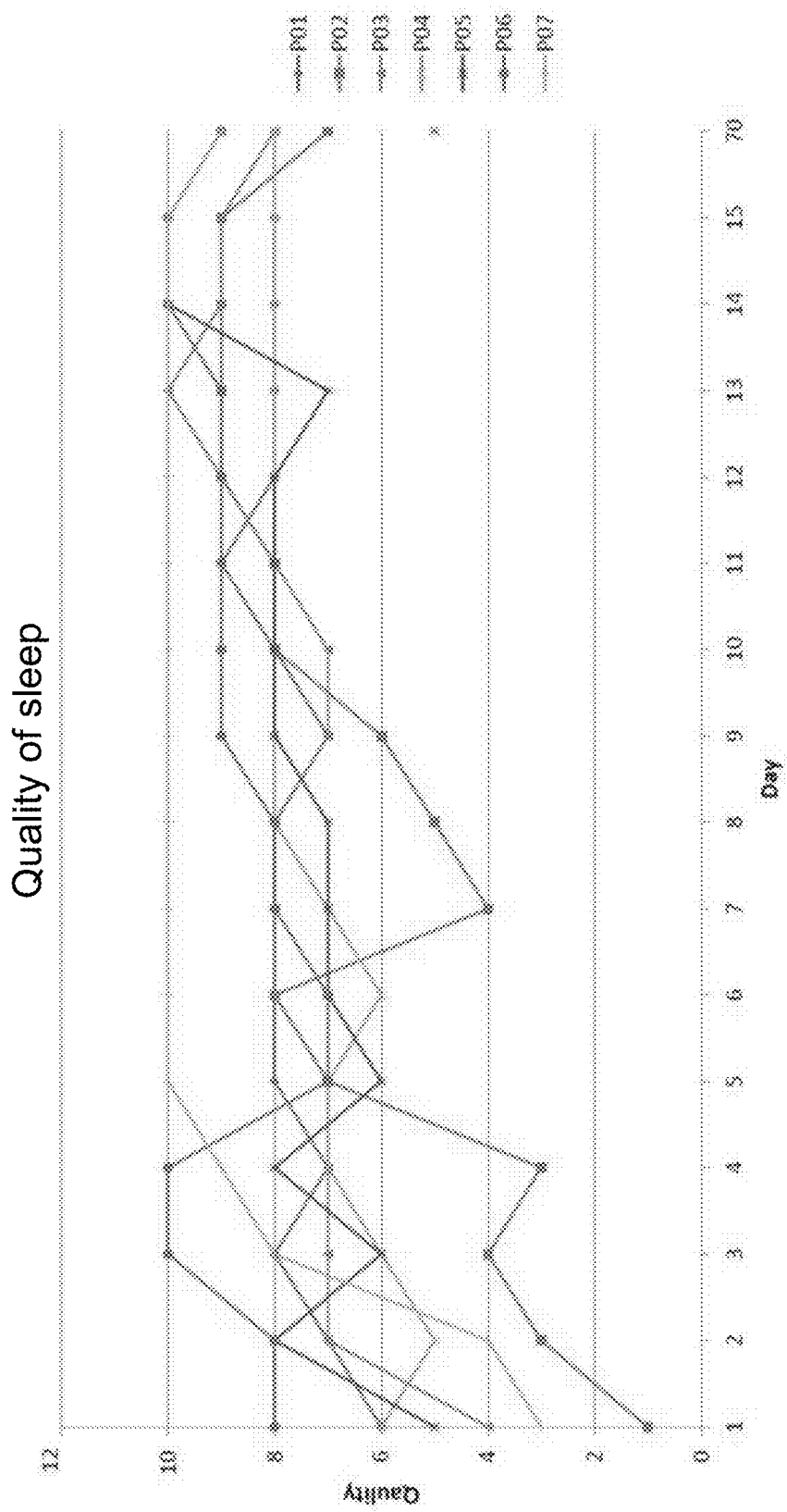
FIG. 9 shows a decrease in sleep deficits of PTSD-diagnosed combat veterans following administration of a composition of the disclosure.

Subjects were asked to self-assess and rate their sleep on a scale of 1-10, where a value of 1 corresponded to a deficit in sleep and a value of 10 corresponded to no deficit in sleep. As seen in FIG. 9, by day 70 all subjects showed decreased deficits in sleep as compared to self-assessed quality of sleep ratings at day 1.

Figure 10:
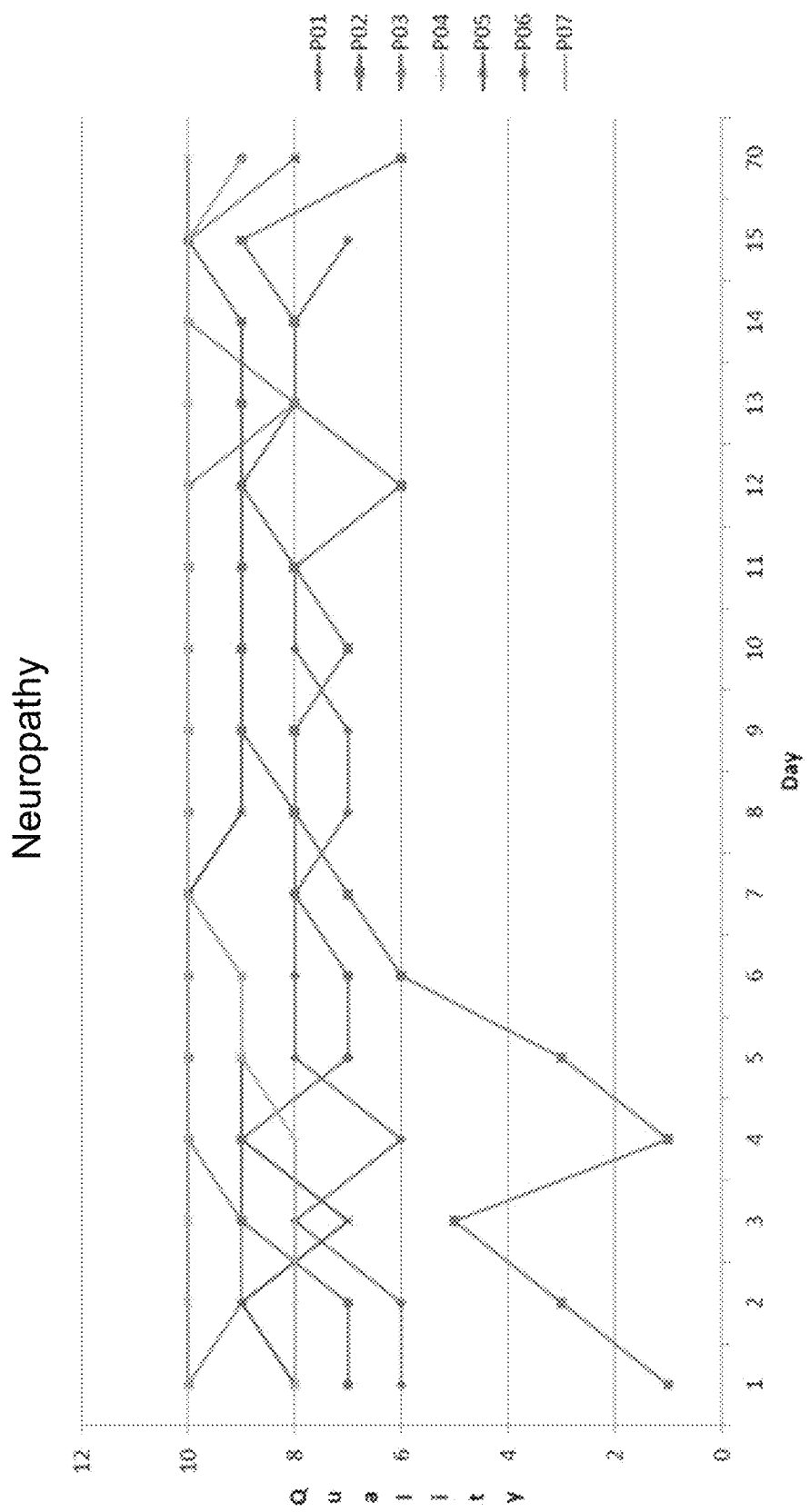
FIG. 10 shows a decrease in neuropathy symptoms in PTSD-diagnosed combat veterans following administration of a composition of the disclosure.

Subjects were asked to self-assess and rate their neuropathy symptoms between a scale of 1-10, where a value of 1 corresponded to great discomfort and pain from neuropathy symptoms and a value of 10 corresponded to minimal discomfort and pain from neuropathy symptoms. As seen in FIG. 10, at day 15 all subjects but two (P03 and P04) showed minimal discomfort and pain from neuropathy symptoms as compared to day 1. At day 70, all patients except for one (P03) showed either minimal discomfort and pain from neuropathy symptoms or—in the case of P04—no difference in discomfort (note that P04 indicated minimal discomfort and pain from neuropathy symptoms at the onset of the study) as compared to day 1.

Figure 11:
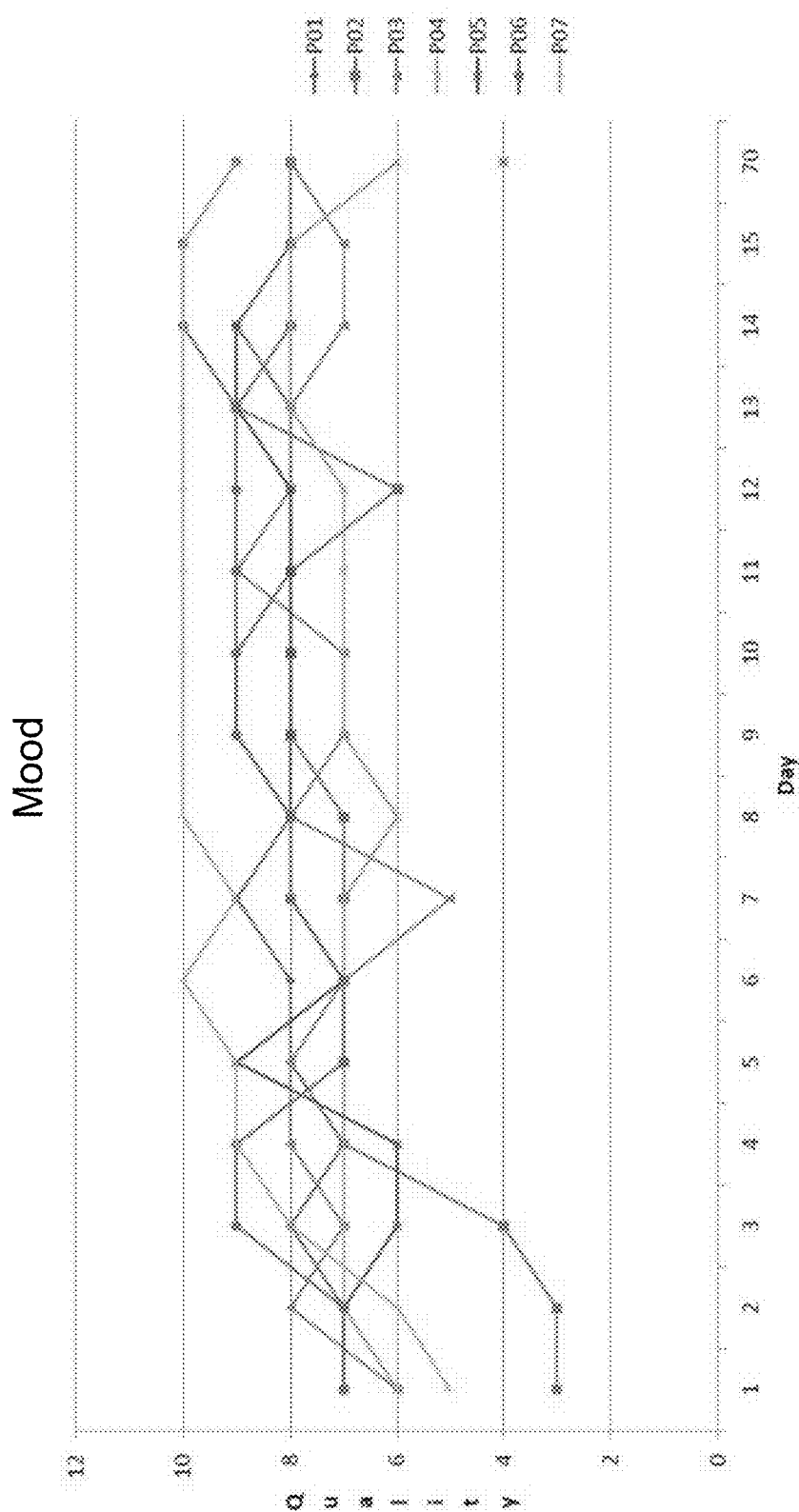
FIG. 11 shows an improvement in the overall mood of PTSD-diagnosed combat veterans following administration of a composition of the disclosure.

Subjects were asked to self-assess and rate their overall mood on a scale of 1-10, where a value of 1 corresponded to a generally unhappy or uneasy mood and a value of 10 corresponded to a general happy or relaxed mood. As seen in FIG. 11, at day 15 all subjects but two showed an improvement in overall mood. At day 70, all patients except for one (P04) showed an improvement in overall mood as compared to day 1.

Figure 12:
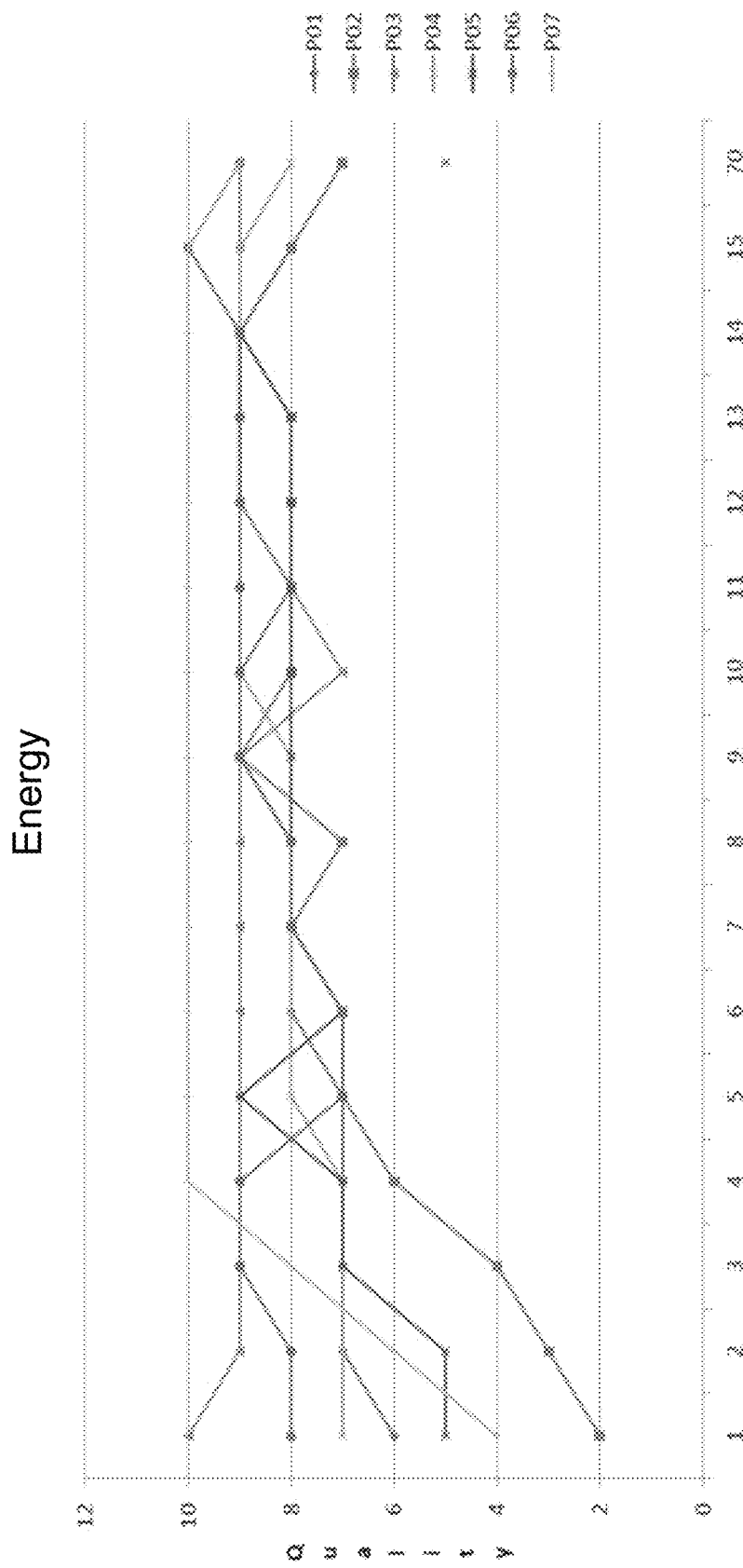
FIG. 12 shows an increase in overall energy levels in PTSD-diagnosed combat veterans following administration of a composition of the disclosure.

Subjects were asked to self-assess and rate their overall levels of energy on a scale of 1-10, where a value of 1 corresponded to a low level of energy and a value of 10 corresponded to a high level of energy. As seen in FIG. 12, at days 15 and 70 all subjects (except P03) displayed an increase in energy levels as compared to day 1.

Figure 13:
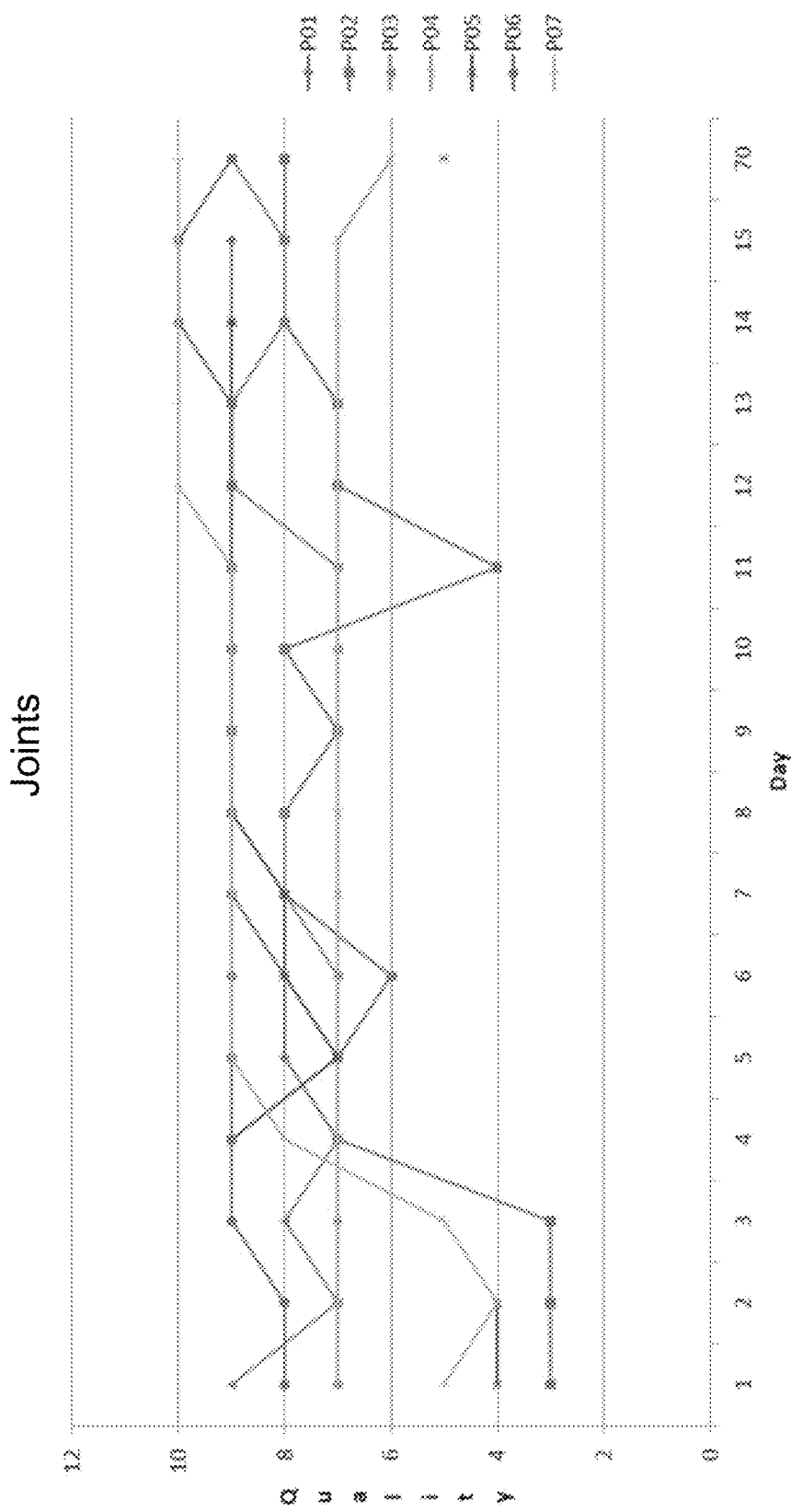
FIG. 13 shows an increase in overall satisfaction with the health of the joints of PTSD-diagnosed combat veterans following administration of a composition of the disclosure.

Subjects were asked to self-assess and rate their overall satisfaction with the health of their joints (as determined by evaluating several factors including flexibility, stiffness and pain) on a scale of 1-10, where a value of 1 corresponded to a low level of satisfaction and a value of 10 corresponded to a high level of satisfaction. As seen in FIG. 13, at day 15 all subjects (except for P03 and P04) displayed improved levels of satisfaction with their joints as compared to day 1. This trend continued at day 70.

Figure 14:
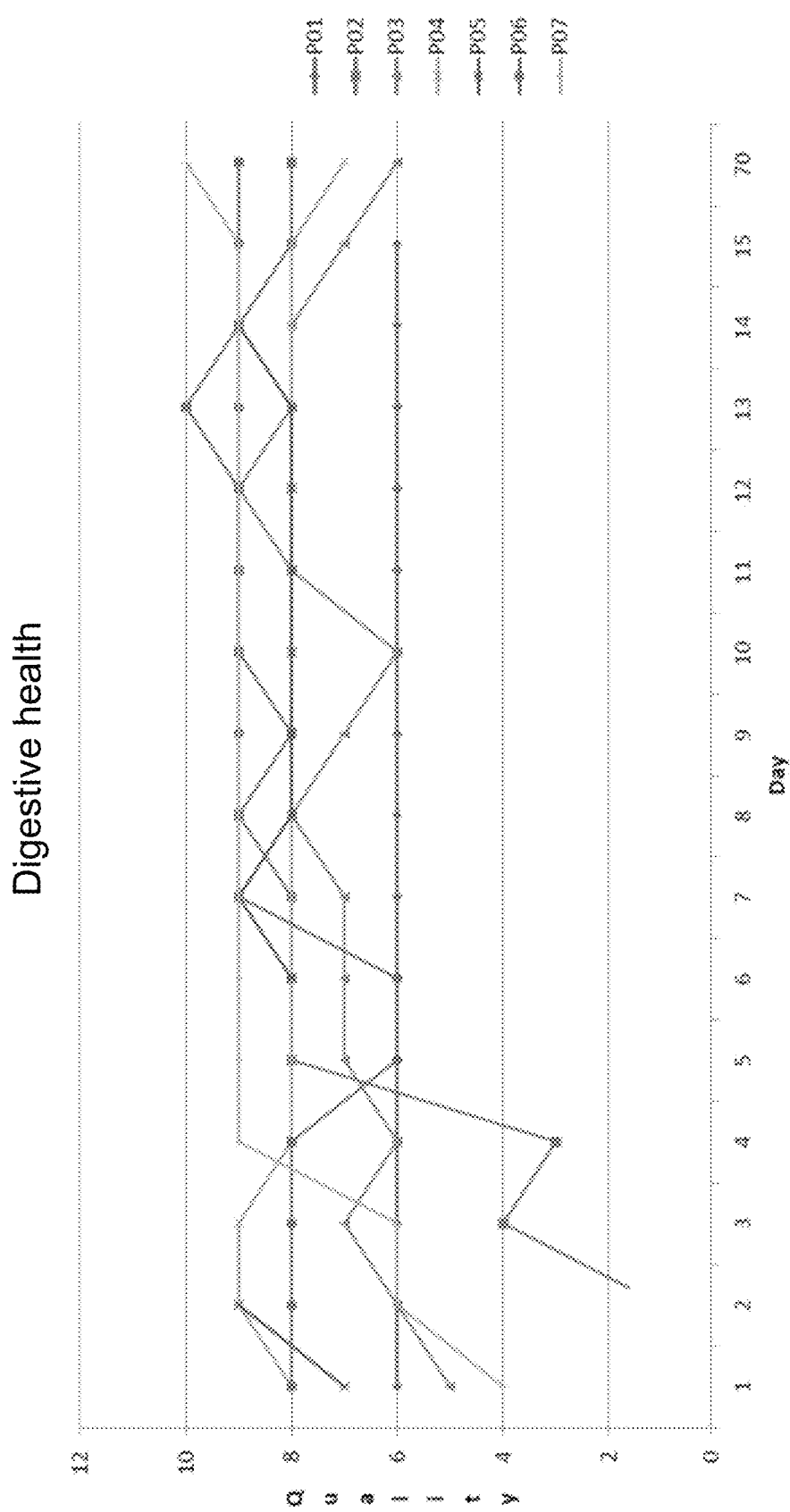
FIG. 14 shows an increase in levels of satisfaction of the digestive health of PTSD-diagnosed combat veterans following administration of a composition of the disclosure.

Subjects were asked to self-assess and rate their overall satisfaction with their digestive health on a scale of 1-10, where a value of 1 corresponded to a low level of satisfaction and a value of 10 corresponded to a high level of satisfaction. As seen in FIG. 14, at day 15 all subjects (except for P01 and P04) displayed improved levels of satisfaction with their digestive health as compared to day 1. This trend continued at day 70.

Figure 15:
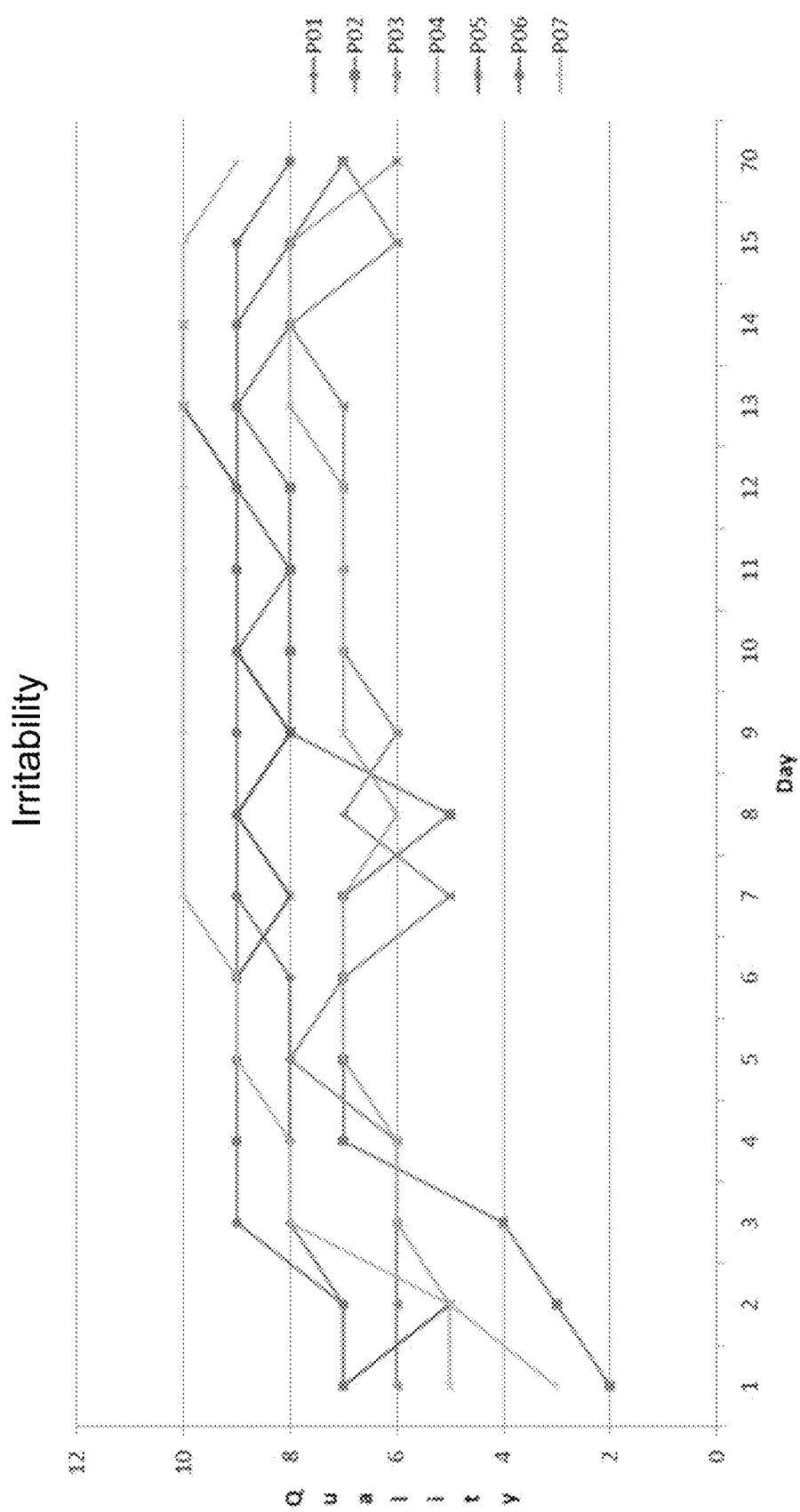
FIG. 15 shows a decrease in levels of irritability of PTSD-diagnosed combat veterans following administration of a composition of the disclosure.

Subjects were asked to self-assess and rate their overall level of irritability on a scale of 1-10, where a value of 1 corresponded to a high level of irritability and a value of 10 corresponded to the lowest level of irritability. As seen in FIG. 15, at day 70 all subjects displayed decreased levels of irritability as compared to day 1.

Figure 16:
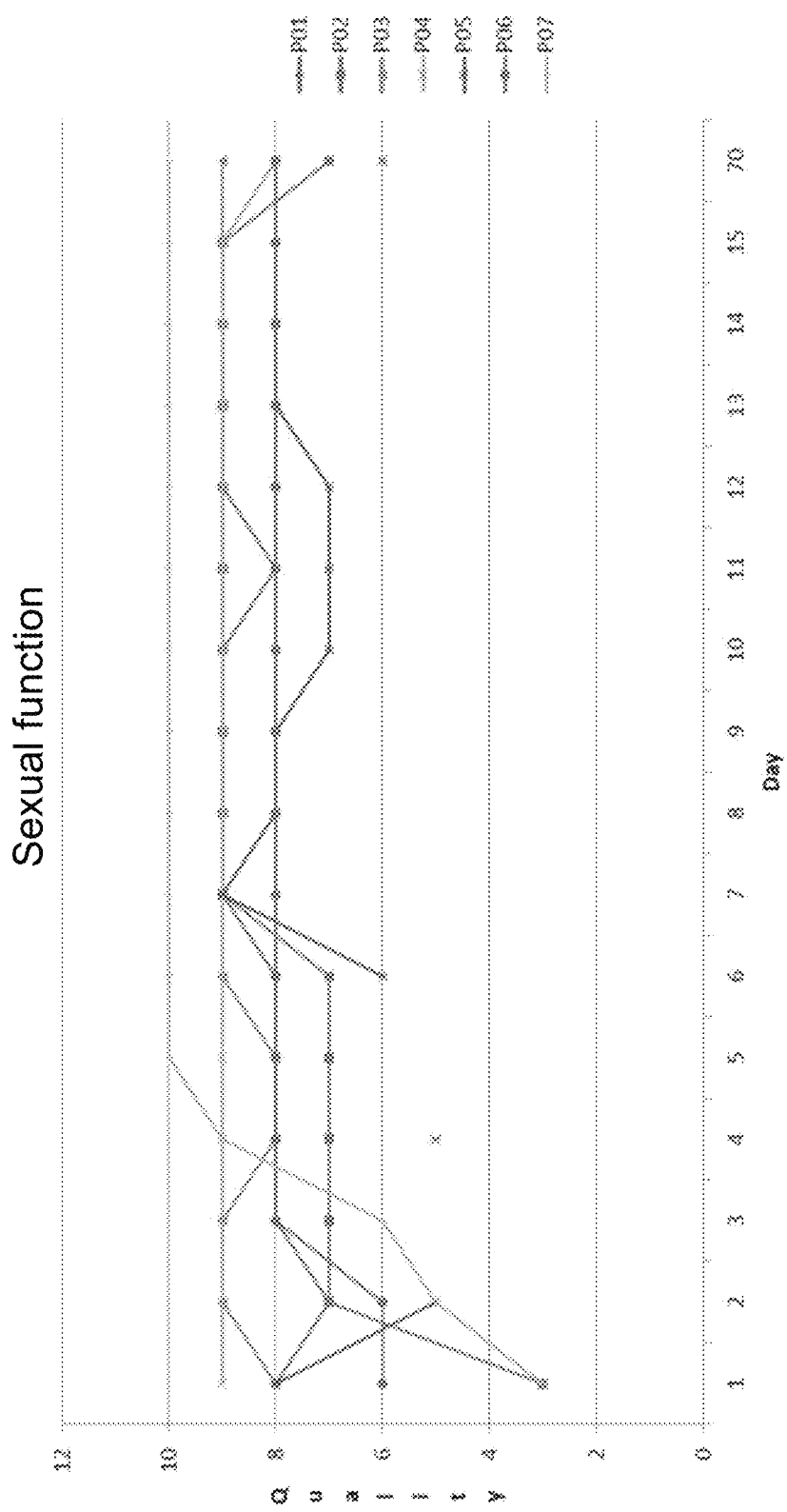
FIG. 16 shows an increase in overall levels of self-reported satisfaction with sexual function of PTSD-diagnosed combat veterans following administration of a composition of the disclosure.

Subjects were asked to self-assess and rate their overall level of satisfaction with their sexual function on a scale of 1-10, where a value of 1 corresponded to a low level of satisfaction and a value of 10 corresponded to a high level of satisfaction. As seen in FIG. 16, at day 70 all subjects (except P04 and P05) displayed increased levels of satisfaction with their sexual performance as compared to day 1.

Subjects were asked to self-assess and rate their overall level of daytime sleepiness in accordance with the guidelines of the Epworth Sleepiness Scale (ESS). The ESS is a self-administered questionnaire with 8 questions. It provides a measure of a person's general level of daytime sleepiness, or their average sleep propensity in daily life. It has become the world standard method for making this assessment. The ESS asks people to rate, on a 4-point scale (0-3), their usual chances of dozing off or falling asleep in 8 different situations or activities that most people engage in as part of their daily lives, although not necessarily every day. It does not ask people how often they doze off in each situation. That would depend very much on how often they happened to be in those situations. Rather it asks what the chances are that they would doze off whenever they were in each situation. This requires a mental judgment which, it seems, most people are able to make in a meaningful way. The total ESS score is the sum of 8 item-scores and can range between 0 and 24. The higher the score, the higher the person's level of daytime sleepiness. The total ESS score provides an estimate of a general characteristic of each person—their average level of sleepiness in daily life.

Figure 17:
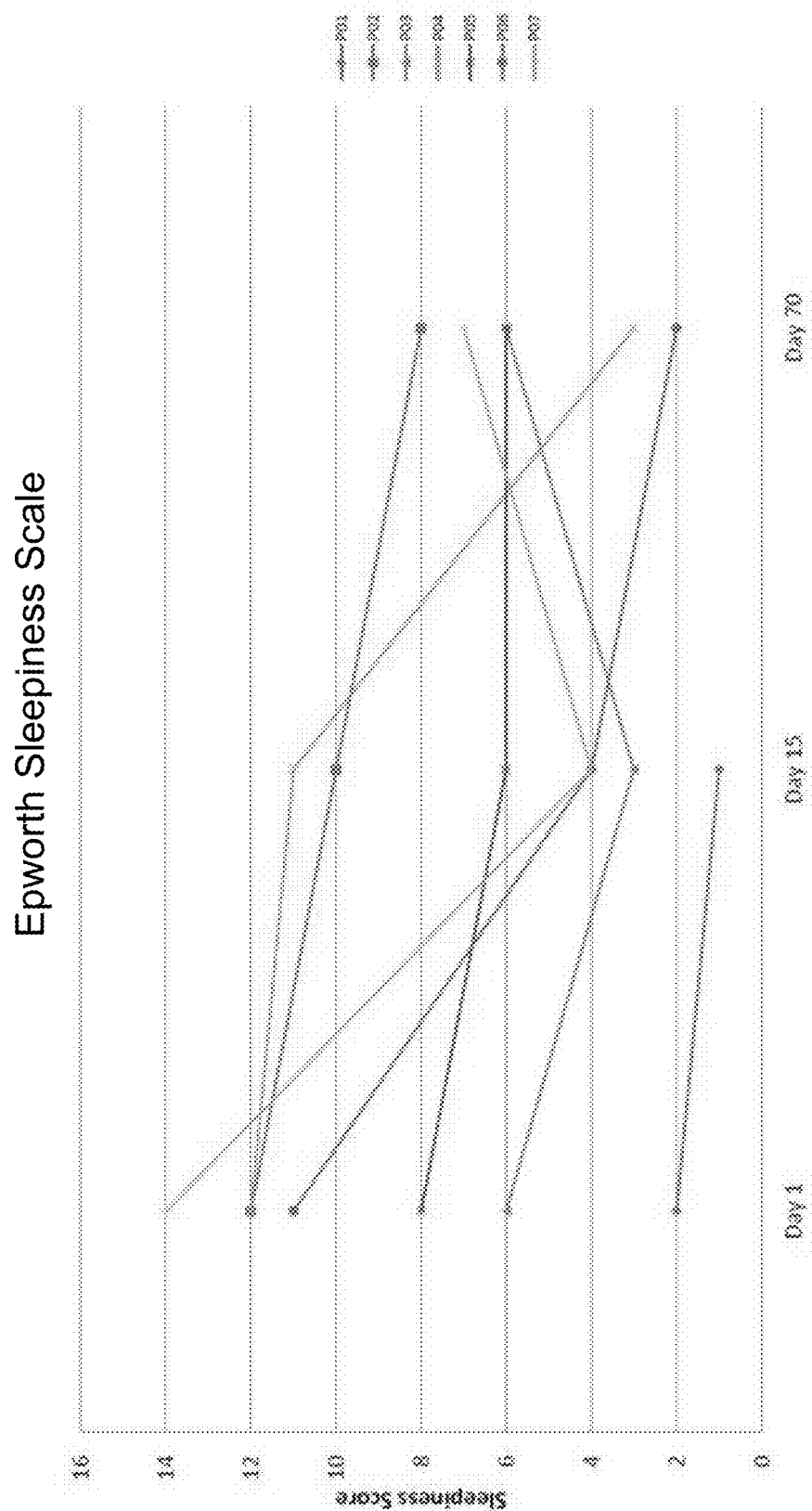
FIG. 17 shows a decrease in daytime sleepiness of PTSD-diagnosed combat veterans following administration of a composition of the disclosure.

As seen in FIG. 17, all subjects displayed decreased daytime sleepiness by day 15. At day 70, all subjects completing the study (except P03) displayed decreased day-time sleepiness as compared to day 1.

Figure 18:
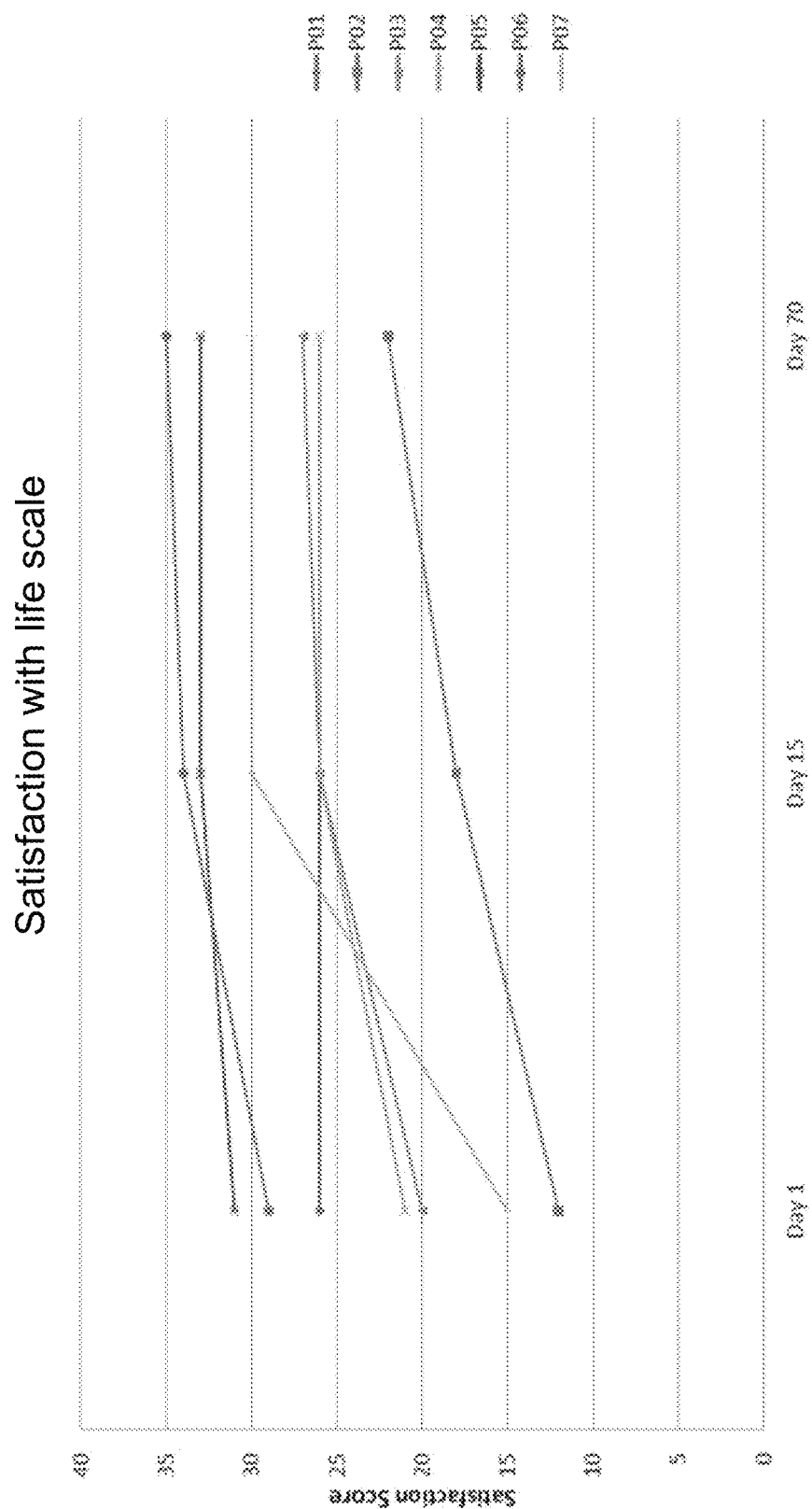
FIG. 18 shows an increase in overall levels of self-reported satisfaction with the lives PTSD-diagnosed combat veterans following administration of a composition of the disclosure.

Subjects were asked to self-assess and rate their overall level of satisfaction with their life on a scale of 1-40, where a value of 1 corresponded to a low level of satisfaction and a value of 40 corresponded to a high level of satisfaction. As seen in FIG. 18, at day 15 all subjects displayed increased levels of satisfaction with their lives as compared to day 1. This trend continued to day 70.

Subjects were asked to self-assess and rate their overall level of anxiety in accordance with the guidelines of the Zung Self-Rating depression scale. The Zung Self-Rating Depression Scale was designed by Duke University psychiatrist William W. K. Zung MD (1929-1992) to assess the level of depression for patients diagnosed with depressive disorder.

Figure 19:
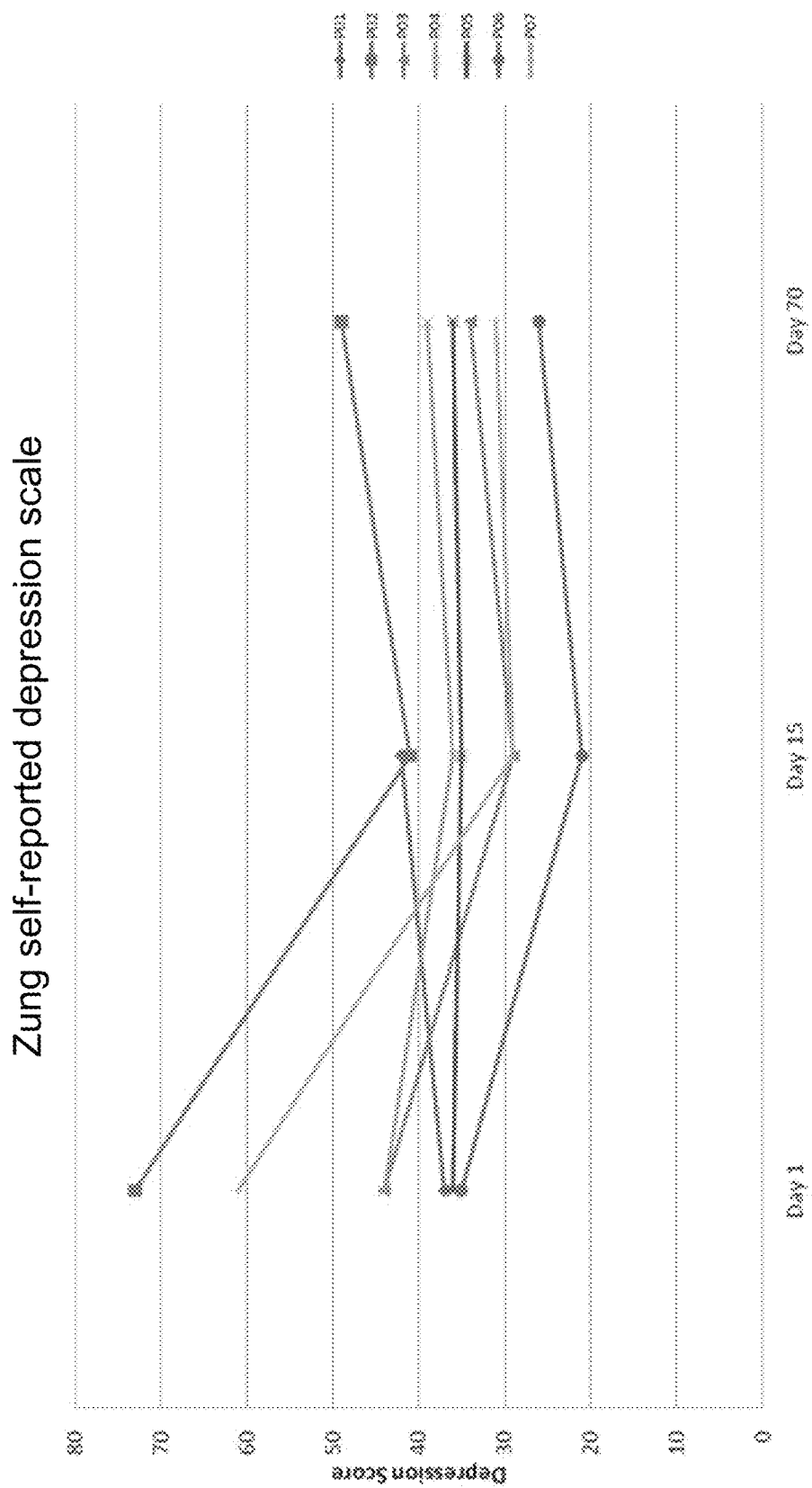
FIG. 19 shows a decrease in levels of depression in PTSD-diagnosed combat veterans following administration of a composition of the disclosure.

The Zung Self-Rating Depression Scale is a short self-administered survey to quantify the depressed status of a patient. There are 20 items on the scale that rate affective, psychological, and somatic symptoms associated with depression. There are ten positively worded and ten negatively worded questions. Each question is scored on a scale of 1 through 4 (based on these replies: "a little of the time", "some of the time", "good part of the time", "most of the time"). Scores on the test range from 20 through 80. The scores fall into four ranges, where: 20-44 correlates to a normal range, 45-59 correlates to a state of mild depression, 60-69 correlates to the state of moderate depression, and 70+ correlates to a state of severe depression. As seen in FIG. 19, at day 15 all subjects except for P01 and P05 displayed decreased levels of depression as compared to day 1. At day 70, subjects P02, P03, P04, P06 and P07 all displayed decreased levels of anxiety as compared to day 1.

Example 5: Reduction of Oxidative Stress-Related Side Effects

Reduction of Headache.

Figure 20:
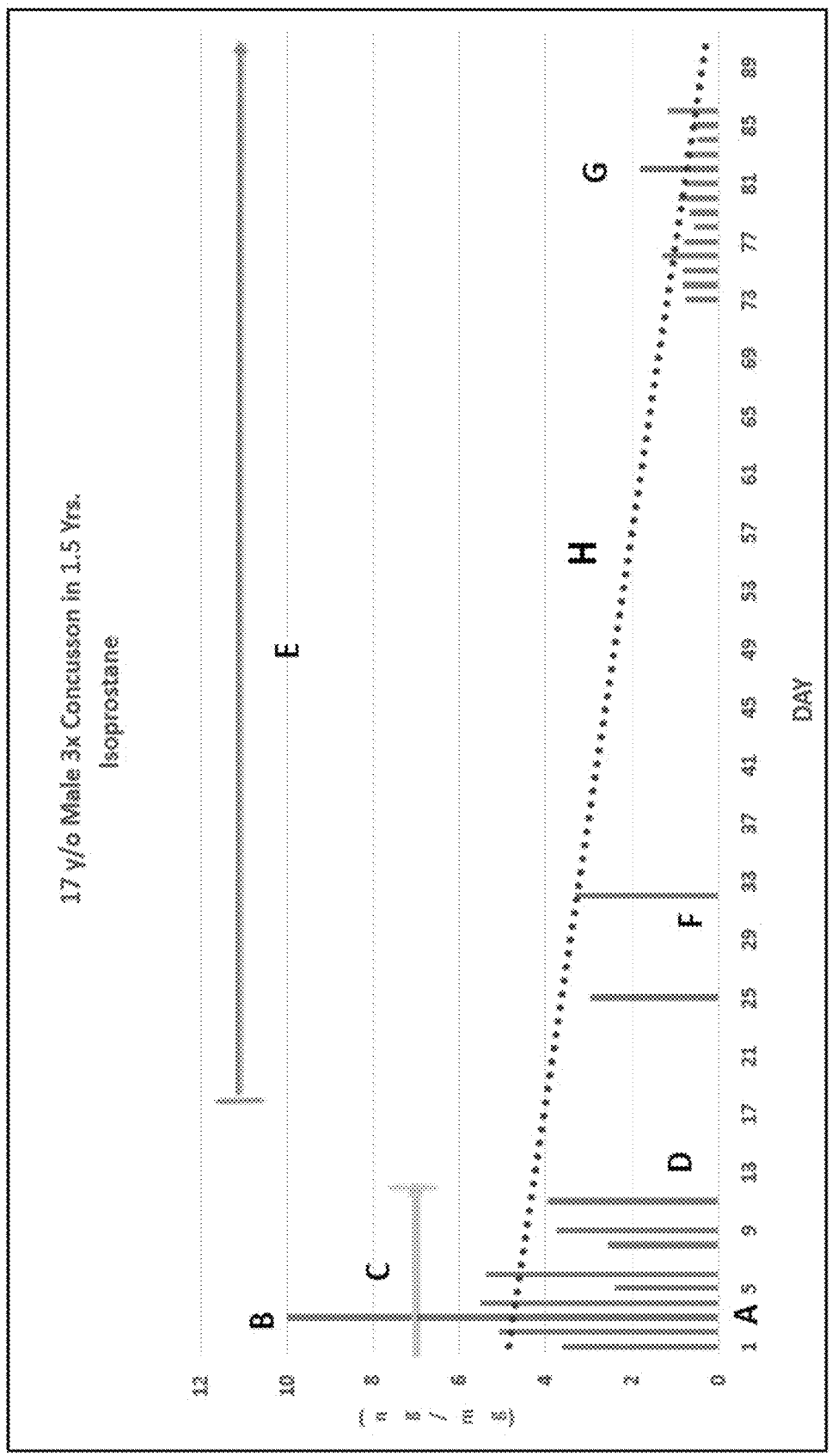
FIG. 20 shows a decrease in isoprostane levels in an individual with a history of concussion following administration of a lysate of the disclosure.

A 17-year-old male that experienced three concussions in the 1.5 years prior to treatment was administered a lysate of the disclosure at a dose of 45 mg twice daily. At day 14 of treatment, the dosage was increased to 75 mg active ingredient twice daily. Prior to treatment, the patient reported frequent headaches. Pre-treatment F2-isoprostane (F2IsoP) was measured in urine at 2.4 ng per mg creatinine. FIG. 20 shows a decrease over 85 days in isoprostane as measured in the patient's urine, with an average of 0.82 ng isoprostane/mg creatinine from days 72-85. Letters A-H in FIG. 20 denote the following events: (A) Days 1 to 3, baseline F2IsoP levels; (B) Day 3, severe headache at the 9.99 ng/mg F2IsoP peak; (C) Days 1 to 13, using 45 mg b.i.d. lysate, with daily headaches; (D) Day 13, patient begins using 75 mg b.i.d. lysate to address headaches; (E) Days 18 to 89, headaches now resolved and continue to be resolved; (F) Day 30, new impact event playing football, headache for 18 hours with visual and neurological disturbances; (G) Day 81, situational stress event, showing elevated F2IsoP levels, but did not result in headache; (H) Days 1 to 89, trend line of isoprostane showing 98% reduction over 89 days. Overall, these data suggest a concomitant decrease in oxidative stress in response to lysate administration. Additionally, the subject reported a marked decrease in headaches following lysate administration.

Reduction of Other Oxidative Stress-Related Side Effects.

A patient experiencing one or more side effects associated with administration of a pharmaceutical agent is co-administered a bacterial lysate of the disclosure at a dose of 45-100 mg b.i.d. Prior to beginning co-administration of lysate, F2-isoprostane levels are measured in blood or urine. Co-administration of lysate produces a continual decrease in F2IsoP levels over time, with approximately 50% overall reduction in F2IsoP levels over about 45 days, and approximately 95% reduction in F2IsoP levels over about 90 days, with concomitant reduction in drug-related oxidative stress-associated side effects.

Example 6: Lysate/Adalimumab Combination is Effective for Treatment of Skin Disease in Psoriatic Arthritis A study is performed to evaluate the efficacy of a therapeutic composition comprising adalimumab in combination with a bacterial lysate composition of the disclosure, administered in conjunction or separately, for cutaneous disease in patients with psoriatic arthritis (PsA), an oxidative stress disorder.

A randomized Phase III study of adalimumab is studied in patients with active PsA (≥3 swollen and ≥3 tender joints) who had failed NSAID therapy. Randomization is centrally stratified by methotrexate (MTX) use and extent of psoriasis (<3% or ≥3% body surface area [BSA]) at baseline. Patients completing Week 24 will be eligible to continue in an open-label extension study.

Patients are included if they have a history of psoriasis; are over 18 years; ≥3 swollen and ≥3 tender joints; and inadequate response to NSAID therapy. Exclusion criteria includes prior anti-TNF therapy; alefacept within 12 weeks prior to study entry; other biologics within 6 weeks prior to study entry; DMARDs (except MTX) within 4 weeks prior to study entry; systemic therapies for psoriasis within 4 weeks prior to study entry; and phototherapy and topicals within 2 weeks prior to study entry.

Patients are stratified by methotrexate use (yes/no) and degree of psoriasis (<3% and ≥3% BSA involvement) and receive lysate 20-50 mg orally on a daily basis, in combination with adalimumab, 40 mg every other week or placebo for 24 weeks.

Efficacy measures to be used include: ACR response criteria (co-primary endpoint: ACR20 response at Week 12); Psoriasis Area and Severity Index (PASI) in patients with significant psoriasis at study entry (≥3% BSA); and Physician's Global Assessment (PGA) of psoriasis. The study examines patients according to the severity of psoriasis at baseline: PASI<10 vs. PASI≥10

Thus, efficacy measures in patients with psoriasis affecting ≥3% BSA at baseline include PASI, PGA of psoriasis, and DLQI. ACR response criteria are also used as an efficacy measurement. A post-hoc analysis is conducted for patients with baseline PASI<10 vs. those with PASI≥10. PASI analyses are by NRI, and PGA and DLQI scores are calculated as LOCF.

The treatment group receiving co-administered lysate experiences amelioration of injection site reactions (such as pain, redness, or irritation) and less overall oxidative stress-related side effects, which will allow for increased adherence and compliance with treatment, which in turn allows a greater opportunity for ameliorating the primary disease.

Example 7: Lysate/Statin/ACE Inhibitor Combinations are Effective for Treatment of Hypertension A human subject being treated for hypertension and receiving a combination of 20 mg QD pravastatin and 20 mg QD lisonopril was experiencing oxidative stress-related side effects of skin rash and insomnia.

When the patient was additionally administered 45 mg bid of a lysate encompassed by the disclosure herein, the skin rash and insomnia side effects resolved within 60 days.

Example 8: Lysate/SSRI Combination is Effective for Treatment of Clinical Depression A human subject being treated for depression and receiving 60 mg QD duloxetine (CYMBALTA®) was experiencing oxidative stress-related side effects of anorgasmia, dizziness, numbness, and irritability.

When the patient was additionally administered 45 mg bid of a lysate encompassed by the disclosure herein, anorgasmia resolved within 10 days, dizziness resolved within 7 days, numbness resolved within 10 days, and irritability resolved within 5 days.

Example 9: Lysate/Hormone Combination is Effective for Treatment of Hypothyroidism A human subject being treated for hypothyroidism and receiving 150 mcg QD of levothyroxine (SYNTHROID®) was experiencing oxidative stress-related side effect of hair loss.

When the patient was additionally administered 75 mg bid of a lysate encompassed by the disclosure herein, the hair loss side effect resolved within 180 days.

Example 10: Lysate/Reverse Transcriptase Inhibitor Combination is Effective for Treatment of HIV Infection A human subject being treated for HIV (non-AIDS) and receiving one tablet QD of efavirenz/emtricitabine/tenofovir disoproxil fumarate (ATRIPLA®) was experiencing oxidative stress-related side effects of erectile dysfunction, neuropathy, insomnia, and brain fog.

When the patient was additionally administered 45 mg bid of a lysate encompassed by the disclosure herein, erectile dysfunction resolved within 10 days, neuropathy resolved within 10 days, insomnia resolved within 3 days, and brain fog resolved within 3 days.

Example 11: Lysate/Direct-Acting Antiviral Drug Combination is Effective for Treatment of Hepatitis C A human subject being treated for Hepatitis C and receiving one tablet QD of ledipasvir/sofosbuvir (HARVONI®) was experiencing oxidative stress-related side effects of brain fog, headache, and arthritis.

When the patient was additionally administered 75 mg bid of a lysate encompassed by the disclosure herein, brain fog resolved within 3 days, headache resolved within 10 days, and arthritis resolved within 14 days.

Example 12: Lysate/Anti-Cancer Drug Combination is Effective for Treatment of Cancer A human subject being treated for cancer and receiving a biweekly dose of topoisomerase I inhibitor/vinca alkaloids/alkylating antineoplastic (IRINOTECAN®, VINCRISTIN®, TEMODAR®) was experiencing oxidative stress-related side effects of brain fog, malaise, insomnia, and rash.

When the patient was additionally administered 75 mg bid of a lysate encompassed by the disclosure herein, brain fog resolved within 3 days, malaise resolved within 5 days, insomnia resolved within 5 days, and rash resolved within 14 days.

Example 13: Lysate/Insulin Analog Combination is Effective for Treatment of Type 2 Diabetes A human subject being treated for type 2 diabetes and receiving a daily dose of the insulin analog insulin glargine (LANTUS®) was experiencing oxidative stress-related side effects of rash (injection site), irritability, and headache.

When the patient was additionally administered 45 mg bid of a lysate encompassed by the disclosure herein, irritability resolved within 5 days, headache resolved within 7 days, and rash (injection site) resolved within 10 days.

Example 14: Lysate/Antibiotic Combination is Effective for Treatment of Rheumatoid Arthritis A human subject diagnosed with rheumatoid arthritis and being treated with an TNF inhibitor was also being treated with antibiotics that caused Grade 3 diarrhea as determined by National Cancer Institute (NCI) standards for the prior ten months. Concurrently the subject was receiving additional antibiotics in order to combat a *Clostridium difficile* infection due to the severe diarrhea. Without changing current pharmacologic therapies, the subject was additionally administered 45 mg lysate twice a day. Diarrhea began to resolve within 2 weeks and improved to an NCI Grade 2 standard in one month.

Example 15: Lysate/Radiation Combination is Effective for Treatment of Cancer A human subject was being treated for prostate cancer and received radiation treatments increasing in intensity and/or duration over the course of 40 days of prescribed therapy as follows: 8 sessions at 180 cGy (1 cGy=1 rad) during week day on nine points in two bursts one at 8 seconds one at 5 seconds; 8 sessions at 180 cGy with bursts of 12 and 9 seconds; 9 sessions at 180 cGy with bursts of 14 and 10 seconds on the right 2 quadrants and then 12 and 9 seconds on the left; and 16 sessions at 200 cGy two continuous full circumference passes for 80 seconds and every other session being two complete continuous, full circumference passes in opposite directions. The radiation dose change was always on a Monday and the patient was seen by a physician each subsequent Tuesday to assess side effects. Each increase resulted in 3 hrs. of nausea, occurring approximately 2 hrs. post treatment and resolved completely in no more than 6 hrs after any treatment session. In combination with the radiation treatment, the patient was administered a lysate of the disclosure at a dose of 75 mg, three times a day. The patient was not administered any other treatment for nausea, vomiting or bleeding. On a Quality of Life scale of 1 to 10 ("1" being the worst, "10" the best) the patient reported an 8 through commencement of the final escalation of exposure. The patient reported nausea to be no worse than a 7 at the greatest exposure and continued to function daily in his work duties throughout treatment.

Given the variety of mechanisms of action of the above drugs with which the lysate compositions of the disclosure are co-administered, and given the mechanism of action of the lysate itself, the lysate compositions disclosed herein can be reasonably extrapolated to provide beneficial adverse-effect-reducing results with most any drug. For example, with HUMIRA®, an injectable a-TNF, co-administration with lysate produces amelioration of injection site irritations. Per package insert this drug is identified as causing arthritis as is seen in the Direct Acting Antiviral, HARVONI®. When a patient uses a lysate of the disclosure in conjunction with a prescribed HCV medication such as HARVONI®, side effects are diminished during treatment and do not persist post treatment.

It should be understood the arrangements and functions described herein are presented for purposes of example only, and that numerous variations are possible. For instance, elements can be added, omitted, combined, distributed, reordered, or otherwise modified. The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described embodiments can be configured without departing from the scope of the invention. The exemplified embodiments have been set forth only for the purposes of example and that should not be taken as limiting the invention. Therefore, it is to be understood that, within the scope of the appended claims, the invention may be practiced other than as specifically described herein.

What is claimed is:

1. A method of regulating redox status in a subject, the method comprising administering a therapeutically effective amount of a composition to a subject in need thereof, the composition comprising:
   (a) at least one lysate of an inactivated Gram-positive bacterium comprising the entire cellular contents of the bacterium cell, wherein the lysate of the Gram-positive bacterium comprises a toll-like receptor (TLR) agonist that regulates redox status in the subject, wherein the TLR agonist activates two or more TLRs, wherein the two or more TLRs comprise TLR2 and TLR4, and wherein the Gram-positive bacterium is inactivated by a heat treatment of the Gram-positive bacterium and by a lysozyme treatment of the Gram-positive bacterium;
   (b) an optional promoter for enhancing absorption of the composition; and
   (c) an optional carrier for increasing a volume of the composition,
   wherein redox status regulation is assessed by measuring changes in isoprostane concentration in a subject and wherein administration of an effective amount of the composition to the subject measurably reduces oxidative stress levels and decreases isoprostane concentration in the subject.

2. The method according to claim 1, wherein the subject is a mammal.

3. The method according to claim 2, wherein the mammal is a human.

4. The method of claim 1, wherein the subject is a non-mammal.

5. The method of claim 4, wherein the subject is a fish, fowl, crustacean, or insect.

6. The method of claim 5, wherein the insect is *Drosophila*.

7. The method according to claim 3, wherein the redox status is oxidative and results in oxidative stress.

8. The method of claim 1, wherein the Gram-positive bacterium is-selected from the group consisting of: *Bacillus coagulans, Lactobacillus sporogenes, Bifidobacterium animalis*, subspecies *animalis, Bifidobacterium infantis, Bifidobacterium longum, Bifidobacterium breve, Lactobacillus acidophilus, Lactobacillus plantarum, Lactobacillus casei, Lactobacillus delbrueckii, Lactobacillus delbrueckii* subspecies *bulgaricus, Lactococcus lactis, Lactococcus lactis* subspecies *lactis, Streptococcus lactis, Streptococcus thermophilus, Bifidobacterium lactis, Pediococcus acidilactici*, and *Lactobacillus helveticus*.

9. The method of claim 1, wherein the heat treatment is pasteurization at a temperature in the range of about 75° C. to about 85° C. and for about 30 minutes to about 60 minutes.

10. The method of claim 1, wherein the lysozyme treatment is conducted at a temperature in the range of about 25° C. to about 50° C. and for about 1 hour to about 10 hours.

* * * * *